(12) United States Patent
Salaam-Zayid et al.

(10) Patent No.: US 10,792,384 B2
(45) Date of Patent: Oct. 6, 2020

(54) ROLLED FIBROUS STRUCTURES COMPRISING ENCAPSULATED MALODOR REDUCTION COMPOSITIONS

(71) Applicant: The Procter & Gamble Company, Cincinnati, OH (US)

(72) Inventors: LaTisha Evette Salaam-Zayid, Cincinnati, OH (US); Jose Enrique Betancourt, West Chester, OH (US); Judith Ann Hollingshead, Batavia, OH (US); Laura Lynn McElroy, Okeana, OH (US); Nancy L. Schuchter, Cold Spring, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 16/200,900

(22) Filed: Nov. 27, 2018

(65) Prior Publication Data

US 2019/0184049 A1 Jun. 20, 2019

Related U.S. Application Data

(60) Provisional application No. 62/599,218, filed on Dec. 15, 2017.

(51) Int. Cl.
| | | |
|---|---|---|
| *A61L 2/232* | (2006.01) | |
| *A47K 10/16* | (2006.01) | |
| *A61L 9/013* | (2006.01) | |
| *A61L 9/012* | (2006.01) | |

(52) U.S. Cl.
CPC ............... *A61L 2/232* (2013.01); *A47K 10/16* (2013.01); *A61L 9/012* (2013.01); *A61L 9/013* (2013.01)

(58) Field of Classification Search
CPC ......... A47K 10/16; A61L 9/013; A61L 9/012; A61L 2/232
See application file for complete search history.

(56) References Cited

U.S. PATENT DOCUMENTS

| | | |
|---|---|---|
| 2,438,091 A | 3/1948 | Lynch |
| 2,528,378 A | 10/1950 | Mannheimer |
| 2,658,072 A | 11/1953 | Kosmin |
| 2,809,971 A | 10/1957 | Bernstein et al. |
| 3,236,733 A | 2/1966 | Karsten et al. |
| 3,753,196 A | 8/1973 | Kurtz et al. |
| 3,761,418 A | 9/1973 | Parran, Jr. |
| 3,792,068 A | 2/1974 | Luedders et al. |
| 3,887,692 A | 6/1975 | Gilman |
| 3,904,741 A | 9/1975 | Jones et al. |
| 3,994,771 A | 11/1976 | Morgan, Jr. et al. |
| 4,049,792 A | 9/1977 | Elsnau |
| 4,120,948 A * | 10/1978 | Shelton .................... A61K 8/02 424/66 |
| 4,137,180 A | 1/1979 | Naik et al. |
| 4,237,155 A | 12/1980 | Kardouche |
| 4,300,981 A | 11/1981 | Carstens |
| 4,323,683 A | 4/1982 | Bolich, Jr. et al. |
| 4,345,080 A | 8/1982 | Bolich, Jr. |
| 4,359,456 A | 11/1982 | Gosling et al. |
| 4,379,753 A | 4/1983 | Bolich, Jr. |
| 4,430,243 A | 2/1984 | Bragg |
| 4,470,982 A | 9/1984 | Winkler |
| 4,985,238 A | 1/1991 | Tanner et al. |
| 5,019,375 A | 5/1991 | Tanner et al. |
| 5,104,646 A | 4/1992 | Bolich, Jr. et al. |
| 5,106,609 A | 4/1992 | Bolich, Jr. et al. |
| 5,296,622 A | 3/1994 | Uphues et al. |
| 5,429,816 A | 7/1995 | Hofrichter et al. |
| 5,486,303 A | 1/1996 | Capeci et al. |
| 5,489,392 A | 2/1996 | Capeci et al. |
| 5,516,448 A | 5/1996 | Capeci et al. |
| 5,565,422 A | 10/1996 | Del Greco et al. |
| 5,569,645 A | 10/1996 | Dinniwell et al. |
| 5,574,005 A | 11/1996 | Welch et al. |
| 5,576,282 A | 11/1996 | Miracle et al. |
| 5,595,967 A | 1/1997 | Miracle et al. |
| 5,597,936 A | 1/1997 | Perkins et al. |
| 5,691,297 A | 11/1997 | Nassano et al. |
| 5,714,137 A | 2/1998 | Trinh et al. |
| 5,879,584 A | 3/1999 | Bianchetti et al. |
| 5,891,424 A | 4/1999 | Bretzler et al. |
| 5,942,217 A | 8/1999 | Woo et al. |
| 5,976,514 A | 11/1999 | Guskey et al. |
| 6,180,121 B1 | 1/2001 | Guenin et al. |
| 6,225,464 B1 | 5/2001 | Hiler, II et al. |
| 6,248,135 B1 | 6/2001 | Trinh et al. |
| 6,386,392 B1 | 5/2002 | Argentieri et al. |
| 6,413,920 B1 | 7/2002 | Bettiol et al. |

(Continued)

FOREIGN PATENT DOCUMENTS

| | | |
|---|---|---|
| BE | 825146 | 8/1975 |
| CA | 1164347 | 3/1984 |

(Continued)

OTHER PUBLICATIONS

Database WPI; Week 201459; Thomson scientific, London, GB; AN 2014-P66521; XP002752638.
ASTM D3954-94, Reapproved 2010, vol. 15.04, Standard Test Method for Dropping Point of Waxes.
Todd, C., et al., Volatile silicone fluids for cosmetic formulations, Cosmetics and Toiletries, Jan. 1976, pp. 29-32, vol. 91.
Crepaldi, E.L., et al., Chemical, Structural, and Thermal Properties of Zn(II)-Cr(III) Layered Double Hydroxides Intercalated with Sulfated and Sulfonated Surfactants, Journal of Colloid and Interface Science, 2002, pp. 429-442, vol. 248.

(Continued)

*Primary Examiner* — Blessing M Fubara

(74) *Attorney, Agent, or Firm* — C. Brant Cook

(57) ABSTRACT

The present invention relates to a fibrous structure including one or more encapsulated malodor reduction compositions and methods of making and using such a fibrous structure.

20 Claims, No Drawings

(56) References Cited

U.S. PATENT DOCUMENTS

| | | | |
|---|---|---|---|
| 6,436,442 B1 | 8/2002 | Woo et al. | |
| 6,488,943 B1 | 12/2002 | Beerse et al. | |
| 6,656,923 B1 | 12/2003 | Trinh et al. | |
| 6,716,805 B1 | 4/2004 | Sherry et al. | |
| 6,814,088 B2 | 11/2004 | Barnabas et al. | |
| 6,869,923 B1 | 3/2005 | Cunningham et al. | |
| 7,172,099 B2 | 2/2007 | Höfte et al. | |
| 7,202,198 B2 | 4/2007 | Gordon et al. | |
| 7,223,361 B2 | 5/2007 | Kvietok et al. | |
| 8,322,631 B2 | 12/2012 | Richardson et al. | |
| 8,709,337 B2 | 4/2014 | Gruenbacher et al. | |
| 8,772,354 B2 | 7/2014 | Williams et al. | |
| 8,931,711 B2 | 1/2015 | Gruenbacher et al. | |
| 8,940,323 B2 | 1/2015 | Shannon | |
| 9,714,401 B2 * | 7/2017 | Frankenbach | A61L 2/23 |
| 10,113,140 B2 | 10/2018 | Frankenbach et al. | |
| 10,240,108 B2 * | 3/2019 | Frankenbach | A61L 2/23 |
| 2004/0064117 A1 | 4/2004 | Hammons et al. | |
| 2004/0151793 A1 | 8/2004 | Paspaleeva-Kuhn et al. | |
| 2005/0003980 A1 | 1/2005 | Baker et al. | |
| 2005/0276831 A1 | 12/2005 | Dihora et al. | |
| 2007/0003499 A1 | 1/2007 | Shen et al. | |
| 2007/0020263 A1 | 1/2007 | Shitara et al. | |
| 2007/0048474 A1 * | 3/2007 | Butler, III | A47K 10/16 |
| | | | 428/36.9 |
| 2007/0275866 A1 | 11/2007 | Dykstra | |
| 2008/0003245 A1 | 1/2008 | Kroepke et al. | |
| 2009/0240223 A1 | 9/2009 | Warren et al. | |
| 2010/0009285 A1 | 1/2010 | Daems et al. | |
| 2010/0061946 A1 | 3/2010 | Schemer et al. | |
| 2010/0287710 A1 | 11/2010 | Denutte et al. | |
| 2010/0322878 A1 | 12/2010 | Stella et al. | |
| 2011/0253158 A1 * | 10/2011 | Wei | A61K 8/03 |
| | | | 132/200 |
| 2011/0303766 A1 | 12/2011 | Smith | |
| 2012/0004328 A1 | 1/2012 | Huchel et al. | |
| 2012/0009285 A1 | 1/2012 | Wei et al. | |
| 2012/0129924 A1 | 5/2012 | Park et al. | |
| 2012/0219610 A1 | 8/2012 | Smith, III et al. | |
| 2012/0246851 A1 | 10/2012 | Smith, III et al. | |
| 2012/0258150 A1 | 10/2012 | Rauckhorst et al. | |
| 2013/0043145 A1 | 2/2013 | Smith, III et al. | |
| 2013/0043146 A1 | 2/2013 | Smith, III et al. | |
| 2013/0043147 A1 | 2/2013 | Smith, III et al. | |
| 2013/0319463 A1 | 12/2013 | Policicchio | |
| 2014/0201927 A1 | 7/2014 | Bianchetti et al. | |
| 2015/0041086 A1 * | 2/2015 | Polat | 162/111 |
| 2015/0108163 A1 | 4/2015 | Smith et al. | |
| 2016/0206522 A1 | 7/2016 | Ribaut et al. | |
| 2017/0066579 A1 | 3/2017 | Zillges | |

FOREIGN PATENT DOCUMENTS

| | | |
|---|---|---|
| DE | 102004023720 | 12/2005 |
| DE | 102007019369 | 10/2008 |
| EP | 2005939 | 12/2008 |
| GB | 1347950 | 2/1974 |
| GB | 2048229 | 12/1980 |
| GB | 2144992 | 3/1985 |
| GB | 2450727 | 1/2009 |
| WO | WO 96/04937 | 2/1996 |
| WO | WO 00/32601 | 6/2000 |
| WO | WO 2012136651 | 10/2012 |
| WO | WO 2016049407 A1 * | 3/2016 |

OTHER PUBLICATIONS

Morioka, H., et al., Effects of Zinc on the New Preparation Method of Hydroxy Double Salts, Inorganic Chemistry, 1999, pp. 4211-4216, vol. 38, No. 19.

All Office Actions, U.S. Appl. No. 14/865,056.

All Office Actions, U.S. Appl. No. 16/042,148.

* cited by examiner

ROLLED FIBROUS STRUCTURES COMPRISING ENCAPSULATED MALODOR REDUCTION COMPOSITIONS

FIELD OF THE INVENTION

The present invention relates to rolled fibrous structures, and more particularly to rolled sanitary tissue products, for example rolled toilet tissue comprising a core comprising one or more encapsulated malodor reduction compositions, methods of making such fibrous structures, and methods for using such fibrous structures.

BACKGROUND OF THE INVENTION

Bowel movements create unpleasant odors that are oftentimes embarrassing and/or awkward to the person having the bowel movement.

Known attempts at managing and/or masking the odors resulting from bowel movements have included for example perfumed sprays to attempt to mask the odor, fans to attempt to remove the odor and/or the person flushing multiple times during a bowel movement event. While such prior art techniques have utilized perfumes to attempt to mask the malodors they have had little to no success because the perfumes have not been targeted to the specific malodors created during bowel movement events. Another general problem that formulators have experienced is the challenge of keeping any malodor reduction composition stable long enough for it to have an impact when a user uses the toilet tissue.

One problem with managing malodors emanating from a bowel movement is that the known techniques to deal with the malodors have been less than successful. As a result, there remains unmet needs of persons, for example consumers of bath tissue, to deal with malodor created during bowel movements.

Unfortunately, malodor control technologies typically cover up the malodor with a stronger scent and thus interfere with the scent of the perfumed or unperfumed situs that is treated with the malodor control technology. Thus, limited nature of the current malodor control technologies is extremely constraining. Thus what is needed is a broader palette of malodor control technologies so the perfume community can deliver the desired level of character in a greater number of situations/applications. Surprisingly, Applicants recognized that in addition to blocking a malodor's access to a sensory cell, in order to achieve the desired goal, a malodor control technology must leave such sensor cell open to other molecules, for example scent molecules. Thus, the malodor control technologies disclosed herein do not unduly interfere with the scent of the perfumed or unperfumed situs that is treated with the malodor control technology.

There is a need for a malodor technology for addressing malodors created during bowel movement events.

SUMMARY OF THE INVENTION

The present invention fulfills the need described above by providing a roll of fibrous structure, for example a roll of sanitary tissue product, such as a roll of toilet tissue comprising a core, wherein the core comprises one or more encapsulated malodor reduction compositions that can be activated before, during and/or after a bowel movement, methods of making such rolled fibrous structures. and methods of using such rolled fibrous structures. In one example, such malodor reduction compositions do not unduly interfere with the scent of the perfumed or unperfumed fibrous structure that is treated with the malodor reduction composition.

One solution to the problem described above is a roll of fibrous structure, for example a roll of sanitary tissue product, such as a roll of toilet tissue comprising a core, wherein the core comprises one or more encapsulated malodor reduction compositions that can be activated before, during and/or after a bowel movement, methods of making such rolled fibrous structures. and methods of using such rolled fibrous structures.

In one example of the present invention, a roll of fibrous structure comprising a core upon which the fibrous structure is convolutely wound, wherein the core comprises one or more encapsulated malodor reduction compositions, for example wherein one or more of the encapsulated malodor reduction composition is present on an exposed surface of the core, such as the surface of the core opposition the surface the fibrous structure is in contact with, wherein at least one of the malodor compositions comprises one or more carrier materials, for example one or more carrier materials selected from the group consisting of: polyacrylate, melamine, wax, cyclodextrin, bulk starch, cyclic(cyclodextrin), helical starch, and mixtures thereof, and one or more malodor reduction materials associated with the carrier material, is provided.

The present invention provides a roll of fibrous structure, for example a roll of sanitary tissue product, such as a roll of toilet tissue comprising a core, wherein the core comprises one or more encapsulated malodor reduction compositions, methods of making such fibrous structures. and methods of using such fibrous structures.

DETAILED DESCRIPTION OF THE INVENTION

As used herein "MORV" is the calculated malodor reduction value for a subject material. A material's MORV indicates such material's ability to decrease or even eliminate the perception of one or more malodors. For purposes of the present application, a material's MORV is calculated in accordance with method found in the test methods section of the present application.

"Malodor reduction composition" as used herein means a malodor reduction material in association with a carrier material, such as a cyclodextrin, for example a β-cyclodextrin, bulk starch, for example to encapsulate bulk oil, cyclic (cyclodextrin), helical starch/polysaccharides that enable molecular complexation, for example amylose, and mixtures thereof.

"Encapsulated malodor reduction composition" as used herein means a malodor reduction composition that is encapsulated in a shell, for example a polyacrylate shell, that is capable of rupturing upon a force, for example friction during dispensing of the fibrous structure from the roll as the core makes contact with a holder, for example a spindle, contacting one or more of the encapsulated malodor reduction composition thereby releasing at least a portion, for example all, of the malodor reduction composition from the encapsulate.

"Sanitary tissue product" or "tissue product" as used herein means a wiping implement for post-urinary and/or post-bowel movement cleaning (toilet tissue products), for otorhinolaryngological discharges (facial tissue products) and/or multi-functional absorbent and cleaning uses (absorbent towels such as paper towel products and/or wipe products). The sanitary tissue products of the present invention may comprise one or more fibrous structures and/or finished fibrous structures, traditionally, but not necessarily, comprising cellulose fibers.

The term "tissue-towel paper product" refers to products comprising paper tissue or paper towel technology in general, including, but not limited to, conventional felt-pressed or conventional wet-pressed tissue paper, pattern densified tissue paper, starch substrates, and high bulk, uncompacted tissue paper. Non-limiting examples of tissue-towel paper products include towels, facial tissue, bath tissue, table napkins, and the like.

As used herein, "malodor" refers to compounds generally offensive or unpleasant to most people, such as the complex odors associated with bowel movements.

As used herein, "odor blocking" refers to the ability of a compound to dull the human sense of smell.

As used herein, the terms "a" and "an" mean "at least one".

As used herein, the terms "include", "includes" and "including" are meant to be non-limiting.

As used herein, the term "perfume" does not include malodor reduction materials. Thus, the perfume portion of a composition does not include, when determining the perfume's composition, any malodor reduction materials found in the composition as such malodor reduction materials are described herein. In short, if a material has a malodor reduction value "MORV" that is within the range of the MORV recited in the subject claim, such material is a malodor reduction material for purposes of such claim.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Encapsulated Malodor Reduction Composition

An encapsulated malodor reduction composition is an encapsulate formed by a shell, for example a polymer shell, such as polyacrylate, that is capable of containing a malodor reduction composition comprising one or more malodor reduction materials, and then releasing the malodor reduction composition upon rupturing.

An encapsulated malodor reduction composition may be made from one or more malodor reduction materials, for example a combination of malodoer reduction materials. The malodor reduction material and/or malodor reduction material combinations may be specifically targeted to the malodor(s) for which the aim is to reduce and/or eliminate through mechanisms of masking, neutralization, elimination—one, a combination, or all of the mechanisms can be used to obtain the best results. The encapsulated malodor reduction composition may itself provide a signature fragrance and/or an additional signature olfactory freshness indicator can be incorporated.

Malodor Reduction Materials

A non-limiting set of suitable malodor reduction materials are provided in the tables below. For ease of use, each material in Tables 1-3 is assigned a numerical identifier which is found in the column for each table that is designated Number. Table 4 is a subset of Table 1, Table 5 is a subset of Table 2 and Table 6 is a subset of Table 3 and there for Tables 4, 5 and 6 each use the same numerical identifier as found, respectively, in Tables 1-3.

Codes
A=Vapor Pressure>0.1 torr
B=Vapor Pressure is between 0.01 torr and 0.1 torr
C=Log P<3
D=Log P>3
E=Probability of Ingredient Color Instability=0%
F=Probability of Ingredient Color Instability<71%
G=Odor Detection Threshold less than p.ol=8
H=Odor Detection Threshold greater than p.ol=8
I=Melamine formaldehyde PMC Headspace Response Ratio greater than or equal to 10
J=Melamine formaldehyde PMC leakage less than or equal to 5%
K=Log of liquid dish neat product liquid-air partition coefficient greater than or equal to −7
L=Log of liquid dish neat product liquid-air partition coefficient greater than or equal to −5

TABLE 1

List of materials with at least one MORV from 1 to 5

| Number | Material Name | CAS Number | Comment Code |
|---|---|---|---|
| 1 | 2-ethylhexyl (Z)-3-(4-methoxyphenyl)acrylate | 5466-77-3 | DEFHJ |
| 2 | 2,4-dimethyl-2-(5,5,8,8-tetramethyl-5,6,7,8-tetrahydronaphthalen-2-yl)-1,3-dioxolane | 131812-67-4 | DFHJ |
| 3 | 1,1-dimethoxynon-2-yne | 13257-44-8 | ACEFHJK |
| 4 | para-Cymen-8-ol | 1197-01-9 | BCGIJK |
| 7 | 3-methoxy-7,7-dimethyl-10-methylenebicyclo[4.3.1]decane | 216970-21-7 | BDEFHJK |
| 9 | Methoxycyclododecane | 2986-54-1 | DEFHJK |
| 10 | 1,1-dimethoxycyclododecane | 950-33-4 | DEFHJK |
| 11 | (Z)-tridec-2-enenitrile | 22629-49-8 | DEFHJK |
| 13 | Oxybenzone | 131-57-7 | DEFGJ |
| 14 | Oxyoctaline formate | 65405-72-3 | DFHJK |
| 16 | 4-methyl-1-oxaspiro[5.5]undecan-4-ol | 57094-40-3 | CFGIJK |
| 17 | 7-methyl-2H-benzo[b][1,4]dioxepin-3(4H)-one | 28940-11-6 | CGIK |
| 18 | 1,8-dioxacycloheptadecan-9-one | 1725-01-5 | DGJ |
| 21 | 4-(tert-pentyl)cyclohexan-1-one | 16587-71-6 | ADFGIJKL |
| 22 | o-Phenyl anisol | 86-26-0 | DEFHJK |
| 23 | 3a,5,6,7,8,8b-hexahydro-2,2,6,6,7,8,8-heptamethyl-4H-indeno(4,5-d)-1,3-dioxole | 823178-41-2 | DEFHJK |
| 25 | 7-isopropyl-8,8-dimethyl-6,10-dioxaspiro[4.5]decane | 62406-73-9 | BDEFHIJK |
| 28 | Octyl 2-furoate | 39251-88-2 | DEFHJK |
| 29 | Octyl acetate | 112-14-1 | BDEFHJKL |
| 30 | octanal propylene glycol acetal | 74094-61-4 | BDEFHJKL |
| 31 | Octanal | 124-13-0 | ACHIKL |
| 32 | Octanal dimethyl acetal | 10022-28-3 | ACEFGJKL |
| 33 | Myrcene | 123-35-3 | ADEFGIKL |
| 34 | Myrcenol | 543-39-5 | BCEFGIJK |
| 35 | Myrcenyl acetate | 1118-39-4 | ADEFGJK |
| 36 | Myristaldehyde | 124-25-4 | DFHJK |
| 37 | Myristicine | 607-91-0 | CGJK |
| 38 | Myristyl nitrile | 629-63-0 | DEFHJK |

TABLE 1-continued

List of materials with at least one MORV from 1 to 5

| Number | Material Name | CAS Number | Comment Code |
|---|---|---|---|
| 39 | 2,2,6,8-tetramethyl-1,2,3,4,4a,5,8,8a-octahydronaphthalen-1-ol | 103614-86-4 | DEFHIJ |
| 42 | Ocimenol | 5986-38-9 | BCHIJK |
| 43 | Ocimenol | 28977-58-4 | BCHIJK |
| 47 | Nopyl acetate | 128-51-8 | DEFHJK |
| 48 | Nootkatone | 4674-50-4 | DHJK |
| 49 | Nonyl alcohol | 143-08-8 | BDEFGIJKL |
| 50 | Nonaldehyde | 124-19-6 | ADHIKL |
| 52 | 12-methyl-14-tetradec-9-enolide | 223104-61-8 | DFHJK |
| 57 | N-ethyl-p-menthane-3-carboxamide | 39711-79-0 | DEFGIJK |
| 61 | 1-(3-methylbenzofuran-2-yl)ethan-1-one | 23911-56-0 | CEFHIK |
| 62 | 2-methoxynaphthalene | 93-04-9 | BDEFHK |
| 63 | Nerolidol | 7212-44-4 | DEFHJK |
| 64 | Nerol | 106-25-2 | BCHIK |
| 65 | 1-ethyl-3-methoxytricyclo[2.2.1.02,6]heptane | 31996-78-8 | ACEFHIJKL |
| 67 | Methyl (E)-non-2-enoate | 111-79-5 | ADEFHJKL |
| 68 | 10-isopropyl-2,7-dimethyl-1-oxaspiro[4.5]deca-3,6-diene | 89079-92-5 | BDEFHIJK |
| 69 | 2-(2-(4-methylcyclohex-3-en-1-yl)propyl)cyclopentan-1-one | 95962-14-4 | DHJK |
| 70 | Myrtenal | 564-94-3 | ACFHIJKL |
| 71 | (E)-4-(2,2,3,6-tetramethylcyclohexyl)but-3-en-2-one | 54992-90-4 | BDEFHIJK |
| 74 | Myraldyl acetate | 53889-39-7 | DHJK |
| 75 | Musk tibetine | 145-39-1 | DHIJ |
| 76 | 1,7-dioxacycloheptadecan-8-one | 3391-83-1 | DGJ |
| 77 | Musk ketone | 81-14-1 | DHJ |
| 78 | Musk ambrette | 83-66-9 | DHIJ |
| 79 | 3-methylcyclopentadecan-1-one | 541-91-3 | DEFHJK |
| 80 | (E)-3-methylcyclopentadec-4-en-1-one | 82356-51-2 | DHJK |
| 82 | 3-methyl-4-phenylbutan-2-ol | 56836-93-2 | BCEFHIK |
| 83 | 1-(4-isopropylcyclohexyl)ethan-1-ol | 63767-86-2 | BDEFHIJK |
| 85 | Milk Lactone | 72881-27-7 | DEFHJK |
| 91 | Methyl octine carbonate | 111-80-8 | BDEFHKL |
| 92 | Methyl octyl acetaldehyde | 19009-56-4 | ADFHJKL |
| 93 | 6,6-dimethoxy-2,5,5-trimethylhex-2-ene | 67674-46-8 | ACHIJKL |
| 98 | Methyl phenylethyl carbinol | 2344-70-9 | BCEFHIK |
| 100 | Methyl stearate | 112-61-8 | DEFHJ |
| 101 | Methyl nonyl acetaldehyde dimethyl acetal | 68141-17-3 | BDEFHJK |
| 102 | Methyl nonyl ketone | 112-12-9 | BDFHJKL |
| 103 | Methyl nonyl acetaldehyde | 110-41-8 | BDFHJK |
| 104 | Methyl myristate | 124-10-7 | DEFHJK |
| 105 | Methyl linoleate | 112-63-0 | DEFHJ |
| 106 | Methyl lavender ketone | 67633-95-8 | CFHJK |
| 108 | Methyl isoeugenol | 93-16-3 | ACEFHK |
| 109 | Methyl hexadecanoate | 112-39-0 | DEFHJK |
| 110 | Methyl eugenol | 93-15-2 | ACEFHK |
| 112 | Methyl epijasmonate | 1211-29-6 | CHJK |
| 113 | Methyl dihydrojasmonate | 24851-98-7 | DFHJK |
| 114 | Methyl diphenyl ether | 3586-14-9 | DEFHJK |
| 117 | Methyl cinnamate | 103-26-4 | BCEFHK |
| 119 | Methyl chavicol | 140-67-0 | ADEFHK |
| 120 | Methyl beta-naphthyl ketone | 93-08-3 | CEFHK |
| 122 | Methyl 2-octynoate | 111-12-6 | ACEFHKL |
| 123 | Methyl alpha-cyclogeranate | 28043-10-9 | ACHIJKL |
| 126 | Methoxycitronellal | 3613-30-7 | ACFGJK |
| 128 | Menthone 1,2-glycerol ketal (racemic) | 67785-70-0 | CEFHJ |
| 130 | Octahydro-1H-4,7-methanoindene-1-carbaldehyde | 30772-79-3 | BCFHIJKL |
| 134 | 3-(3-(tert-butyl)phenyl)-2-methylpropanal | 62518-65-4 | BDHJK |
| 135 | (E)-4-(4,8-dimethylnona-3,7-dien-1-yl)pyridine | 38462-23-6 | DEFHJK |
| 137 | (E)-trideca-3,12-dienenitrile | 134769-33-8 | DEFHJK |
| 140 | 2,2-dimethyl-3-(m-tolyl)propan-1-ol | 103694-68-4 | CEFHJK |
| 141 | 2,4-dimethyl-4,4a,5,9b-tetrahydroindeno[1,2-d][1,3]dioxine | 27606-09-3 | CEFHJK |
| 142 | Maceal | 67845-30-1 | BDFHJK |
| 143 | 4-(4-hydroxy-4-methylpentyl)cyclohex-3-ene-1-carbaldehyde | 31906-04-4 | CHJ |
| 145 | 1-Limonene | 5989-54-8 | ADEFGIJKL |
| 146 | (Z)-3-hexen-1-yl-2-cyclopenten-1-one | 53253-09-1 | BDHK |
| 148 | Linalyl octanoate | 10024-64-3 | DEFHJ |
| 149 | Linalyl isobutyrate | 78-35-3 | BDHJK |
| 152 | Linalyl benzoate | 126-64-7 | DFHJ |
| 153 | Linalyl anthranilate | 7149-26-0 | DFHJ |
| 155 | Linalool oxide (furanoid) | 60047-17-8 | BCHIJK |
| 156 | linalool oxide | 1365-19-1 | CGIJK |
| 158 | (2Z,6E)-3,7-dimethylnona-2,6-dienenitrile | 61792-11-8 | BDEFHJK |
| 159 | 3-(4-methylcyclohex-3-en-1-yl)butanal | 6784-13-0 | ACFHIJK |
| 161 | (2,5-dimethyl-1,3-dihydroinden-2-yl)methanol | 285977-85-7 | CEFHJK |
| 162 | 3-(4-(tert-butyl)phenyl)-2-methylpropanal | 80-54-6 | BDHJK |
| 167 | (E)-1-(1-methoxypropoxy)hex-3-ene | 97358-54-8 | ACEFGJKL |
| 168 | Leaf acetal | 88683-94-7 | ACEFGJKL |
| 170 | 1-Carveol | 2102-58-1 | BCHIJK |
| 174 | Lauryl alcohol | 112-53-8 | DEFGJK |
| 175 | Lauryl acetate | 112-66-3 | DEFHJK |
| 176 | Lauric acid | 143-07-7 | DEFHJ |
| 177 | Lactojasmone | 7011-83-8 | BDEFHIJKL |
| 178 | Lauraldehyde | 112-54-9 | BDFHJK |
| 179 | 3,6-dimethylhexahydrobenzofuran-2(3H)-one | 92015-65-1 | BCEFHIJKL |
| 182 | 4-(1-ethoxyvinyl)-3,3,5,5-tetramethylcyclohexan-1-one | 36306-87-3 | BDFHIJK |
| 183 | Khusimol | 16223-63-5 | CEFHJK |
| 184 | 5-(sec-butyl)-2-(2,4-dimethylcyclohex-3-en-1-yl)-5-methyl-1,3-dioxane | 117933-89-8 | DEFHJ |
| 185 | (1-methyl-2-((1,2,2-trimethylbicyclo[3.1.0]hexan-3-yl)methyl)cyclopropyl)methanol | 198404-98-7 | DEFHJK |
| 186 | 2-propylheptanenitrile | 208041-98-9 | ADEFHIJKL |
| 187 | (E)-6-(pent-3-en-1-yl)tetrahydro-2H-pyran-2-one | 32764-98-0 | BCFHIKL |
| 189 | 2-hexylcyclopentan-1-one | 13074-65-2 | BDFHJKL |
| 190 | 2-methyl-4-phenyl-1,3-dioxolane | 33941-99-0 | BCEFGIK |
| 192 | 2,6,9,10-tetramethyl-1-oxaspiro(4.5)deca-3,6-diene | 71078-31-4 | BDEFHIJK |
| 193 | Isopulegol | 89-79-2 | BCEFHIJKL |
| 195 | Isopropyl palmitate | 142-91-6 | DEFHJ |
| 196 | Isopropyl myristate | 110-27-0 | DEFHJK |
| 197 | Isopropyl dodecanoate | 10233-13-3 | DEFHJK |
| 199 | Isopimpinellin | 482-27-9 | CFGJ |
| 206 | Iso3-methylcyclopentadecan-1-one | 3100-36-5 | DEFGJK |
| 208 | Isomenthone | 491-07-6 | ADEFGIJKL |
| 209 | Isojasmone | 95-41-0 | BDFHJKL |
| 210 | Isomenthone | 36977-92-1 | ADEFGIJKL |
| 211 | Isohexenyl cyclohexenyl carboxaldehyde | 37677-14-8 | DFHJK |
| 212 | Isoeugenyl benzyl ether | 120-11-6 | DFHJ |
| 215 | 1-((2S,3S)-2,3,8,8-tetramethyl-1,2,3,4,5,6,7,8-octahydronaphthalen-2-yl)ethan-1-one | 54464-57-2 | DHJK |
| 218 | Isocyclocitral | 1335-66-6 | ACFHIJKL |
| 221 | Isobutyl quinoline | 65442-31-1 | DEFHJK |
| 227 | Isobornylcyclohexanol | 68877-29-2 | DEFHJK |
| 228 | Isobornyl propionate | 2756-56-1 | BDEFHIJK |
| 229 | Isobornyl isobutyrate | 85586-67-0 | BDEFHIJK |
| 230 | Isobornyl cyclohexanol | 66072-32-0 | DEFHJK |
| 231 | Isobornyl acetate | 125-12-2 | ADEFHIJKL |
| 233 | Isobergamate | 68683-20-5 | DEFHJK |
| 234 | Isoamyl undecylenate | 12262-03-2 | DEFHJK |
| 238 | Isoamyl laurate | 6309-51-9 | DEFHJK |
| 242 | Isoambrettolide | 28645-51-4 | DGJ |
| 243 | Irisnitrile | 29127-83-1 | ADEFHKL |
| 244 | Indolene | 68527-79-7 | DEFHJ |
| 246 | Indol/Hydroxycitronellal Schiff base | 67801-36-9 | DEFHJ |

TABLE 1-continued

List of materials with at least one MORV from 1 to 5

| Number | Material Name | CAS Number | Comment Code |
|---|---|---|---|
| 247 | 4,4a,5,9b-tetrahydroindeno[1,2-d][1,3]dioxine | 18096-62-3 | BCEFGJK |
| 249 | Hydroxy-citronellol | 107-74-4 | CEFGIJK |
| 252 | 2-cyclododecylpropan-1-ol | 118562-73-5 | DEFHJK |
| 253 | Hydrocitronitrile | 54089-83-7 | CEFHJK |
| 254 | Hydrocinnamyl alcohol | 122-97-4 | BCEFHIK |
| 256 | Hydratropaldehyde dimethyl acetal | 90-87-9 | ACEFHJK |
| 259 | 5-ethyl-4-hydroxy-2-methylfuran-3(2H)-one | 27538-09-6 | CFGIK |
| 260 | 2,3-dihydro-3,3-dimethyl-1H-indene-5-propanal | 173445-44-8 | DHJK |
| 261 | 3-(3,3-dimethyl-2,3-dihydro-1H-inden-5-yl)propanal | 173445-65-3 | DHJK |
| 263 | Hexyl octanoate | 1117-55-1 | DEFHJK |
| 267 | Hexyl hexanoate | 6378-65-0 | DEFHJKL |
| 269 | Hexyl cinnamic aldehyde | 101-86-0 | DHJ |
| 271 | Hexyl benzoate | 6789-88-4 | DEFHJK |
| 274 | Hexenyl tiglate | 84060-80-0 | BDEFHJK |
| 276 | (E)-3,7-dimethylocta-2,6-dien-1-yl palmitate | 3681-73-0 | DEFHJ |
| 277 | Hexadecanolide | 109-29-5 | DEFGJK |
| 278 | 2-butyl-4,4,6-trimethyl-1,3-dioxane | 54546-26-8 | ADEFHIJKL |
| 280 | Ethyl (1R,2R,3R,4R)-3-isopropylbicyclo[2.2.1]hept-5-ene-2-carboxylate | 116126-82-0 | BDEFHIJK |
| 281 | 3a,4,5,6,7,7a-hexahydro-1H-4,7-methanoinden-6-yl acetate | 5413-60-5 | CEFGJK |
| 285 | 2-(1-(3,3-dimethylcyclohexyl)ethoxy)-2-methylpropyl propionate | 141773-73-1 | DEFHJ |
| 286 | Heliotropine diethyl acetal | 40527-42-2 | CEFGJ |
| 288 | Helional | 1205-17-0 | CHJK |
| 289 | (E)-oxacyclohexadec-13-en-2-one | 111879-80-2 | DGJK |
| 290 | Gyrane | 24237-00-1 | ADEFHIJKL |
| 292 | Guaiol | 489-86-1 | DEFHJK |
| 293 | 1-(2,6,6-trimethylcyclohex-2-en-1-yl)pentan-3-one | 68611-23-4 | DHJK |
| 294 | Ethyl 2-ethyl-6,6-dimethylcyclohex-2-ene-1-carboxylate | 57934-97-1 | BDEFHIJK |
| 295 | Germacrene B | 15423-57-1 | DEFHJK |
| 296 | Germacrene D | 23986-74-5 | DEFHJK |
| 300 | Geranyl phenylacetate | 102-22-7 | DFHJ |
| 301 | Geranyl phenyl acetate | 71648-43-6 | DFHJ |
| 303 | Geranyl linalool | 1113-21-9 | DFHJ |
| 307 | Geranyl cyclopentanone | 68133-79-9 | DHJK |
| 316 | gamma-Undecalactone (racemic) | 104-67-6 | DEFHJKL |
| 317 | gamma-Terpinyl acetate | 10235-63-9 | BDHJK |
| 318 | gamma-Terpineol | 586-81-2 | BCGIJK |
| 321 | gamma-Nonalactone | 104-61-0 | BCEFHIKL |
| 322 | gamma-Muurolene | 30021-74-0 | DEFHJKL |
| 323 | gamma-(E)-6-(pent-3-en-1-yl)tetrahydro-2H-pyran-2-one | 63095-33-0 | BCEFHKL |
| 324 | gamma-Ionone | 79-76-5 | BDEFHIJK |
| 325 | gamma-Himachalene | 53111-25-4 | BDEFHJKL |
| 328 | gamma-Gurjunene | 22567-17-5 | DEFHJKL |
| 329 | gamma-Eudesmol | 1209-71-8 | DFHJK |
| 330 | gamma-Dodecalactone | 2305-05-7 | DEFHJK |
| 331 | gamma-Damascone | 35087-49-1 | BDEFHIJK |
| 332 | gamma-Decalactone | 706-14-9 | BDEFHIJKL |
| 333 | gamma-Cadinene | 39029-41-9 | DEFHJKL |
| 334 | 1-(3,3-dimethylcyclohexyl)pent-4-en-1-one | 56973-87-6 | BDEFHJK |
| 335 | 4,6,6,7,8,8-hexamethyl-1,3,4,6,7,8-hexahydrocyclopenta[g]isochromene | 1222-05-5 | DEFHJK |
| 336 | Furfuryl octanoate | 39252-03-4 | DEFHJK |
| 338 | Furfuryl hexanoate | 39252-02-3 | CEFHJK |
| 339 | Furfuryl heptanoate | 39481-28-2 | CEFHJK |
| 342 | 2-methyldecanenitrile | 69300-15-8 | BDEFHJKL |
| 343 | 8,8-dimethyl-3a,4,5,6,7,7a-hexahydro-1H-4,7-methanoinden-6-yl propionate | 76842-49-4 | DEFHJK |
| 344 | Ethyl (3aR,4S,7R,7aR)-octahydro-3aH-4,7-methanoindene-3a-carboxylate | 80657-64-3 | DEFHIJK |
| 347 | Diethyl cyclohexane-1,4-dicarboxylate | 72903-27-6 | CEFHJK |
| 349 | (6-isopropyl-9-methyl-1,4-dioxaspiro[4.5]decan-2-yl)methanol | 63187-91-7 | CEFHJ |
| 350 | 2-isobutyl-4-methyltetrahydro-2H-pyran-4-ol | 63500-71-0 | BCEFHIJK |
| 352 | Undec-10-enenitrile | 53179-04-7 | BDEFHJK |
| 353 | (Z)-6-ethylideneoctahydro-2H-5,8-methanochromen-2-one | 69486-14-2 | CEFGJK |
| 356 | 3-(2-ethylphenyl)-2,2-dimethylpropanal | 67634-15-5 | BDHJK |
| 358 | (E)-4,8-dimethyldeca-4,9-dienal | 71077-31-1 | BDFHJK |
| 359 | (E)-4-((3aR,4R,7R,7aR)-1,3a,4,6,7,7a-hexahydro-5H-4,7-methanoinden-5-ylidene)-3-methylbutan-2-ol | 501929-47-1 | DEFHJK |
| 360 | 8,8-dimethyl-3a,4,5,6,7,7a-hexahydro-1H-4,7-methanoinden-6-yl acetate | 171102-41-3 | DEFHJK |
| 361 | 3-(4-ethylphenyl)-2,2-dimethylpropanenitrile | 134123-93-6 | DEFHJK |
| 362 | 2-heptylcyclopentan-1-one | 137-03-1 | DFHJKL |
| 363 | 1-ethoxyethoxy Cyclododecane | 389083-83-4 | DEFHJK |
| 364 | 3-cyclohexene-1-carboxylic acid, 2,6,6-trimethyl-, methyl ester | 815580-59-7 | ACHIJKL |
| 368 | Farnesyl acetate | 29548-30-9 | DEFHJK |
| 369 | Farnesol | 4602-84-0 | DEFHJK |
| 370 | Oxacyclohexadecan-2-one | 106-02-5 | DEFGJK |
| 371 | 1-cyclopentadec-4-en-1-one | 14595-54-1 | DEFGJK |
| 372 | 1-cyclopentadec-4-en-1-one | 35720-57-1 | DEFGJK |
| 373 | 2-methoxy-4-(4-methylenetetrahydro-2H-pyran-2-yl)phenol | 128489-04-3 | CGJ |
| 374 | Eugenyl acetate | 93-28-7 | CFHJK |
| 375 | Eugenol | 97-53-0 | CHIK |
| 377 | Ethylmethylphenylglycidate | 77-83-8 | CFHJK |
| 378 | Ethylene brassylate | 105-95-3 | DFGJ |
| 381 | Ethyl undecylenate | 692-86-4 | DEFHJK |
| 385 | Ethyl palmitate | 628-97-7 | DEFHJ |
| 386 | Ethyl nonanoate | 123-29-5 | BDEFHJKL |
| 388 | Ethyl myristate | 124-06-1 | DEFHJK |
| 390 | Ethyl linalool | 10339-55-6 | BCEFHJK |
| 391 | Ethyl laurate | 106-33-2 | DEFHJK |
| 394 | Ethyl hexyl ketone | 925-78-0 | ADFHIKL |
| 397 | Ethyl decanoate | 110-38-3 | DEFHJK |
| 398 | Ethyl gamma-Safranate | 35044-57-6 | ADHIJK |
| 407 | Ethyl 3-phenylglycidate | 121-39-1 | CGJK |
| 413 | 6-ethyl-2,10,10-trimethyl-1-oxaspiro[4.5]deca-3,6-diene | 79893-63-3 | BDEFHIJK |
| 414 | Elemol | 639-99-6 | DEFHJK |
| 415 | (2-(1-ethoxyethoxy)ethyl)benzene | 2556-10-7 | BCEFHJK |
| 416 | (E)-3-methyl-5-(2,2,3-trimethylcyclopent-3-en-1-yl)pent-4-en-2-ol | 67801-20-1 | DHJK |
| 417 | d-xylose | 58-86-6 | CGIJ |
| 418 | (E)-4-((3aS,7aS)-octahydro-5H-4,7-methanoinden-5-ylidene)butanal | 30168-23-1 | DFHJK |
| 421 | Dodecanal dimethyl acetal | 14620-52-1 | DEFHJK |
| 424 | d-Limonene | 5989-27-5 | ADEFGIJKL |
| 425 | Dipropylene Glycol | 25265-71-8 | CEFGIK |
| 426 | Dispirone | 83863-64-3 | BDEFHJK |
| 428 | Diphenyloxide | 101-84-8 | BDEFHK |
| 429 | Diphenylmethane | 101-81-1 | DEFGK |
| 432 | Dimethyl benzyl carbinyl butyrate | 10094-34-5 | DEFHJK |
| 436 | 2,6-dimethyloct-7-en-4-one | 1879-00-1 | ADEFHIJKL |
| 441 | Octahydro-1H-4,7-methanoinden-5-yl acetate | 64001-15-6 | DEFHJKL |
| 444 | Dihydrocarveol acetate | 20777-49-5 | BDEFHIJK |
| 445 | Dihydrocarveol | 619-01-2 | BCEFHIJKL |
| 449 | Dihydro Linalool | 18479-51-1 | BCEFGIJKL |
| 450 | Dihydro Isojasmonate | 37172-53-5 | DHJK |
| 453 | Dibutyl sulfide | 544-40-1 | ADEFHIKL |
| 457 | Dibenzyl | 103-29-7 | DEFGJK |
| 459 | delta-Undecalactone | 710-04-3 | DEFHJKL |
| 461 | delta-Elemene | 20307-84-0 | BDEFHJK |

TABLE 1-continued

List of materials with at least one MORV from 1 to 5

| Number | Material Name | CAS Number | Comment Code |
|---|---|---|---|
| 462 | delta-Guaiene | 3691-11-0 | DEFHJKL |
| 463 | delta-Dodecalactone | 713-95-1 | DEFHJK |
| 464 | delta-Decalactone | 705-86-2 | BDEFHIJKL |
| 465 | delta-Cadinene | 483-76-1 | DEFHJKL |
| 466 | delta-damascone | 57378-68-4 | ADHIJK |
| 467 | delta-Amorphene | 189165-79-5 | DEFHJKL |
| 468 | delta-3-Carene | 13466-78-9 | ADEFGIJKL |
| 470 | Decylenic alcohol | 13019-22-2 | BDEFHJK |
| 471 | Decyl propionate | 5454-19-3 | DEFHJK |
| 473 | Decanal diethyl acetal | 34764-02-8 | DEFHJK |
| 474 | Decahydro-beta-naphthol | 825-51-4 | BCEFGIK |
| 475 | 1-cyclohexylethyl (E)-but-2-enoate | 68039-69-0 | BDFHJK |
| 478 | 3-(4-isopropylphenyl)-2-methylpropanal | 103-95-7 | BDFHJK |
| 479 | Cyclotetradecane | 295-17-0 | DEFGJKL |
| 480 | Cyclopentadecanone | 502-72-7 | DEFGJK |
| 482 | Cyclohexyl salicylate | 25485-88-5 | DFGJ |
| 484 | 3a,4,5,6,7,7a-hexahydro-1H-4,7-methanoinden-6-yl butyrate | 113889-23-9 | DEFHJK |
| 485 | Cyclic ethylene dodecanedioate | 54982-83-1 | DFGJ |
| 486 | 8,8-dimethyl-1,2,3,4,5,6,7,8-octahydronaphtalene-2-carbaldehyde | 68991-97-9 | DHJK |
| 487 | 3a,4,5,6,7,7a-hexahydro-1H-4,7-methanoinden-5-yl isobutyrate | 67634-20-2 | DEFHJK |
| 488 | Curzerene | 17910-09-7 | DHJK |
| 491 | Cumic alcohol | 536-60-7 | CHIJK |
| 493 | Coumarone | 1646-26-0 | BCEFHIK |
| 497 | 2-(3-phenylpropyl)pyridine | 2110-18-1 | CEFHJK |
| 498 | Dodecanenitrile | 2437-25-4 | DEFHJK |
| 501 | (E)-cycloheptadec-9-en-1-one | 542-46-1 | DEFGJ |
| 502 | Citryl acetate | 6819-19-8 | DFHJK |
| 503 | Citrus Propanol | 15760-18-6 | CEFHIJK |
| 505 | Citronitrile | 93893-89-1 | CEFHJK |
| 519 | Citral propylene glycol acetal | 10444-50-5 | CEFHJK |
| 520 | Citral dimethyl acetal | 7549-37-3 | BCEFHJK |
| 521 | Citral diethyl acetal | 7492-66-2 | BDEFHJK |
| 524 | cis-Ocimene | 3338-55-4 | ADGIKL |
| 527 | cis-Limonene oxide | 13837-75-7 | ADEFGIJKL |
| 529 | Cis-iso-ambrettolide | 36508-31-3 | DGJ |
| 530 | cis-6-nonenol | 35854-86-5 | BCEFHIKL |
| 531 | cis-carveol | 1197-06-4 | BCHIJK |
| 532 | cis-4-Decen-1-al | 21662-09-9 | ADHKL |
| 534 | cis-3-hexenyl-cis-3-hexenoate | 61444-38-0 | BDEFHJK |
| 537 | cis-3-Hexenyl salicylate | 65405-77-8 | DEFGJ |
| 541 | Cis-3-hexenyl Benzoate | 25152-85-6 | DEFHJK |
| 544 | cis-3-Hexenyl 2-methylbutyrate | 53398-85-9 | ADEFHJKL |
| 546 | cis-3, cis-6-nonadienol | 53046-97-2 | ACEFHK |
| 548 | Cinnamyl propionate | 103-56-0 | DEFHJK |
| 550 | Cinnamyl isobutyrate | 103-59-3 | DEFHJK |
| 551 | Cinnamyl formate | 104-65-4 | BCEFHK |
| 552 | Cinnamyl cinnamate | 122-69-0 | DHJ |
| 553 | Cinnamyl acetate | 103-54-8 | BCEFHK |
| 555 | Cinnamic alcohol | 104-54-1 | BCEFHIK |
| 558 | Cetyl alcohol | 36653-82-4 | DEFHJ |
| 559 | (E)-1-(2,6,6-trimethylcyclohex-2-en-1-yl)hepta-1,6-dien-3-one | 79-78-7 | DHJK |
| 560 | 2-methyl-4-(2,6,6-trimethylcyclohex-1-en-1-yl)butanal | 65405-84-7 | DFHJK |
| 561 | (3aR,5aS,9aS,9bR)-3a,6,6,9a-tetramethyldodecahydronaphtho[2,1-b]furan | 3738-00-9 | DEFHJK |
| 562 | 1,6-dioxacycloheptadecan-7-one | 6707-60-4 | DGJ |
| 563 | 1-(6-(tert-butyl)-1,1-dimethyl-2,3-dihydro-1H-inden-4-yl)ethan-1-one | 13171-00-1 | DEFHJK |
| 565 | Cedryl methyl ether | 19870-74-7 | ADEFHJK |
| 566 | Cedryl formate | 39900-38-4 | BDEFHJK |
| 567 | Cedryl acetate | 77-54-3 | DEFHJK |
| 568 | (4Z,8Z)-1,5,9-trimethyl-13-oxabicyclo[10.1.0]trideca-4,8-diene | 71735-79-0 | DFHJK |
| 569 | Cedrol | 77-53-2 | DEFHJK |
| 570 | 5-methyl-1-(2,2,3-trimethylcyclopent-3-en-1-yl)-6-oxabicyclo[3.2.1]octane | 139539-66-5 | DEFHJK |
| 571 | 5-methyl-1-(2,2,3-trimethylcyclopent-3-en-1-yl)-6-oxabicyclo[3.2.1]octane | 426218-78-2 | DFHJ |
| 572 | 1,1,2,3,3-pentamethyl-1,2,3,5,6,7-hexahydro-4H-inden-4-one | 33704-61-9 | BDEFHIJK |
| 573 | Caryophyllene alcohol acetate | 32214-91-8 | DEFHJK |
| 574 | Caryolan-1-ol | 472-97-9 | DEFHJK |
| 577 | Carvyl acetate | 97-42-7 | BDHIJK |
| 578 | Caprylnitrile | 124-12-9 | ACEFGIKL |
| 580 | Caprylic alcohol | 111-87-5 | ACEFGIKL |
| 581 | Caprylic acid | 124-07-2 | BCEFHIK |
| 582 | Capric acid | 334-48-5 | DEFHJK |
| 584 | Capraldehyde | 112-31-2 | ADHKL |
| 586 | 3-(4-methoxyphenyl)-2-methylpropanal | 5462-06-6 | BCHJK |
| 587 | Camphorquinone | 10373-78-1 | ACEFGIJK |
| 589 | Camphene | 79-92-5 | ADEFGIJKL |
| 591 | Ethyl 2-methyl-4-oxo-6-pentylcyclohex-2-ene-1-carboxylate | 59151-19-8 | DHJ |
| 592 | Butylated hydroxytoluene | 128-37-0 | DEFGIJK |
| 594 | Butyl stearate | 123-95-5 | DEFHJ |
| 595 | Butyl butyryl lactate | 7492-70-8 | CEFGJK |
| 599 | Butyl 10-undecenoate | 109-42-2 | DEFHJK |
| 600 | 2-methyl-4-(2,2,3-trimethylcyclopent-3-en-1-yl)butan-1-ol | 72089-08-8 | DEFHJK |
| 601 | 3-(4-(tert-butyl)phenyl)propanal | 18127-01-0 | BDHJK |
| 603 | Bornyl isobutyrate | 24717-86-0 | BDEFHIJK |
| 604 | Bornyl acetate | 76-49-3 | ADEFHIJKL |
| 606 | 2-ethoxy-2,6,6-trimethyl-9-methylenebicyclo[3.3.1]nonane | 68845-00-1 | BDEFHJK |
| 607 | (ethoxymethoxy)cyclododecane | 58567-11-6 | DEFHJK |
| 608 | Bisabolene | 495-62-5 | DEFHJK |
| 609 | Bigarade oxide | 72429-08-4 | ADEFHJKL |
| 610 | beta-Vetivone | 18444-79-6 | DHJK |
| 611 | beta-Terpinyl acetate | 10198-23-9 | BDHJK |
| 612 | beta-Terpineol | 138-87-4 | BCGIJK |
| 613 | beta-Sinensal | 60066-88-8 | DHJK |
| 614 | beta-Sesquiphellandrene | 20307-83-9 | DEFHJK |
| 615 | beta-Selinene | 17066-67-0 | BDEFGJK |
| 616 | beta-Santalol | 77-42-9 | DEFHJK |
| 618 | beta-Pinene | 127-91-3 | ADEFGIJKL |
| 620 | beta-Naphthyl ethyl ether | 93-18-5 | BDEFHJK |
| 621 | beta-Patchoulline | 514-51-2 | BDEFGJKL |
| 624 | beta-Himachalene Oxide | 57819-73-5 | BDFHJK |
| 625 | beta-Himachalene | 1461-03-6 | DEFHJKL |
| 626 | beta-Guaiene | 88-84-6 | DEFHJKL |
| 627 | (2,2-dimethoxyethyl)benzene | 101-48-4 | DHJK |
| 628 | beta-Farnesene | 18794-84-8 | DEFHJK |
| 631 | beta-Copaene | 18252-44-3 | BDEFHJKL |
| 632 | beta-Cedrene | 546-28-1 | BDEFGJKL |
| 633 | beta-Caryophyllene | 87-44-5 | DEFHJKL |
| 635 | beta-Bisabolol | 15352-77-9 | DFHJK |
| 636 | Beta ionone epoxide | 23267-57-4 | BDEFHJK |
| 638 | Bergaptene | 484-20-8 | CGJ |
| 639 | Benzyl-tert-butanol | 103-05-9 | CEFGJK |
| 644 | Benzyl laurate | 140-25-0 | DEFHJ |
| 649 | Benzyl dimethyl carbinol | 100-86-7 | BCEFGIK |
| 650 | Benzyl cinnamate | 103-41-3 | DHJ |
| 653 | Benzyl benzoate | 120-51-4 | DHJ |
| 655 | Benzophenone | 119-61-9 | DEFHK |
| 658 | 7-isopentyl-2H-benzo[b][1,4]dioxepin-3(4H)-one | 362467-67-2 | DHJ |
| 659 | 2'-isopropyl-1,7,7-trimethylspiro[bicyclo[2.2.1]heptane-2,4'-[1,3]dioxane] | 188199-50-0 | DEFHJK |
| 660 | 4-(4-methylpent-3-en-1-yl)cyclohex-3-ene-1-carbonitrile | 21690-43-7 | DEFHJK |
| 661 | Aurantiol | 89-43-0 | DEFHJ |
| 663 | Anisyl phenylacetate | 102-17-0 | DFHJ |
| 668 | Methyl (E)-octa-4,7-dienoate | 189440-77-5 | ACEFHKL |
| 671 | Amyl Cinnamate | 3487-99-8 | DEFHJK |
| 673 | (3aR,5aS,9aS,9bR)-3a,6,6,9a-tetramethyldodecahydronaphtho[2,1-b]furan | 6790-58-5 | DEFHJK |

TABLE 1-continued

List of materials with at least one MORV from 1 to 5

| Number | Material Name | CAS Number | Comment Code |
|---|---|---|---|
| 674 | (4aR,5R,7aS,9R)-2,2,5,8,8,9a-hexamethyloctahydro-4H-4a,9-methanoazuleno[5,6-d][1,3]dioxole | 211299-54-6 | DEFHJK |
| 675 | 2,5,5-trimethyl-1,2,3,4,5,6,7,8-octahydronaphthalen-2-ol | 71832-76-3 | DEFHJK |
| 676 | 2,5,5-trimethyl-1,2,3,4,5,6,7,8-octahydronaphthalen-2-ol | 41199-19-3 | DEFHJK |
| 677 | 1-((2-(tert-butyl)cyclohexyl)oxy)butan-2-ol | 139504-68-0 | DEFHJK |
| 678 | (3S,5aR,7aS,11aS,11bR)-3,8,8,11a-tetramethyldodecahydro-5H-3,5a-epoxynaphtho[2,1-c]oxepine | 57345-19-4 | DEFHJ |
| 679 | 2,2,6,6,7,8,8-heptamethyldecahydro-2H-indeno[4,5-b]furan | 476332-65-7 | ADEFHJK |
| 680 | 2,2,6,6,7,8,8-heptamethyldecahydro-2H-indeno[4,5-b]furan | 647828-16-8 | ADEFHJK |
| 681 | Amber acetate | 37172-02-4 | BDEFHJK |
| 682 | Alpinofix ™ | 811436-82-5 | DEFHJ |
| 683 | alpha-Thujone | 546-80-5 | ADEFGIJKL |
| 684 | alpha-Vetivone | 15764-04-2 | DHJK |
| 686 | alpha-Terpinyl propionate | 80-27-3 | BDEFHJK |
| 691 | alpha-Sinensal | 17909-77-2 | DHJK |
| 692 | alpha-Selinene | 473-13-2 | BDEFHJK |
| 693 | alpha-Santalene | 512-61-8 | ADEFHJKL |
| 694 | alpha-Santalol | 115-71-9 | DEFHJK |
| 696 | alpha-Patchoulene | 560-32-7 | ADEFHJKL |
| 697 | alpha-neobutenone | 56973-85-4 | BDHJK |
| 698 | alpha-Muurolene | 10208-80-7 | DEFHJKL |
| 700 | alpha-methyl ionone | 127-42-4 | BDHJK |
| 702 | alpha-Limonene | 138-86-3 | ADEFGIJKL |
| 704 | alpha-Irone | 79-69-6 | BDHJK |
| 706 | alpha-Humulene | 6753-98-6 | DEFHJK |
| 707 | alpha-Himachalene | 186538-22-7 | BDEFHJK |
| 708 | alpha-Gurjunene | 489-40-7 | BDEFHJKL |
| 709 | alpha-Guaiene | 3691-12-1 | DEFHJKL |
| 710 | alpha-Farnesene | 502-61-4 | DEFHJK |
| 711 | alpha-Fenchene | 471-84-1 | ADEFGIJKL |
| 712 | alpha-Eudesmol | 473-16-5 | DEFHJK |
| 713 | alpha-Curcumene | 4176-17-4 | DEFHJK |
| 714 | alpha-Cubebene | 17699-14-8 | ADEFHJKL |
| 715 | alpha-Cedrene epoxide | 13567-39-0 | ADEFHJK |
| 716 | alpha-Cadinol | 481-34-5 | DEFHJK |
| 717 | alpha-Cadinene | 24406-05-1 | DEFHJKL |
| 718 | alpha-Bisabolol | 515-69-5 | DFHJK |
| 719 | alpha-bisabolene | 17627-44-0 | DEFHJK |
| 720 | alpha-Bergamotene | 17699-05-7 | BDEFHJKL |
| 721 | alpha-Amylcinnamyl alcohol | 101-85-9 | DEFHJ |
| 722 | alpha-Amylcinnamyl acetate | 7493-78-9 | DEFHJ |
| 723 | alpha-Amylcinnamaldehyde diethyl acetal | 60763-41-9 | DEFHJ |
| 724 | alpha-Amylcinnamaldehyde | 122-40-7 | DHJK |
| 725 | alpha-Amorphene | 23515-88-0 | DEFHJKL |
| 726 | alpha-Agarofuran | 5956-12-7 | BDEFHJK |
| 727 | 1-methyl-4-(4-methyl-3-penten-1-yl)-3-Cyclohexene-1-carboxaldehyde | 52475-86-2 | DFHJK |
| 730 | 1-Phenyl-2-pentanol | 705-73-7 | CEFHK |
| 731 | 1-Phenyl-3-methyl-3-pentanol | 10415-87-9 | CEFJK |
| 733 | 2,3,4-trimethoxy-benzaldehyde | 2103-57-3 | BCGI |
| 735 | 2,4,5-trimethoxy-benzaldehyde | 4460-86-0 | BCG |
| 736 | 2,4,6-trimethoxybenzaldehyde | 830-79-5 | BCGI |
| 738 | 2,4-Nonadienal | 6750-03-4 | ACHKL |
| 741 | 2,6,10-Trimethylundecanal | 105-88-4 | BDFGJK |
| 742 | alpha,4-Dimethyl benzenepropanal | 41496-43-9 | ACHJK |
| 746 | Allyl cyclohexyl propionate | 2705-87-5 | BDEFHJK |
| 748 | Allyl amyl glycolate | 67634-00-8 | BCEFGJK |
| 750 | Allo-aromadendrene | 25246-27-9 | BDEFHJKL |
| 752 | Aldehyde C-11 | 143-14-6 | ADHJK |
| 754 | Methyl (E)-2-(((3,5-dimethylcyclohex-3-en-1-yl)methylene)amino)benzoate | 94022-83-0 | DEFHJ |
| 757 | 2,6,10-trimethylundec-9-enal | 141-13-9 | BDFHJK |
| 758 | Acetoxymethyl-isolongifolene (isomers) | 59056-62-1 | BDEFHJK |
| 763 | Acetate C9 | 143-13-5 | BDEFHJKL |
| 764 | Acetarolle ™ | 744266-61-3 | DFHJK |
| 766 | Acetaldehyde phenylethyl propyl acetal | 7493-57-4 | CEFHJK |
| 767 | Acetaldehyde dipropyl acetal | 105-82-8 | ACEFGIKL |
| 768 | Acetaldehyde benzyl 2-methoxyethyl acetal | 7492-39-9 | BCEFHJK |
| 769 | (Z)-2-(4-methylbenzylidene)heptanal | 84697-09-6 | DHJ |
| 770 | 9-decenal | 39770-05-3 | ADHKL |
| 771 | 8-Hexadecenolide | 123-69-3 | DGJ |
| 772 | 7-Methoxycoumarin | 531-59-9 | CHK |
| 774 | 7-epi-alpha-Selinene | 123123-37-5 | BDEFHJK |
| 775 | 7-eip-alpha-Eudesmol | 123123-38-6 | DEFHJK |
| 776 | 7-Acetyl-1,1,3,4,4,6-hexamethyltetralin | 1506-02-1 | DEFHJ |
| 778 | 6-Isopropylquinoline | 135-79-5 | CEFHJK |
| 781 | 6,6-dimethyl-2-norpinene-2-propionaldehyde | 33885-51-7 | BCFHJK |
| 782 | 6,10,14-trimethyl-2-Pentadecanone | 502-69-2 | DEFHJK |
| 786 | 5-Isopropenyl-2-methyl-2-vinyltetrahydrofuran | 13679-86-2 | ACGIJKL |
| 788 | 5-Cyclohexadecenone | 37609-25-9 | DEFGJK |
| 791 | 4-Terpinenol | 562-74-3 | BCHIJK |
| 792 | 4-Pentenophenone | 3240-29-7 | BCEFHIK |
| 800 | 4-Carvomenthenol | 28219-82-1 | BCHIJK |
| 802 | 4,5,6,7-Tetrahydro-3,6-dimethylbenzofuran | 494-90-6 | BCEFHIJKL |
| 803 | 4-(p-Methoxyphenyl)-2-butanone | 104-20-1 | BCEFHJK |
| 804 | 3-Thujopsanone | 25966-79-4 | BDEFHJK |
| 805 | 3-Propylidenephthalide | 17369-59-4 | CEFHK |
| 806 | 3-Nonylacrolein | 20407-84-5 | BDFHJK |
| 807 | 3-Methyl-5-phenyl-1-pentanal | 55066-49-4 | BDFHJK |
| 814 | 3-Hexenyl isovalerate | 10032-11-8 | ADEFHJKL |
| 821 | 3,6-Dimethyl-3-octanyl acetate | 60763-42-0 | ADEFHIJKL |
| 824 | 3,4,5-trimethoxybenzaldehyde | 86-81-7 | BCGIJ |
| 826 | 3-(p-Isopropylphenyl)propionaldehyde | 7775-00-0 | BDFHJK |
| 827 | 2-Undecenenitrile | 22629-48-7 | BDEFHJK |
| 828 | 2-Undecenal | 2463-77-6 | ADHJK |
| 829 | 2-trans-6-trans-Nonadienal | 17587-33-6 | ACHKL |
| 831 | 2-Phenylethyl butyrate | 103-52-6 | DEFHJK |
| 833 | 2-Phenyl-3-(2-furyl)prop-2-enal | 57568-60-2 | CHJ |
| 834 | 2-Phenoxyethanol | 122-99-6 | BCEFGIK |
| 837 | 2-Nonen-1-al | 2463-53-8 | ADHKL |
| 839 | 2-Nonanol | 628-99-9 | BDEFGIKL |
| 840 | 2-Nonanone | 821-55-6 | ADFHIKL |
| 849 | 2-Isobutyl quinoline | 93-19-6 | CEFHJK |
| 850 | 2-Hexylidene cyclopentanone | 17373-89-6 | DFHJKL |
| 852 | 2-Heptyl tetrahydrofuran | 2435-16-7 | BDEFHJKL |
| 856 | 2-Decenal | 3913-71-1 | ADHKL |
| 864 | 2,6-Nonadienal | 26370-28-5 | ACHKL |
| 865 | 2,6-Nonadien-1-ol | 7786-44-9 | ACEFHK |
| 866 | 2,6-dimethyl-octanal | 7779-07-9 | ADFGIJKL |
| 868 | 1-Decanol | 112-30-1 | BDEFGJK |
| 869 | 1-Hepten-1-ol, 1-acetate | 35468-97-4 | ACEFHKL |
| 870 | 10-Undecen-1-ol | 112-43-6 | DEFHJK |
| 871 | 10-Undecenal | 112-45-8 | ADHJK |
| 872 | 10-epi-gamma-Eudesmol | 15051-81-7 | DFHJK |
| 873 | 1,8-Thiocineol | 68391-28-6 | ADEFHIJKL |
| 876 | 1,3,5-undecatriene | 16356-11-9 | ADEFHJKL |
| 877 | 1,2-Dihydrolinalool | 2270-57-7 | BCEFGIJKL |
| 878 | 1,3,3-trimethyl-2-norbornanyl acetate | 13851-11-1 | ADEFHIJKL |
| 879 | 1,1,2,3,3-Pentamethylindan | 1203-17-4 | ADHIJKL |
| 881 | (Z)-6,10-dimethylundeca-5,9-dien-2-yl acetate | 3239-37-0 | DEFHJK |
| 884 | (Z)-3-Dodecenal | 68141-15-1 | BCFHJK |
| 885 | (S)-gamma-Undecalactone | 74568-05-1 | DEFHJKL |
| 886 | (R)-gamma-Undecalactone | 74568-06-2 | DEFHJKL |
| 890 | (E)-6,10-dimethylundeca-5,9-dien-2-yl acetat | 3239-35-8 | DEFHJK |
| 892 | (2Z)-3-methyl-5-phenyl-2-Pentenenitrile | 53243-59-7 | DEFHJK |
| 893 | (2S,5S,6S)-2,6,10,10-tetramethyl-1-oxaspiro[4_5]decan-6-ol | 65620-50-0 | DFHIJK |
| 894 | (2E)-3-methyl-5-phenyl-2-pentenenitrile | 53243-60-0 | CEFHJK |

TABLE 1-continued

List of materials with at least one MORV from 1 to 5

| Number | Material Name | CAS Number | Comment Code |
|---|---|---|---|
| 897 | (+)-Dihydrocarveol | 22567-21-1 | BCEFHIJKL |
| 905 | Menthone | 89-80-5 | ADEFGIJKL |
| 908 | (R,E)-2-methyl-4-(2,2,3-trimethylcyclopent-3-en-1-yl)but-2-en-1-ol | 185068-69-3 | CHJK |
| 912 | 2-(8-isopropyl-6-methylbicyclo[2.2.2]oct-5-en-2-yl)-1,3-dioxolane | 68901-32-6 | DEFHJK |
| 913 | gamma-methyl ionone | 7388-22-9 | BDHIJK |
| 914 | 3-(3-isopropylphenyl)butanal | 125109-85-5 | BDHJK |
| 916 | 3-(1-ethoxyethoxy)-3,7-dimethylocta-1,6-diene | 40910-49-4 | BDEFHJK |
| 919 | 3a,4,5,6,7,7a-hexahydro-1H-4,7-methanoinden-6-yl propionate | 17511-60-3 | CEFHJK |
| 920 | Bulnesol | 22451-73-6 | DEFHJK |
| 922 | Benzyl phenylacetate | 102-16-9 | DHJ |
| 923 | Benzoin | 119-53-9 | CEFHJ |
| 924 | (E)-1,2,4-trimethoxy-5-(prop-1-en-1-yl)benzene | 2883-98-9 | BCFGJK |
| 925 | alpha,alpha,6,6-tetramethyl bicyclo[3.1.1]hept-2-ene-propanal | 33885-52-8 | BDFHJK |
| 926 | 7-epi-sesquithujene | 159407-35-9 | DEFHJKL |
| 927 | 5-Acetyl-1,1,2,3,3,6-hexamethylindan | 15323-35-0 | DEFHJK |
| 928 | 3-Methylphenethyl alcohol | 1875-89-4 | BCEFHIK |
| 929 | 3,6-Nonadien-1-ol | 76649-25-7 | ACEFHK |
| 930 | 2-Tridecenal | 7774-82-5 | BDFHJK |
| 933 | Patchouli alcohol | 5986-55-0 | DEFHJK |
| 937 | p-Cresyl isobutyrate | 103-93-5 | BDHJK |
| 939 | p-Cresyl n-hexanoate | 68141-11-7 | DEFHJK |
| 941 | 5-hexyl-4-methyldihydrofuran-2(3H)-one | 67663-01-8 | BDEFHIJKL |
| 942 | Ethyl (2Z,4E)-deca-2,4-dienoate | 3025-30-7 | BDEFHJK |
| 943 | Pelargene | 68039-40-7 | DEFHJK |
| 945 | 2-cyclohexylidene-2-phenylacetonitrile | 10461-98-0 | DFHJK |
| 946 | Perillaldehyde | 2111-75-3 | ACHIJK |
| 947 | Perillyl acetate | 15111-96-3 | DFHJK |
| 948 | Perillyl alcohol | 536-59-4 | CHIJK |
| 950 | (2-isopropoxyethyl)benzene | 68039-47-4 | ACEFHJKL |
| 951 | Ethyl (2Z,4E)-deca-2,4-dienoate | 313973-37-4 | BDEFHJK |
| 953 | (2-(cyclohexyloxy)ethyl)benzene | 80858-47-5 | DEFHJK |
| 954 | Phenethyl 2-methylbutyrate | 24817-51-4 | DEFHJK |
| 955 | Phenethyl alcohol | 60-12-8 | BCEFGIK |
| 959 | Phenethyl phenylacetate | 102-20-5 | DHJ |
| 962 | Phenoxanol | 55066-48-3 | DEFHJK |
| 965 | Phenyl benzoate | 93-99-2 | DFHJK |
| 967 | Phenyl ethyl benzoate | 94-47-3 | DHJ |
| 969 | Phenylacetaldehyde ethyleneglycol acetal | 101-49-5 | BCEFGIK |
| 973 | 2-(6,6-dimethylbicyclo[3.1.1]hept-2-en-2-yl)acetaldehyde | 30897-75-7 | ACFHIJKL |
| 974 | Pinocarveol | 5947-36-4 | BCEFGIJKL |
| 976 | Piperonyl acetone | 55418-52-5 | CEFGJ |
| 978 | 3a,4,5,6,7,7a-hexahydro-1H-4,7-methanoinden-6-yl pivalate | 68039-44-1 | DEFHJK |
| 980 | (4aR,8aS)-7-methyloctahydro-1,4-methanonaphthalen-6(2H)-one | 41724-19-0 | CEFGJKL |
| 982 | p-Menth-3-en-1-ol | 586-82-3 | BCGIJK |
| 985 | (E)-3,3-dimethyl-5-(2,2,3-trimethylcyclopent-3-en-1-yl)pent-4-en-2-ol | 107898-54-4 | DHJK |
| 988 | 1-methyl-4-(4-methylpent-3-en-1-yl)cyclohex-3-ene-1-carbaldehyde | 52474-60-9 | DFHJK |
| 993 | Propylene glycol | 57-55-6 | ACEFGIKL |
| 998 | p-Tolyl phenylacetate | 101-94-0 | DFHJ |
| 1000 | Ethyl 2,4,7-decatrienoate | 78417-28-4 | BDEFHJK |
| 1003 | 2-benzyl-4,4,6-trimethyl-1,3-dioxane | 67633-94-7 | DEFHJK |
| 1006 | 2,4-dimethyl-4-phenyltetrahydrofuran | 82461-14-1 | BDEFHJK |
| 1007 | (2R,4aR,8aR)-3',7'-dimethyl-3',4',4a,5',8',8a-hexahydro-1'H-spiro[oxirane-2,2'-[1,4]methanonaphthalene] | 41816-03-9 | DEFHJK |
| 1008 | (Z)-6-ethylideneoctahydro-2H-5,8-methanochromene | 93939-86-7 | BCEFHJKL |
| 1009 | 2-((S)-1-((S)-3,3-dimethylcyclohexyl)ethoxy)-2-oxoethyl propionate | 236391-76-7 | DFHJ |
| 1010 | Methyl 2,2-dimethyl-6-methylenecyclohexane-1-carboxylate | 81752-87-6 | ADHIJKL |
| 1012 | 2-methyl-5-phenylpentan-1-ol | 25634-93-9 | DEFHJK |
| 1016 | 4-methyl-2-phenyl-3,6-dihydro-2H-pyran | 60335-71-9 | BCEFGJK |
| 1020 | Sabinol | 471-16-9 | BCEFHIJKL |
| 1021 | Safrole | 94-59-7 | BCEFHK |
| 1022 | 2,2,7,9-tetramethylspiro(5.5)undec-8-en-1-one | 502847-01-0 | DHIJK |
| 1023 | 3-methyl-5-(2,2,3-trimethylcyclopent-3-en-1-yl)pentan-2-ol | 65113-99-7 | DEFHJK |
| 1024 | (Z)-2-ethyl-4-(2,2,3-trimethylcyclopent-3-en-1-yl)but-2-en-1-ol | 28219-61-6 | DEFHJK |
| 1025 | (E)-2-methyl-4-(2,2,3-trimethylcyclopent-3-en-1-yl)but-2-en-1-ol | 28219-60-5 | CHJK |
| 1026 | 5-methoxyoctahydro-1H-4,7-methanoindene-2-carbaldehyde | 86803-90-9 | CHJK |
| 1027 | 5-methoxyoctahydro-1H-4,7-methanoindene-2-carbaldehyde | 193425-86-4 | CHJK |
| 1028 | Sclareol | 515-03-7 | DEFHJ |
| 1029 | Sclareol oxide | 5153-92-4 | DEFHJK |
| 1031 | Selina-3,7(11)-diene | 6813-21-4 | DEFHJKL |
| 1032 | 2-(1-(3,3-dimethylcyclohexyl)ethoxy)-2-methylpropyl cyclopropanecarboxylate | 477218-42-1 | DEFHJ |
| 1033 | 3-(4-isobutylphenyl)-2-methylpropanal | 6658-48-6 | DHJK |
| 1035 | Spathulenol | 6750-60-3 | DEFHJK |
| 1036 | Spirambrene | 533925-08-5 | BCEFHJK |
| 1037 | Spirodecane | 6413-26-9 | BCEFGIJKL |
| 1038 | 1-(spiro[4.5]dec-7-en-7-yl)pent-4-en-1-one | 224031-70-3 | DGJK |
| 1042 | 2-(4-methylthiazol-5-yl)ethan-1-ol | 137-00-8 | CGIKL |
| 1043 | 2-(heptan-3-yl)-1,3-dioxolane | 4359-47-1 | ACEFHIJKL |
| 1045 | (Z)-dodec-4-enal | 21944-98-9 | BDFHJK |
| 1046 | tau-Cadinol | 5937-11-1 | DEFHJK |
| 1047 | tau-Muurolol | 19912-62-0 | DEFHJK |
| 1053 | Tetrahydrojasmone | 13074-63-0 | BDFHIJKL |
| 1057 | 2,6,10,10-tetramethyl-1-oxaspiro[4.5]dec-6-ene | 36431-72-8 | BDFHIJKL |
| 1059 | Thiomenthone | 38462-22-5 | BDEFHIJKL |
| 1060 | Thujopsene | 470-40-6 | BDEFGJKL |
| 1062 | Thymol methyl ether | 1076-56-8 | ADHIJKL |
| 1063 | 1-(2,2,6-trimethylcyclohexyl)hexan-3-ol | 70788-30-6 | DEFHJK |
| 1064 | trans,trans-2,4-Nonadienal | 5910-87-2 | ACHKL |
| 1065 | trans,trans-Farnesol | 106-28-5 | DEFHJK |
| 1066 | trans,cis-6-Nonadienal | 557-48-2 | ACHKL |
| 1067 | trans-2-Decenal | 3913-81-3 | ADHKL |
| 1070 | trans-2-Nonen-1-al | 18829-56-6 | ADHKL |
| 1072 | trans-3, cis-6-nonadienol | 56805-23-3 | ACEFHK |
| 1073 | trans-4-Decen-1-al | 65405-70-1 | ADHKL |
| 1075 | trans-ambrettolide | 51155-12-5 | DGJ |
| 1077 | trans-beta-ocimene | 13877-91-3 | ADGIKL |
| 1078 | trans-beta-Ocimene | 3779-61-1 | ADGIKL |
| 1082 | trans-Geraniol | 106-24-1 | BCHIK |
| 1083 | trans-Hedione | 2570-03-8 | DFHJK |
| 1085 | 7-(1,1-Dimethylethyl)-2H-1,5-benzodioxepin-3(4H)-one | 195251-91-3 | CEFHJ |
| 1089 | Tricyclone | 68433-81-8 | DEFHJK |
| 1090 | Tridecyl alcohol | 112-70-9 | DEFGJK |
| 1091 | Triethyl citrate | 77-93-0 | CEFGJ |
| 1093 | Methyl 2-((1-hydroxy-3-phenylbutyl)amino)benzoate | 144761-91-1 | DFHJ |

TABLE 1-continued

List of materials with at least one MORV from 1 to 5

| Number | Material Name | CAS Number | Comment Code |
|---|---|---|---|
| 1095 | 1-((2E,5Z,9Z)-2,6,10-trimethylcyclododeca-2,5,9-trien-1-yl)ethan-1-one | 28371-99-5 | DHJK |
| 1097 | Decahydro-2,6,6,7,8,8-hexamethyl-2h-indeno(4,5-b)furan | 338735-71-0 | BDEFHJK |
| 1099 | 13-methyl oxacyclopentadec-10-en-2-one | 365411-50-3 | DEFHJK |
| 1102 | Undecanal | 112-44-7 | BDHJK |
| 1104 | (E)-4-methyldec-3-en-5-ol | 81782-77-6 | BDEFHIJK |
| 1105 | Valencene | 4630-07-3 | BDEFHJK |
| 1107 | Valerianol | 20489-45-6 | DEFHJK |
| 1111 | Vanillin isobutyrate | 20665-85-4 | CHJ |
| 1113 | Vaniwhite | 5533-03-9 | CGIK |
| 1116 | (Z)-2-methyl-4-(2,6,6-trimethylcyclohex-2-en-1-yl)but-2-enal | 68555-62-4 | BDFHJK |
| 1117 | Methyl 2,4-dihydroxy-3,6-dimethylbenzoate | 4707-47-5 | CGIJ |
| 1120 | 1-methoxy-3a,4,5,6,7,7a-hexahydro-1H-4,7-methanoindene | 27135-90-6 | ACEFHJKL |
| 1121 | Methyl (Z)-2-((3-(4-(tert-butyl)phenyl)-2-methylpropylidene)amino)benzoate | 91-51-0 | DFHJ |
| 1125 | (Z)-hex-3-en-1-yl isobutyrate | 41519-23-7 | ADEFHJKL |
| 1126 | Vertacetal | 5182-36-5 | BCFHJK |
| 1129 | 1-((3R,3aR,7R,8aS)-3,6,8,8-tetramethyl-2,3,4,7,8,8a-hexahydro-1H-3a,7-methanoazulen-5-yl)ethan-1-one | 32388-55-9 | DHJK |
| 1131 | Methyl (Z)-2-(((2,4-dimethylcyclohex-3-en-1-yl)methylene)amino)benzoate | 68738-99-8 | DEFHJ |
| 1135 | Vetiverol | 89-88-3 | CEFHIJK |
| 1136 | Vetivert Acetate | 117-98-6 | DEFHJK |
| 1137 | Decahydro-3H-spiro[furan-2,5'-[4,7]methanoindene] | 68480-11-5 | DEFGJKL |
| 1138 | (2Z,6E)-nona-2,6-dienenitrile | 67019-89-0 | ACEFHKL |
| 1139 | (Z)-cyclooct-4-en-1-yl methyl carbonate | 87731-18-8 | BCHJKL |
| 1140 | (1aR,4S,4aS,7R,7aS,7bS)-1,1,4,7-tetramethyldecahydro-1H-cyclopropa[e]azulen-4-ol | 552-02-3 | DEFHJK |
| 1142 | 3,5,5,6,7,8,8-heptamethyl-5,6,7,8-tetrahydronaphthalene-2-carbonitrile | 127459-79-4 | DHJ |
| 1143 | (1S,2S,3S,5R)-2,6,6-trimethylspiro[bicyclo[3.1.1]heptane-3,1'-cyclohexan]-2'-en-4'-one | 133636-82-5 | DEFHJK |
| 1144 | 1',1',5',5'-tetramethylhexahydro-2'H,5'H-spiro[[1,3]dioxolane-2,8'-[2,4a]methanonaphthalene] | 154171-76-3 | DEFHJK |
| 1145 | 1',1',5',5'-tetramethylhexahydro-2'H,5'H-spiro[[1,3]dioxolane-2,8'-[2,4a]methanonaphthalene] K | 154171-77-4 | DEFHJK |
| 1146 | 4-(4-hydroxy-3-methoxyphenyl)butan-2-one | 122-48-5 | CEFGJ |
| 1147 | (1R,8aR)-4-isopropyl-1,6-dimethyl-1,2,3,7,8,8a-hexahydronaphthalene | 41929-05-9 | DEFHJKL |
| 1148 | 4,5-epoxy-4,11,11-trimethyl-8-methylenebicyclo(7.2.0)undecane | 1139-30-6 | DEFHJK |
| 1149 | 1,3,4,6,7,8alpha-hexahydro-1,1,5,5-tetramethyl-2H-2,4alpha-methanopthalen-8(5H)-one | 23787-90-8 | DEFHIJK |
| 1151 | 4,8-Dimethyl-1-(methylethyl)-7-oxabicyclo[4.3.0] nonane | TBD | BDEHJ |
| 1152 | 2,3-dihydro-1,1-dimethyl-1H-indene-ar-propanal | 300371-33-9 | DHIJK |

TABLE 2

List of materials with at least one MORV greater than 5 to 10

| Number | Material Name | CAS Number | Comment Code |
|---|---|---|---|
| 2 | 2,4-dimethyl-2-(5,5,8,8-tetramethyl-5,6,7,8-tetrahydronaphthalen-2-yl)-1,3-dioxolane | 131812-67-4 | DFHJ |
| 23 | 3a,5,6,7,8,8b-hexahydro-2,2,6,6,7,8,8-heptamethyl-4H-indeno(4,5-d)-1,3-dioxole | 823178-41-2 | DEFHJK |
| 141 | 2,4-dimethyl-4,4a,5,9b-tetrahydroindeno[1,2-d][1,3]dioxine | 27606-09-3 | CEFHJK |
| 185 | (1-methyl-2-((1,2,2-trimethylbicyclo[3.1.0]hexan-3-yl)methyl)cyclopropyl)methanol | 198404-98-7 | DEFHJK |
| 227 | Isobornylcyclohexanol | 68877-29-2 | DEFHJK |
| 230 | Isobornyl cyclohexanol | 66072-32-0 | DEFHJK |
| 246 | Indol/Hydroxycitronellal Schiff base | 67801-36-9 | DEFHJ |
| 248 | Hydroxymethyl isolongifolene | 59056-64-3 | DEFHJK |
| 343 | 8,8-dimethyl-3a,4,5,6,7,7a-hexahydro-1H-4,7-methanoinden-6-yl propionate | 76842-49-4 | DEFHJK |
| 359 | (E)-4-((3aR,4R,7R,7aR)-1,3a,4,6,7,7a-hexahydro-5H-4,7-methanoinden-5-ylidene)-3-methylbutan-2-ol | 501929-47-1 | DEFHJK |
| 565 | Cedryl methyl ether | 19870-74-7 | BDEFHJK |
| 631 | beta-Copaene | 18252-44-3 | BDEFHJKL |
| 659 | 2'-isopropyl-1,7,7-trimethylspiro[bicyclo[2.2.1]heptane-2,4'-[1,3]dioxane] | 869292-93-3 | BDEFHJK |
| 674 | (4aR,5R,7aS,9R)-2,2,5,8,8,9a-hexamethyloctahydro-4H-4a,9-methanoazuleno[5,6-d][1,3]dioxole | 211299-54-6 | DEFHJK |

TABLE 2-continued

List of materials with at least one MORV greater than 5 to 10

| Number | Material Name | CAS Number | Comment Code |
|---|---|---|---|
| 678 | (3S,5aR,7aS,11aS,11bR)-3,8,8,11a-tetramethyldodecahydro-5H-3,5a-epoxynaphtho[2,1-c]oxepine | 57345-19-4 | DEFHJ |
| 679 | 2,2,6,6,7,8,8-heptamethyldecahydro-2H-indeno[4,5-b]furan | 476332-65-7 | DEFHJK |
| 715 | alpha-Cedrene epoxide | 13567-39-0 | BDEFHJK |
| 758 | Acetoxymethyl-isolongifolene (isomers) | 59056-62-1 | DEFHJK |
| 1028 | Sclareol | 515-03-7 | DEFHJ |
| 1097 | Decahydro-2,6,6,7,8,8-hexamethyl-2h-indeno(4,5-b)furan | 338735-71-0 | DEFHJK |

TABLE 3

List of materials with at least one MORV from 0.5 to less than 1

| Number | Material Name | CAS Number | Comment Code |
|---|---|---|---|
| 12 | 1-ethoxy-4-(tert-pentyl)cyclohexane | 181258-89-9 | ADEFHJK |
| 19 | (3Z)-1-(2-buten-1-yloxy)-3-hexene | 888744-18-1 | ADEFHJKL |
| 20 | 4-(2-methoxypropan-2-yl)-1-methylcyclohex-1-ene | 14576-08-0 | ADHIJKL |
| 24 | O-Methyl linalool | 60763-44-2 | ADHIJKL |
| 26 | o-Methoxycinnamaldehyde | 1504-74-1 | ACHK |
| 27 | Octanal, 3,7-dimethyl- | 25795-46-4 | ADGIJKL |
| 53 | 3,3-Dimethyl-5(2,2,3-Trimethyl-3-Cyclopenten-1yl)-4-Penten-2-ol | 329925-33-9 | CEFHJ |
| 54 | n-Hexyl salicylate | 6259-76-3 | DEFHJ |
| 55 | n-Hexyl 2-butenoate | 19089-92-0 | ADEFHJKL |
| 59 | Neryl Formate | 2142-94-1 | BCEFHJK |
| 72 | Methyl-beta-ionone | 127-43-5 | DHJK |
| 73 | Myroxide | 28977-57-3 | ADGIJKL |
| 81 | (E)-3,7-dimethylocta-4,6-dien-3-ol | 18479-54-4 | BCEFGIJK |
| 84 | (Z)-hex-3-en-1-yl cyclopropanecarboxylate | 188570-78-7 | BCEFHIKL |
| 96 | Methyl phenyl carbinyl propionate | 120-45-6 | BCHJK |
| 97 | Methyl phenylacetate | 101-41-7 | ACEFHIKL |
| 107 | 2-methyl-6-oxaspiro[4.5]decan-7-one | 91069-37-3 | BCEFGIKL |
| 111 | Methyl geraniate | 2349-14-6 | BCHJKL |
| 115 | 2-ethoxy-4-(methoxymethyl)phenol | 5595-79-9 | CFGK |
| 116 | Methyl cyclopentylideneacetate | 40203-73-4 | ACEFHIKL |
| 125 | Methoxymelonal | 62439-41-2 | ACGIJK |
| 133 | ((1s,4s)-4-isopropylcyclohexyl)methanol | 13828-37-0 | BDEFHIJK |
| 147 | Linalyl propionate | 144-39-8 | BDFHJK |
| 150 | Linalyl formate | 115-99-1 | ACFHJK |
| 151 | Linalyl butyrate | 78-36-4 | BDEFHJK |
| 154 | Linalyl acetate | 115-95-7 | BDHJK |
| 157 | Linalool | 78-70-6 | BCEFGIJK |
| 163 | (Z)-hex-3-en-1-yl methyl carbonate | 67633-96-9 | ACEFGKL |
| 166 | Lepidine | 491-35-0 | BCEFHIKL |
| 169 | L-Carvone | 6485-40-1 | ACGIJKL |
| 181 | Khusinil | 75490-39-0 | DHJK |
| 191 | Isoraldeine | 1335-46-2 | BDHIJK |
| 194 | Isopropylvinylcarbinol | 4798-45-2 | ACGIKL |
| 198 | Isopropyl 2-methylbutyrate | 66576-71-4 | ACEFGIJKL |
| 201 | Isopentyrate | 80118-06-5 | ADEFGIJKL |
| 204 | Isononyl acetate | 40379-24-6 | BDEFHJKL |
| 205 | Isononanol | 27458-94-2 | BDEFGIKL |
| 213 | Isoeugenyl acetate | 93-29-8 | CFHJK |
| 214 | Isoeugenol | 97-54-1 | CEFHIK |
| 232 | Isoborneol | 124-76-5 | ACEFHIJKL |
| 237 | Isoamyl octanoate | 2035-99-6 | DEFHJK |
| 239 | Isoamyl isobutyrate | 2050-01-3 | ACEFGIJKL |
| 255 | Hydrocinnamic acid | 501-52-0 | CEFHIK |
| 258 | Hydratopic alcohol | 1123-85-9 | BCEFHIK |
| 264 | Hexyl propanoate | 2445-76-3 | ADEFHIKL |
| 270 | Hexyl butyrate | 2639-63-6 | BDEFHJKL |
| 273 | Hexyl 2-methylbutanoate | 10032-15-2 | BDEFHJKL |
| 275 | Hexyl 2-furoate | 39251-86-0 | DEFHJK |
| 282 | Heptyl alcohol | 111-70-6 | ACEFGIKL |
| 283 | Heptyl acetate | 112-06-1 | ADEFHKL |
| 284 | Heptaldehyde | 111-71-7 | ACHIKL |
| 287 | Heliotropin | 120-57-0 | BCGIK |
| 302 | Geranyl nitrile | 5146-66-7 | BCEFHKL |
| 306 | Geranyl formate | 105-86-2 | BCEFHJK |
| 308 | Geranyl caprylate | 51532-26-4 | DEFHJ |
| 310 | Geranyl benzoate | 94-48-4 | DFHJ |
| 312 | Geranial | 141-27-5 | ACHIKL |
| 314 | N,2-dimethyl-N-phenylbutanamide | 84434-18-4 | BCEFHJK |
| 319 | gamma-Terpinene | 99-85-4 | ADEFGIJKL |
| 346 | 2-(sec-butyl)cyclohexan-1-one | 14765-30-1 | ADFHIKL |
| 354 | 3-(2-ethylphenyl)-2,2-dimethylpropanal | 67634-14-4 | BDHJK |
| 355 | 2-(tert-butyl)cyclohexyl ethyl carbonate | 67801-64-3 | BDFHJK |
| 365 | 2-(tert-butyl)cyclohexyl ethyl carbonate | 81925-81-7 | ACFHIKL |
| 366 | Fenchyl alcohol | 1632-73-1 | ACGIJKL |
| 376 | Eucalyptol | 470-82-6 | ADEFGIJKL |
| 379 | Ethyl vanillin acetate | 72207-94-4 | CHJ |
| 387 | Ethyl octanoate | 106-32-1 | BDEFHJKL |
| 400 | Ethyl cinnamate | 103-36-6 | BCEFHK |
| 412 | Ethyl 2-(cyclohexyl)propionate | 2511-00-4 | BDFHIJKL |
| 419 | d-p-8(9)-Menthen-2-one | 5524-05-0 | ACGIJKL |
| 420 | 4-methyl-2-phenyltetrahydro-2H-pyran | 94201-73-7 | BDEFHJK |
| 437 | Dihydromyrcenol | 18479-58-8 | ADEFGIJK |
| 438 | Dihydrojasmone | 1128-08-1 | BCFHIJKL |
| 439 | Dihydroisophorone | 873-94-9 | ACEFGIJKL |
| 440 | Dihydroeugenol | 2785-87-7 | CEFHIJK |
| 442 | Dihydrocoumarin | 119-84-6 | BCGIKL |
| 443 | Dihydrocarvone | 7764-50-3 | ACGIJKL |
| 447 | Dihydro-alpha-terpinyl acetate | 80-25-1 | BDEFHIJKL |
| 448 | Dihydro-alpha-ionone | 31499-72-6 | BDHIJK |
| 454 | Dibenzyl ether | 103-50-4 | DEFHJK |
| 455 | Dibutyl o-phthalate | 84-74-2 | DEFHJ |
| 469 | 2-pentylcyclopentan-1-one | 4819-67-4 | BDFHIKL |
| 472 | Decyl anthranilate | 18189-07-6 | DEFHJ |
| 477 | Methyl (1s,4s)-1,4-dimethylcyclohexane-1-carboxylate | 23059-38-3 | ADEFHIJKL |
| 481 | Cyclohexylethyl acetate | 21722-83-8 | BDEFHJKL |
| 492 | Creosol | 93-51-6 | BCHIK |
| 495 | Cosmene | 460-01-5 | ADEFGIKL |

TABLE 3-continued

List of materials with at least one MORV from 0.5 to less than 1

| Number | Material Name | CAS Number | Comment Code |
|---|---|---|---|
| 496 | 4-cyclohexyl-2-methylbutan-2-ol | 83926-73-2 | BDEFGIJK |
| 504 | 2-benzyl-2-methylbut-3-enenitrile | 97384-48-0 | BDHJK |
| 509 | Citronellyl nitrile | 51566-62-2 | BCEFGIKL |
| 510 | Citronellyl phenylacetate | 139-70-8 | DFHJ |
| 512 | Citronellyl formate | 105-85-1 | BCEFGJKL |
| 515 | Citronellyl benzoate | 10482-77-6 | DFHJ |
| 517 | Citronellol | 106-22-9 | BCHIJKL |
| 518 | Citronellal | 106-23-0 | ACHIJKL |
| 522 | Citral | 5392-40-5 | ACHIKL |
| 525 | cis-Pinane | 6876-13-7 | ADEFGIJKL |
| 526 | (Z)-3-methyl-2-(pent-2-en-1-yl)cyclopent-2-en-1-one | 488-10-8 | BCHIJKL |
| 528 | cis-iso-Eugenol | 5912-86-7 | CEFHIK |
| 535 | cis-3-Hexenyl valerate | 35852-46-1 | BDEFHJKL |
| 536 | cis-3-Hexenyl tiglate | 67883-79-8 | BDEFHJK |
| 538 | cis-3-Hexenyl propionate | 33467-74-2 | ACEFHIKL |
| 540 | cis-3-Hexenyl butyrate | 16491-36-4 | ADEFHJKL |
| 542 | cis-3-Hexen-1-ol | 928-96-1 | ACEFHIKL |
| 547 | cis-2-Hexenol | 928-94-9 | ACEFHIKL |
| 549 | Cinnamyl nitrile | 4360-47-8 | ACEFGIK |
| 554 | Cinnamic aldehyde | 104-55-2 | ACHIK |
| 556 | Cinnamyl nitrile | 1885-38-7 | ACEFGIK |
| 557 | Chloroxylenol | 88-04-0 | BCHIJK |
| 575 | Carvacrol | 499-75-2 | DHIJK |
| 576 | Carvone | 99-49-0 | ACGIJKL |
| 579 | Carbitol | 111-90-0 | BCEFGIK |
| 583 | Caproyl alcohol | 111-27-3 | ACEFGIKL |
| 585 | 2-(2,2,3-trimethylcyclopent-3-en-1-yl)acetonitrile | 15373-31-6 | ACGIJKL |
| 588 | Camphor | 76-22-2 | ACEFGIJKL |
| 602 | (E)-2-methyl-4-(2,6,6-trimethylcyclohex-1-en-1-yl)but-2-enal | 3155-71-3 | DHJK |
| 605 | Borneol | 507-70-0 | ACEFHIJKL |
| 617 | beta-Pinene epoxide | 6931-54-0 | ACEFGIJKL |
| 619 | beta-Phellandrene | 555-10-2 | ADEFGIJKL |
| 640 | Benzylacetone | 2550-26-7 | ACEFGIK |
| 641 | Benzyl salicylate | 118-58-1 | DFGJ |
| 645 | Benzyl isovalerate | 103-38-8 | BDEFHJK |
| 647 | Benzyl isobutyrate | 103-28-6 | BCHJK |
| 651 | Benzyl butyrate | 103-37-7 | BCEFHJK |
| 652 | Benzyl alcohol | 100-51-6 | ACEFGIKL |
| 662 | 1-(3,3-dimethylcyclohexyl)ethyl formate | 25225-08-5 | ADEFHIJKL |
| 664 | Anisyl acetate | 104-21-2 | BCEFGK |
| 665 | Anisyl formate | 122-91-8 | BCEFGK |
| 667 | Anethole | 104-46-1 | ACEFHK |
| 672 | Amyl benzoate | 2049-96-9 | DEFHJK |
| 687 | alpha-Terpinyl acetate | 80-26-2 | BDHJK |
| 699 | alpha-methyl-cyclohexanepropanol | 10528-67-3 | BDEFHIK |
| 701 | alpha-methyl cinnamaldehyde | 101-39-3 | ACHIK |
| 703 | alpha-Isomethylionone | 127-51-5 | BDHIJK |
| 740 | 2,5-Dimethyl-4-methoxy-3(2H)-furanone | 4077-47-8 | ACEFGIJKL |
| 743 | Allyl phenoxyacetate | 7493-74-5 | BCGK |
| 744 | Allyl Phenethyl ether | 14289-65-7 | ACEFHK |
| 745 | Allyl heptanoate | 142-19-8 | ADEFHJKL |
| 755 | N-ethyl-N-(m-tolyl)propionamide | 179911-08-1 | CEFHJK |
| 760 | 3-hydroxybutan-2-one | 513-86-0 | ACEFGIKL |
| 761 | Acetoanisole | 100-06-1 | BCEFHIK |
| 777 | 6-Methylquinoline | 91-62-3 | BCEFHIKL |
| 779 | 6,8-Diethyl-2-nonanol | 70214-77-6 | BDEFGIJKL |
| 784 | 5-Methyl-3-heptanone | 541-85-5 | ACFGIKL |
| 789 | 4-Vinylphenol | 2628-17-3 | BCHIK |
| 796 | 4-hydroxy-3-methoxy-cinnamaldehyde | 458-36-6 | CH |
| 797 | 4-Ethylguaiacol | 2785-89-9 | CEFHIK |
| 799 | 4-Damascol | 4927-36-0 | BDFHJK |
| 808 | 3-methyl-4-phenylpyrazole | 13788-84-6 | CEFHK |
| 810 | 3-Methyl-1,2-cyclopentanedione | 765-70-8 | ACEFGIKL |
| 811 | 3-Methoxy-5-methylphenol | 3209-13-0 | BCHIK |
| 812 | 3-Methoxy-3-Methyl Butanol | 56539-66-3 | ACGIKL |
| 817 | 3-Hexenol | 544-12-7 | ACEFHIKL |
| 819 | 3,7-dimethyl-2-methylene-6-octenal | 22418-66-2 | ADFHIJK |
| 820 | 3,7-dimethyl-1-octanol | 106-21-8 | BDEFGIJKL |
| 832 | 2-Phenylethyl acetate | 103-45-7 | BCEFHK |
| 835 | 2-Phenylethyl propionate | 122-70-3 | BCEFHJK |
| 836 | 2-Pentylcyclopentan-1-ol | 84560-00-9 | DEFHIKL |
| 838 | 2-nonanone propylene glycol acetal | 165191-91-3 | BDEFHJK |
| 845 | 2-Methoxy-3-(1-methylpropyl)pyrazine | 24168-70-5 | BCEFGIK |
| 846 | 2-isopropyl-N,2,3-trimethylbutyramide | 51115-67-4 | ACEFGIJK |
| 847 | 2-Isopropyl-5-methyl-2-hexenal | 35158-25-9 | ADFGIJKL |
| 848 | 2-Isopropyl-4-methylthiazole | 15679-13-7 | ACHIJKL |
| 851 | 2-Hexen-1-ol | 2305-21-7 | ACEFHIKL |
| 858 | 2-Butoxyethanol | 111-76-2 | ACEFGIKL |
| 875 | 1,4-Cineole | 470-67-7 | ADGIJKL |
| 880 | 1-(2,6,6-Trimethyl-2-cyclohexen-1-yl)-2-buten-1-one | 43052-87-5 | BDHIJK |
| 882 | (Z)-3-hepten-1-yl acetate | 1576-78-9 | ACEFHKL |
| 883 | (S)—(1R,5R)-4,6,6-trimethylbicyclo[3.1.1]hept-3-en-2-one | 1196-01-6 | ACEFGIJKL |
| 888 | (R)-(-)-Linalool | 126-91-0 | BCEFGIJK |
| 889 | (l)-Citronellal | 5949-05-3 | ACHIJKL |
| 891 | (d)-Citronellal | 2385-77-5 | ACHIJKL |
| 899 | (+)-Citronellol | 1117-61-9 | BCHIJKL |
| 900 | (-)-Citronellol | 7540-51-4 | BCHIJKL |
| 901 | (+)-alpha-Pinene | 7785-70-8 | ADEFGIJKL |
| 902 | (+)-Carvone | 2244-16-8 | ACGIJKL |
| 903 | (-)-alpha-Pinene | 7785-26-4 | ADEFGIJKL |
| 904 | Methyl 2-methylbutyrate | 868-57-5 | ACEFGIKL |
| 909 | Hexyl tiglate | 16930-96-4 | BDEFHJKL |
| 918 | Allyl 2-(cyclohexyloxy)acetate | 68901-15-5 | CHJK |
| 921 | 1,5-dimethylbicyclo[3.2.1]octan-8-one oxime | 75147-23-8 | CFHIJK |
| 931 | alpha-acetoxystyrene | 2206-94-2 | ACEFHIK |
| 940 | p-Cymene | 99-87-6 | ADGIJKL |
| 956 | Phenethyl formate | 104-62-1 | ACEFHK |
| 958 | Phenethyl isobutyrate | 103-48-0 | DHJK |
| 960 | Phenethyl tiglate | 55719-85-2 | DHJK |
| 971 | Phenylethyl methacrylate | 3683-12-3 | DHJK |
| 977 | p-Isopropylphenylacetaldehyde | 4395-92-0 | BDFHK |
| 981 | 1,2-dimethyl-3-(prop-1-en-2-yl)cyclopentan-1-ol | 72402-00-7 | BCEFGIJKL |
| 983 | p-Methoxyphenylacetone | 122-84-9 | BCEFHK |
| 986 | (2Z,5Z)-5,6,7-trimethylocta-2,5-dien-4-one | 358331-95-0 | ADHIJKL |
| 987 | p-Propyl anisole | 104-45-0 | ADEFHKL |
| 994 | p-t-butyl phenyl acetaldehyde | 109347-45-7 | BDHJK |
| 995 | p-tert-Amyl cyclohexanol | 5349-51-9 | BDEFHIJK |
| 1001 | Racemic alpha-Pinene | 80-56-8 | ADEFGIJKL |
| 1002 | 4-(4-hydroxyphenyl)butan-2-one | 5471-51-2 | CEFGIK |
| 1004 | Rhodinol | 141-25-3 | BCHIJKL |
| 1005 | Ethyl (2,3,6-trimethylcyclohexyl) carbonate | 93981-50-1 | BDEFHJKL |
| 1011 | 1-(3,3-dimethylcyclohexyl)ethyl acetate | 25225-10-9 | ADHIJKL |
| 1017 | S)-(+)-Linalool | 126-90-9 | BCEFGIJK |
| 1018 | Sabinene | 3387-41-5 | ADEFGIJKL |
| 1019 | Sabinene hydrate | 546-79-2 | ADEFGIJKL |
| 1030 | Propyl (S)-2-(tert-pentyloxy)propanoate | 319002-92-1 | BDEFHJK |

TABLE 3-continued

List of materials with at least one MORV from 0.5 to less than 1

| Number | Material Name | CAS Number | Comment Code |
|---|---|---|---|
| 1039 | Spirolide | 699-61-6 | BCGIKL |
| 1040 | (Z)-5-methylheptan-3-one oxime | 22457-23-4 | BCEFGIJKL |
| 1041 | 1-phenylethyl acetate | 93-92-5 | ACEFHIK |
| 1051 | Tetrahydrogeranial | 5988-91-0 | ADGIJKL |
| 1052 | Tetrahydroionol | 4361-23-3 | BDEFHIJK |
| 1054 | Tetrahydrolinalool | 78-69-3 | BDEFGIJKL |
| 1055 | Tetrahydrolinalyl acetate | 20780-48-7 | ADEFHJKL |
| 1058 | Ethyl (1R,6S)-2,2,6-trimethylcyclohexane-1-carboxylate | 22471-55-2 | ADEFHIJKL |
| 1061 | Thymol | 89-83-8 | BDHIJK |
| 1069 | trans-2-Hexenol | 928-95-0 | ACEFHIKL |
| 1071 | trans-2-tert-Butylcyclohexanol | 5448-22-6 | ACGIJKL |
| 1074 | trans-alpha-Damascone | 24720-09-0 | BDHIJK |
| 1076 | trans-Anethole | 4180-23-8 | ACEFHK |
| 1079 | trans-Cinnamic acid | 140-10-3 | CEFHK |
| 1081 | trans-Dihydrocarvone | 5948-04-9 | ACGIJKL |
| 1084 | trans-Isoeugenol | 5932-68-3 | CEFHIK |
| 1088 | Trichloromethyl phenyl carbinyl acetate | 90-17-5 | BDEFGJ |
| 1098 | 2-mercapto-2-methylpentan-1-ol | 258823-39-1 | ACEFHIJKL |
| 1110 | Vanillin acetate | 881-68-5 | CH |
| 1112 | Vanitrope | 94-86-0 | CEFHK |
| 1115 | 2,2,5-trimethyl-5-pentylcyclopentan-1-one | 65443-14-3 | BDFGIJKL |
| 1118 | Veratraldehyde | 120-14-9 | BCGIK |
| 1119 | (1R,5R)-4,6,6-trimethylbicyclo[3.1.1]hept-3-en-2-one | 18309-32-5 | ACEFGIJKL |
| 1122 | Verdol | 13491-79-7 | ACGIJKL |
| 1127 | 4-(tert-butyl)cyclohexyl acetate | 10411-92-4 | BDEFHJK |
| 1128 | 4-(tert-butyl)cyclohexyl acetate | 32210-23-4 | BDEFHJK |
| 1133 | Vethymine | 7193-87-5 | CEFGK |
| 1134 | 4-methyl-4-phenylpentan-2-yl acetate | 68083-58-9 | BDFHJK |
| 1141 | (Z)-1-((2-methylallyl)oxy)hex-3-ene | 292605-05-1 | ADEFHKL |

TABLE 4

List of materials with ALL MORVs from 1 to 5

| Number | Material Name | CAS Number | Comment Code |
|---|---|---|---|
| 7 | 3-methoxy-7,7-dimethyl-10-methylenebicyclo[4.3.1]decane | 216970-21-7 | BDEFHJK |
| 14 | Oxyoctaline formate | 65405-72-3 | DFHJK |
| 39 | 2,2,6,8-tetramethyl-1,2,3,4,4a,5,8,8a-octahydronaphthalen-1-ol | 103614-86-4 | DEFHIJK |
| 48 | Nootkatone | 4674-50-4 | DHJK |
| 183 | Khusimol | 16223-63-5 | CEFHJK |
| 199 | Isopimpinellin | 482-27-9 | CFGJ |
| 206 | Iso3-methylcyclopentadecan-1-one | 3100-36-5 | DEFGJK |
| 212 | Isoeugenyl benzyl ether | 120-11-6 | DFHJ |
| 215 | 1-((2S,3S)-2,3,8,8-tetramethyl-1,2,3,4,5,6,7,8-octahydronaphthalen-2-yl)ethan-1-one | 54464-57-2 | DHJK |
| 229 | Isobornyl isobutyrate | 85586-67-0 | BDEFHIJK |
| 260 | 2,3-dihydro-3,3-dimethyl-1H-indene-5-propanal | 173445-44-8 | DHJK |
| 261 | 3-(3,3-dimethyl-2,3-dihydro-1H-inden-5-yl)propanal | 173445-65-3 | DHJK |
| 281 | 3a,4,5,6,7,7a-hexahydro-1H-4,7-methanoinden-6-yl acetate | 5413-60-5 | CEFGJK |
| 329 | gamma-Eudesmol | 1209-71-8 | DFHJK |
| 335 | 4,6,6,7,8,8-hexamethyl-1,3,4,6,7,8-hexahydrocyclopenta[g]isochromene | 1222-05-5 | DEFHJK |
| 353 | (Z)-6-ethylideneoctahydro-2H-5,8-methanochromen-2-one | 69486-14-2 | CEFGJK |
| 360 | 8,8-dimethyl-3a,4,5,6,7,7a-hexahydro-1H-4,7-methanoinden-6-yl acetate | 171102-41-3 | DEFHJK |
| 441 | Octahydro-1H-4,7-methanoinden-5-yl acetate | 64001-15-6 | DEFHJKL |
| 484 | 3a,4,5,6,7,7a-hexahydro-1H-4,7-methanoinden-6-yl butyrate | 113889-23-9 | DEFHJK |
| 487 | 3a,4,5,6,7,7a-hexahydro-1H-4,7-methanoinden-5-yl isobutyrate | 67634-20-2 | DEFHJK |
| 488 | Curzerene | 17910-09-7 | DHJK |
| 501 | (E)-cycloheptadec-9-en-1-one | 542-46-1 | DEFGJ |
| 566 | Cedryl formate | 39900-38-4 | BDEFHJK |
| 567 | Cedryl acetate | 77-54-3 | DEFHJK |
| 569 | Cedrol | 77-53-2 | DEFHJK |
| 570 | 5-methyl-1-(2,2,3-trimethylcyclopent-3-en-1-yl)-6-oxabicyclo[3.2.1]octane | 139539-66-5 | DEFHJK |
| 573 | Caryophyllene alcohol acetate | 32214-91-8 | DEFHJK |
| 574 | Caryolan-1-ol | 472-97-9 | DEFHJK |
| 603 | Bornyl isobutyrate | 24717-86-0 | BDEFHIJK |

TABLE 4-continued

List of materials with ALL MORVs from 1 to 5

| Number | Material Name | CAS Number | Comment Code |
|---|---|---|---|
| 616 | beta-Santalol | 77-42-9 | DEFHJK |
| 621 | beta-Patchoulline | 514-51-2 | BDEFGJKL |
| 624 | beta-Himachalene Oxide | 57819-73-5 | BDFHJK |
| 627 | (2,2-dimethoxyethyl)benzene | 101-48-4 | DHJK |
| 632 | beta-Cedrene | 546-28-1 | BDEFGJKL |
| 663 | Anisyl phenylacetate | 102-17-0 | DFHJ |
| 680 | 2,2,6,6,7,8,8-heptamethyldecahydro-2H-indeno[4,5-b]furan | 647828-16-8 | ADEFHJK |
| 684 | alpha-Vetivone | 15764-04-2 | DHJK |
| 694 | alpha-Santalol | 115-71-9 | DEFHJK |
| 696 | alpha-Patchoulene | 560-32-7 | ADEFHJKL |
| 708 | alpha-Gurjunene | 489-40-7 | BDEFHJKL |
| 712 | alpha-Eudesmol | 473-16-5 | DEFHJK |
| 714 | alpha-Cubebene | 17699-14-8 | ADEFHJKL |
| 726 | alpha-Agarofuran | 5956-12-7 | BDEFHJK |
| 750 | Allo-aromadendrene | 25246-27-9 | BDEFHJKL |
| 764 | Acetarolle ™ | 744266-61-3 | DFHJK |
| 775 | 7-eip-alpha-Eudesmol | 123123-38-6 | DEFHJK |
| 776 | 7-Acetyl-1,1,3,4,4,6-hexamethyltetralin | 1506-02-1 | DEFHJ |
| 788 | 5-Cyclohexadecenone | 37609-25-9 | DEFGJK |
| 804 | 3-Thujopsanone | 25966-79-4 | BDEFHJK |
| 872 | 10-epi-gamma-Eudesmol | 15051-81-7 | DFHJK |
| 919 | 3a,4,5,6,7,7a-hexahydro-1H-4,7-methanoinden-6-yl propionate | 17511-60-3 | CEFHJK |
| 927 | 5-Acetyl-1,1,2,3,3,6-hexamethylindan | 15323-35-0 | DEFHJK |
| 933 | Patchouli alcohol | 5986-55-0 | DEFHIJK |
| 978 | 3a,4,5,6,7,7a-hexahydro-1H-4,7-methanoinden-6-yl pivalate | 68039-44-1 | DEFHJK |
| 1007 | (2R,4a'R,8a'R)-3,7'-dimethyl-3',4',4a',5',8',8a'-hexahydro-1'H-spiro[oxirane-2,2'-[1,4]methanonaphthalene] | 41816-03-9 | DEFHJK |
| 1022 | 2,2,7,9-tetramethylspiro(5.5)undec-8-en-1-one | 502847-01-0 | DHIJK |
| 1024 | (Z)-2-ethyl-4-(2,2,3-trimethylcyclopent-3-en-1-yl)but-2-en-1-ol | 28219-61-6 | DEFHJK |
| 1027 | 5-methoxyoctahydro-1H-4,7-methanoindene-2-carbaldehyde | 193425-86-4 | CHJK |
| 1029 | Sclareol oxide | 5153-92-4 | DEFHJK |
| 1035 | Spathulenol | 6750-60-3 | DEFHJK |
| 1038 | 1-(spiro[4.5]dec-7-en-7-yl)pent-4-en-1-one | 224031-70-3 | DGJK |
| 1060 | Thujopsene | 470-40-6 | BDEFGJKL |
| 1089 | Tricyclone | 68433-81-8 | DEFHJK |
| 1107 | Valerianol | 20489-45-6 | DEFHJK |
| 1129 | 1-((3R,3aR,7R,8aS)-3,6,8,8-tetramethyl-2,3,4,7,8,8a-hexahydro-1H-3a,7-methanoazulen-5-yl)ethan-1-one | 32388-55-9 | DHJK |
| 1131 | Methyl (Z)-2-(((2,4-dimethylcyclohex-3-en-1-yl)methylene)amino)benzoate | 68738-99-8 | DEFHJ |
| 1136 | Vetivert Acetate | 117-98-6 | DEFHJK |
| 1137 | Decahydro-3H-spiro[furan-2,5'-[4,7]methanoindene] | 68480-11-5 | DEFGJKL |
| 1140 | (1aR,4S,4aS,7R,7aS,7bS)-1,1,4,7-tetramethyldecahydro-1H-cyclopropa[e]azulen-4-ol | 552-02-3 | DEFHJK |
| 1142 | 3,5,5,6,7,8,8-heptamethyl-5,6,7,8-tetrahydronaphthalene-2-carbonitrile | 127459-79-4 | DHJ |
| 1143 | (1S,2S,3S,5R)-2,6,6-trimethylspiro[bicyclo[3.1.1]heptane-3,1'-cyclohexan]-2'-en-4'-one | 133636-82-5 | DEFHJK |
| 1144 | 1',1',5',5'-tetramethylhexahydro-2'H,5'H-spiro[[1,3]dioxolane-2,8'-[2,4a]methanonaphthalene] | 154171-76-3 | DEFHJK |
| 1145 | 1',1',5',5'-tetramethylhexahydro-2'H,5'H-spiro[[1,3]dioxolane-2,8'-[2,4a]methanonaphthalene] K | 154171-77-4 | DEFHJK |
| 1148 | 4,5-epoxy-4,11,11-trimethyl-8-methylenebicyclo(7.2.0)undecane | 1139-30-6 | DEFHJK |

TABLE 4-continued

List of materials with ALL MORVs from 1 to 5

| Number | Material Name | CAS Number | Comment Code |
|---|---|---|---|
| 1149 | 1,3,4,6,7,8alpha-hexahydro-1,1,5,5-tetramethyl-2H-2,4alpha-methanophtalen-8(5H)-one | 23787-90-8 | DEFHIJK |
| 1151 | 4,8-Dimethyl-1-(methylethyl)-7-oxabicyclo[4.3.0] nonane | TBD | BDEHJ |
| 1152 | 2,3-dihydro-1,1-dimethyl-1H-indene-ar-propanal | 300371-33-9 | DHIJK |

TABLE 5

List of materials with ALL MORVs greater than 5 to 10

| Number | Material Name | CAS Number | Comment Code |
|---|---|---|---|
| 248 | Hydroxymethyl isolongifolene | 59056-64-3 | BDEFHJK |

TABLE 6

List of materials with ALL MORVs from 0.5 to less than 1

| Number | Material Name | CAS Number | Comment Code |
|---|---|---|---|
| 472 | Decyl anthranilate | 18189-07-6 | DEFHJ |
| 526 | (Z)-3-methyl-2-(pent-2-en-1-yl)cyclopent-2-en-1-one | 488-10-8 | BCHIJKL |

The materials in Tables 1-6 can be supplied by one or more of the following:
Firmenich Inc. of Plainsboro N.J. USA; International Flavor and Fragrance Inc. New York, N.Y. USA; Takasago Corp. Teterboro, N.J. USA; Symrise Inc. Teterboro, N.J. USA; Sigma-Aldrich/SAFC Inc. Carlsbad, Calif. USA; and Bedoukian Research Inc. Danbury, Conn. USA.
Actual MORV values for each material listed in Tables 1-6 above are set forth below in Table 7 as follows:

TABLE 7

| Material No. | MORV value for Equation a.) | MORV Value for Equation b.) | MORV Value for Equation c.) | MORV value for Equation d.) |
|---|---|---|---|---|
| 1 | 0.548223914 | 0.876283261 | 1.22018588 | −0.41901144 |
| 2 | 1.520311929 | 3.493450446 | 2.70657265 | 5.11342862 |
| 3 | 2.267801995 | −0.81712657 | 0.43218875 | 1.595983683 |
| 4 | −0.591063369 | −0.48283571 | 0.16199804 | 1.210497701 |
| 7 | 1.437444636 | 2.131822996 | 3.81633465 | 1.318339345 |
| 9 | 2.151445882 | −0.46189495 | 0.56090469 | 1.206360803 |
| 10 | 2.5733592 | −0.58780849 | 1.39751471 | 1.258361951 |
| 11 | 3.052627325 | 1.008519135 | −0.30475953 | 0.076323462 |
| 12 | 0.683776599 | −0.01157903 | 0.82853231 | 0.326169402 |
| 13 | 1.549643217 | 1.809183231 | 0.70864531 | 2.22799611 |
| 14 | 2.82111224 | 2.339505033 | 1.240818 | 2.502429355 |
| 16 | −0.31551128 | −0.06816599 | −0.04371934 | 2.76742389 |
| 17 | −1.334904153 | −0.5773313 | 1.75644798 | 1.898455724 |
| 18 | −1.34154226 | −2.63596666 | 0.06885109 | 1.001431671 |
| 19 | 0.15532384 | 0.09866097 | 0.64214585 | −0.33330779 |
| 20 | 0.640261783 | 0.693213268 | 0.54637273 | −0.97556029 |
| 21 | 0.936895364 | −0.01521118 | 1.1697513 | −0.63510809 |
| 22 | 1.158981042 | 1.115900089 | −0.25859776 | 1.318200884 |
| 23 | 3.702361074 | 1.399942641 | 5.23954766 | 7.089933671 |
| 24 | 0.773874141 | 0.146848137 | −1.05705847 | −0.36193173 |
| 25 | −1.016103969 | −1.18967936 | 0.78064625 | 2.944710012 |
| 25 | −1.016103969 | −1.18967936 | 0.78064625 | 2.944710012 |
| 26 | 0.615085491 | −0.00096877 | −0.35697252 | −0.18121401 |
| 27 | 0.70261974 | −0.22197386 | 0.19710806 | −2.37196477 |
| 28 | 1.366472597 | −0.42546942 | −0.59394241 | −0.01417395 |
| 29 | 1.096043453 | −1.02972898 | −1.42167356 | −0.63817943 |

TABLE 7-continued

| Material No. | MORV value for Equation a.) | MORV Value for Equation b.) | MORV Value for Equation c.) | MORV value for Equation d.) |
|---|---|---|---|---|
| 30 | 1.143415203 | −0.85945441 | −0.41416913 | 2.499807942 |
| 31 | 1.138642907 | −0.19595476 | −0.54547769 | −0.98828898 |
| 32 | 1.914414495 | −0.64487788 | 0.63212987 | 1.166699371 |
| 33 | 0.314847366 | 1.848003955 | −1.3905032 | −0.62848261 |
| 34 | −0.113542761 | 0.981530917 | 0.32824239 | 1.126524277 |
| 35 | 0.472382903 | 1.494882467 | −0.07201236 | −0.64589543 |
| 36 | 3.158513795 | 1.084094934 | −0.00328981 | −0.17786385 |
| 37 | −1.055631982 | 2.240172964 | 0.92596118 | 2.105391988 |
| 38 | 3.158513795 | 0.592820874 | −0.49326241 | 0.212867212 |
| 39 | 1.083800659 | 2.069727985 | 2.48170879 | 3.205630609 |
| 42 | −0.103134861 | 0.267726008 | −0.65350189 | 1.125952363 |
| 43 | 0.323961628 | 1.469295081 | −0.52991193 | 0.797908251 |
| 47 | 1.703678841 | 1.348737095 | 2.00634162 | −0.16505407 |
| 48 | 2.370955056 | 2.783472865 | 2.68240273 | 1.221864405 |
| 49 | 1.670680003 | −0.41866107 | −0.9173849 | 1.181929544 |
| 50 | 1.670680003 | 0.076369374 | −0.49915943 | −0.85392575 |
| 52 | 0.464485039 | 0.057512869 | 1.31230219 | −0.11170276 |
| 53 | 0.626671823 | −0.46954947 | −0.33383736 | 0.277079201 |
| 54 | 0.666149043 | 0.009549925 | −0.36226343 | 0.197224432 |
| 55 | 0.723473579 | −1.50916383 | −0.3848989 | −0.71458778 |
| 57 | 0.381273227 | 1.192994109 | 1.65593321 | −1.65739236 |
| 59 | 0.561360663 | −0.17793966 | −1.63250554 | −0.7564969 |
| 61 | 0.146473611 | −0.01535544 | −0.16339658 | 1.738656146 |
| 62 | 1.20162032 | −0.3576095 | −0.10695443 | 1.322155191 |
| 63 | 1.084291915 | 2.258720158 | −1.01245416 | 1.688283974 |
| 64 | 0.744770665 | 0.155243763 | −1.8029919 | 1.023503542 |
| 65 | 0.972835178 | 2.797151284 | 1.53453579 | 0.857051645 |
| 67 | 2.069410561 | 0.021831924 | 0.37855159 | −0.67235457 |
| 68 | 0.527636614 | 0.590831983 | 1.02843762 | 2.208655795 |
| 69 | 2.133965691 | 2.088998449 | 2.05751412 | −0.9433713 |
| 70 | 0.327378959 | 0.996844599 | 1.23648533 | −1.25138371 |
| 71 | 1.40093669 | 0.778222691 | 0.70401172 | −0.24075444 |
| 72 | 0.617697349 | −0.29503359 | 0.52404847 | 0.816184656 |
| 73 | 0.617792473 | 0.888976061 | −0.45289639 | 0.615659244 |
| 74 | 1.437359024 | 1.548292147 | 0.10314807 | −0.48982286 |
| 75 | −1.970885622 | 3.398008325 | 4.08025266 | −0.89948156 |
| 76 | −1.32746934 | −2.65365233 | 0.10272816 | 1.001614125 |
| 77 | −2.541686116 | 3.295534192 | 3.75284227 | 0.404837808 |
| 78 | −2.110794 | 2.109874746 | 3.13350902 | −0.3880285 |
| 79 | 1.641162056 | −0.28533994 | 1.53676145 | 0.652696023 |
| 80 | 1.594400214 | 0.283682865 | 2.23140233 | 1.111682021 |
| 81 | 0.176566806 | −2.0786518 | −2.13986952 | 0.981126964 |
| 82 | 0.980373758 | −0.28813159 | 0.19404501 | 1.252564677 |
| 83 | 0.941833098 | 0.317310013 | 1.17606727 | 0.72992237 |
| 84 | 0.774237336 | −0.27140727 | 0.72461427 | −1.56415746 |
| 85 | 2.092976965 | 0.810644229 | 0.82999192 | −0.62861806 |
| 91 | 2.061595915 | −0.79930338 | −0.18285395 | −0.66898499 |
| 92 | 2.068748434 | −0.24299896 | 0.07214682 | −1.11758276 |
| 93 | −0.08984279 | −1.06025959 | −0.05068694 | 1.560050105 |
| 96 | 0.927758203 | −0.44129515 | 0.89190422 | 0.744284978 |
| 97 | 0.658667572 | −0.68771072 | 0.46051026 | −0.53120883 |
| 98 | 0.853222693 | −0.2037738 | −0.21414441 | 1.119784962 |
| 100 | 1.654535066 | 0.995056228 | 2.35139085 | 0.543654824 |
| 101 | 2.173663649 | −0.11491477 | 1.48285148 | 1.698527571 |
| 102 | 2.066679492 | −0.16785146 | −0.84780149 | 0.12159477 |
| 103 | 2.335152618 | −0.02866585 | 0.16993375 | −0.98254522 |
| 104 | 2.760588276 | 0.459513599 | 1.35310241 | 0.000336976 |
| 105 | 1.654535066 | 3.654489674 | 3.13033965 | 0.544225478 |
| 106 | 1.750588169 | −0.55853348 | 0.50257773 | 1.630011313 |
| 107 | 0.896789863 | 0.73615897 | 0.53011623 | −0.54697747 |
| 108 | 0.532375207 | 0.826537134 | 1.21040312 | 0.690230716 |
| 109 | 2.407655187 | 0.742651426 | 1.80322099 | 0.271832856 |
| 110 | 0.54830833 | 2.916795026 | 1.40126098 | 0.690230716 |
| 111 | 0.939597126 | −0.3750368 | −1.23479972 | −0.89366351 |
| 112 | 1.398518854 | 1.265740274 | 4.19618377 | −0.12762692 |
| 113 | 1.415726941 | 0.086297006 | 3.43559555 | −0.12964168 |
| 115 | −1.557729423 | −0.44113526 | 0.86330536 | 0.590708892 |
| 116 | 0.193562268 | −1.58091165 | 0.83247813 | −0.70978039 |
| 117 | 1.353510875 | −0.59062398 | −0.31776345 | −0.3050158 |
| 119 | 0.830052725 | 2.28725579 | 0.38409695 | 0.219336109 |
| 120 | 1.261997955 | −0.22622961 | −1.04772194 | 2.028504137 |
| 122 | 1.505653628 | −1.14748206 | −0.19760084 | −0.81373045 |
| 123 | −0.658721962 | −0.21299878 | 1.01439841 | −0.76731016 |
| 125 | 0.749676998 | −1.0761601 | 0.99563924 | −1.15409002 |
| 126 | 0.931054384 | −0.35067079 | 1.06050832 | −1.62171794 |
| 128 | −1.344832644 | −0.09451199 | 1.19145467 | 1.621274257 |
| 130 | 1.153249538 | 1.605070708 | 2.38047907 | −0.93842293 |

TABLE 7-continued

| Material No. | MORV value for Equation a.) | MORV Value for Equation b.) | MORV Value for Equation c.) | MORV value for Equation d.) |
|---|---|---|---|---|
| 133 | 0.840066046 | 0.2323025 | 0.19054023 | −0.26588341 |
| 134 | 0.522267541 | 0.824106618 | 1.83479545 | 0.364403434 |
| 135 | 2.142817887 | 2.142411243 | −0.93830995 | 0.696522652 |
| 137 | 3.052627325 | 3.606270166 | 0.50445208 | 0.076323462 |
| 140 | −0.153437637 | 0.246303216 | 0.76565758 | 1.800968868 |
| 141 | 2.067620311 | 1.424830396 | 2.33536931 | 7.644025075 |
| 142 | 0.98353103 | 1.950251373 | 2.50851828 | −0.24499521 |
| 143 | 1.736969725 | 0.991537809 | 2.5691601 | 1.227191656 |
| 145 | −0.211768579 | 1.46336231 | −0.93580247 | −1.48749449 |
| 146 | 1.912710035 | 0.926306508 | 1.81253333 | 0.494121361 |
| 147 | 0.675736703 | 0.99202385 | −0.66034472 | −0.66302669 |
| 148 | 0.757176542 | 1.83006252 | 0.16210659 | 0.243674851 |
| 149 | 0.438772371 | 1.091438092 | −0.1560319 | −0.61711642 |
| 150 | 0.84399938 | 0.675302022 | −1.69771411 | −0.73841711 |
| 151 | 0.633570539 | 0.988413715 | −0.54991825 | −0.43550324 |
| 152 | 0.911582356 | 1.974700218 | −0.92267786 | 0.628660087 |
| 153 | 0.319053885 | 2.531735341 | −0.39139184 | 0.734629224 |
| 154 | 0.714814512 | 0.690769753 | −2.06588692 | −0.73356628 |
| 155 | −0.161798388 | 0.032135767 | −0.13802086 | 1.734928461 |
| 156 | −0.571799976 | −1.32834264 | −1.65346017 | 1.856689553 |
| 157 | 0.131224024 | 0.21510779 | −1.70996346 | 0.964902175 |
| 158 | 1.201616145 | −0.21158932 | −0.8501176 | −0.33330779 |
| 159 | 0.811289908 | 1.606645397 | 0.25352447 | −1.83775117 |
| 159 | 0.811289908 | 1.606645397 | 0.25352447 | −1.83775117 |
| 161 | 0.475184006 | 1.99305646 | 1.90910177 | 3.288337059 |
| 162 | 0.833030517 | 0.487189028 | 1.76798642 | 0.104378164 |
| 163 | 0.58993703 | −0.46431772 | 0.74883588 | −0.81090824 |
| 166 | −0.121286831 | −0.84664528 | −0.32625341 | 0.778055656 |
| 167 | 0.846400186 | −0.25922232 | 0.69248774 | 1.183696217 |
| 168 | −0.310930833 | −0.81048493 | 0.08527131 | 1.61831109 |
| 169 | −0.2346025 | 0.890438419 | −0.13206526 | −0.83961838 |
| 170 | −0.169223695 | 1.172917966 | −0.11306441 | 0.099121666 |
| 174 | 2.863652137 | 0.236674094 | −0.69038707 | 1.610215283 |
| 175 | 1.789769228 | −0.31740428 | −0.89529921 | −0.09686469 |
| 176 | 2.625947334 | 0.083548191 | 0.30634559 | −0.35925728 |
| 177 | 1.674319352 | −0.22179044 | 0.42093738 | −0.23683577 |
| 178 | 2.863652137 | 0.727069168 | −0.26724686 | −0.44888613 |
| 179 | 0.070511885 | 0.365852864 | 1.35327505 | −0.03748038 |
| 181 | 0.976254543 | 0.691638796 | 0.51371978 | −0.02503945 |
| 182 | −1.842503751 | −0.12688474 | 2.56277877 | 0.111744488 |
| 183 | 3.195758563 | 3.886545621 | 4.29482769 | 3.829845293 |
| 184 | 0.333889534 | −0.67236766 | 2.21605977 | 4.254612125 |
| 185 | 5.61162203 | 1.40458529 | 2.86231343 | 1.035135749 |
| 186 | 1.068190511 | −0.65969343 | −0.63104765 | −1.36962992 |
| 187 | 1.396358739 | 0.249705611 | 0.81449499 | −0.15353102 |
| 189 | 1.544466636 | −0.33742685 | 0.8096674 | −0.44483677 |
| 190 | −0.210918777 | −1.04086063 | 0.02614862 | 3.362615492 |
| 191 | 0.715897301 | 0.666316436 | −0.41719538 | 0.400723176 |
| 192 | 0.65612864 | 1.231196814 | 0.75462061 | 1.514581532 |
| 193 | −0.394884432 | 1.129269425 | −0.3157071 | −0.61478944 |
| 194 | −2.111794245 | −0.71010521 | 0.53077207 | 0.59302222 |
| 195 | 1.18880856 | 0.704463775 | 1.99312777 | 1.419709023 |
| 196 | 1.885714606 | 0.436434665 | 1.44657532 | 1.145809063 |
| 197 | 2.174580668 | 0.133070149 | 0.99814905 | 0.871658496 |
| 198 | −0.533922573 | −2.16213117 | 0.5812107 | −0.92280453 |
| 199 | 1.493919434 | 1.45125612 | 1.95141371 | 4.403441058 |
| 201 | −0.005520296 | −0.83362523 | 0.65480762 | −0.38894276 |
| 204 | 0.732981164 | −0.97494758 | −0.91192246 | −1.00034323 |
| 205 | 0.991838899 | −0.60053505 | −0.49983634 | 0.674468753 |
| 206 | 2.147983695 | 1.291351958 | 1.64553247 | 1.626455601 |
| 208 | −0.386224123 | −0.24799559 | 1.19406353 | −1.61243489 |
| 209 | 1.447075297 | 0.122626462 | 1.08021156 | 0.473154634 |
| 210 | −0.386224123 | −0.24799559 | 1.19406353 | −1.61243489 |
| 211 | 2.186118467 | 1.873949371 | 0.64852028 | −0.59205851 |
| 212 | 1.367811201 | 1.689658923 | 1.8017376 | 2.525531645 |
| 213 | 0.925016223 | 0.875610609 | 0.31462609 | 0.847028648 |
| 214 | −0.239873321 | 1.808823425 | −0.36105512 | −0.07650286 |
| 215 | 2.264275088 | 1.360001278 | 3.25759951 | 2.147928282 |
| 218 | −0.509585598 | −0.93428643 | 1.63030386 | −0.79436377 |
| 221 | 1.876297063 | 0.026873469 | 0.45442758 | 1.538486988 |
| 227 | 5.317676982 | 2.824566654 | 1.73360625 | 3.103310061 |
| 228 | 3.323728685 | 1.554268023 | 1.8883835 | 0.957527434 |
| 229 | 3.218950175 | 1.464118271 | 2.47512497 | 1.214429025 |
| 230 | 5.242356467 | 3.482206715 | 3.50441556 | 1.614847073 |
| 230 | 5.242356467 | 3.482206715 | 3.50441556 | 1.614847073 |
| 231 | 2.710087358 | 1.517756148 | 0.35088855 | 0.603171932 |
| 231 | 2.710087358 | 1.517756148 | 0.35088855 | 0.603171932 |

TABLE 7-continued

| Material No. | MORV value for Equation a.) | MORV Value for Equation b.) | MORV Value for Equation c.) | MORV value for Equation d.) |
|---|---|---|---|---|
| 232 | 0.703604481 | 0.42129186 | 0.39567696 | 0.41729786 |
| 233 | 1.312921486 | 0.816597603 | 2.17066283 | 0.472801294 |
| 234 | 0.874145958 | 0.741410502 | 1.71105733 | −0.47289415 |
| 237 | 0.778921491 | −1.02119303 | 0.4612164 | −0.8881184 |
| 238 | 0.681403734 | −0.342052 | 1.27750286 | −0.3383341 |
| 239 | −0.870637933 | −2.58292907 | 0.79173772 | −1.27888846 |
| 242 | 0.910211214 | 0.374558101 | 1.01712685 | 1.001043471 |
| 243 | 1.670680003 | 0.104780951 | −0.6545574 | −0.46985154 |
| 244 | 1.140332181 | 0.116513028 | 1.61110902 | 3.713305291 |
| 246 | −0.634992987 | 0.548746912 | 4.62542427 | 7.660969857 |
| 247 | −1.739729444 | −0.91508372 | 1.18693162 | 3.108631198 |
| 248 | 5.81821686 | 6.320330665 | 6.14379552 | 5.214046447 |
| 249 | 0.348188924 | −0.95333461 | −0.08432225 | 1.866717393 |
| 252 | 2.456287983 | −0.02516176 | 0.76814124 | 1.756087132 |
| 253 | 1.76915226 | 0.226389981 | −0.18115009 | −0.62385199 |
| 254 | 0.658956861 | −0.39322197 | −0.67153044 | 1.416053304 |
| 255 | 0.892122738 | −0.46985097 | 0.42813903 | −0.46752753 |
| 256 | 0.625043963 | −0.65111806 | 1.4319541 | 2.110656697 |
| 258 | −0.187789327 | −0.85870492 | −0.21766971 | 0.931521178 |
| 259 | −1.261365139 | −2.33099427 | 1.33595129 | 0.43644676 |
| 260 | 2.4020693 | 2.669351733 | 2.36395771 | 1.910609499 |
| 261 | 1.978618006 | 2.732613301 | 2.19594212 | 1.683156477 |
| 263 | 1.350274014 | −0.59210334 | 0.14780643 | −0.13113746 |
| 264 | 0.526085484 | −1.54983116 | −0.17497208 | −0.8204696 |
| 267 | 1.175997006 | −1.03507906 | −0.11004734 | −0.50564806 |
| 269 | 2.367197222 | 0.457286256 | 0.02211231 | 0.497925297 |
| 270 | 0.711734628 | −1.45058685 | −0.17018094 | −0.71795736 |
| 271 | 1.073564668 | −0.47951936 | −0.80269361 | 0.136837431 |
| 273 | 0.663835001 | −1.5674675 | 0.28509522 | −1.12959038 |
| 274 | 1.628173498 | −0.58892922 | −0.3892777 | −0.66728139 |
| 275 | 0.935336765 | −0.9522644 | −0.87000279 | −0.29365972 |
| 276 | −5.989155804 | 1.722071272 | 3.31094703 | 1.273171428 |
| 277 | 0.904631703 | −1.02628534 | 0.49274649 | 1.000655271 |
| 278 | 0.293923493 | −0.82335619 | 0.13147975 | 2.730914048 |
| 280 | −0.284822555 | 0.322094188 | 3.2184015 | 0.383213731 |
| 281 | 2.201373139 | 2.228820089 | 2.03455575 | 1.720697243 |
| 282 | 0.505189899 | −1.01844885 | −0.98499144 | 0.912195522 |
| 283 | 0.775002479 | −1.29876341 | −1.52162214 | −0.77292581 |
| 284 | 0.505189899 | −0.57830662 | −0.55673047 | −1.09870665 |
| 285 | −0.987611415 | 0.908212704 | 2.59089199 | 1.311154128 |
| 286 | −2.635687733 | −1.53554173 | 0.68132558 | 4.350511118 |
| 287 | −1.890800496 | −0.9175912 | −0.84177071 | 0.615422874 |
| 288 | −0.417807714 | −0.27643667 | 1.06515025 | 0.958812195 |
| 289 | 1.078763544 | 0.263281029 | 1.00763749 | 0.866949263 |
| 290 | 0.733561298 | −0.47493387 | 0.17088582 | 1.536463653 |
| 292 | 1.2252731 | 0.720498276 | 4.33362953 | 2.202084022 |
| 293 | 0.947860369 | 0.93449449 | 1.85056304 | 0.355024738 |
| 294 | −1.051634009 | 0.136579632 | 2.17918871 | −0.01949057 |
| 295 | 1.039790111 | 0.81471915 | −0.94326824 | 0.887662055 |
| 296 | 1.009509413 | 1.364418947 | 1.42805339 | 0.429992055 |
| 300 | 0.246930208 | 1.113809101 | 0.25540773 | 0.528760053 |
| 301 | 0.246930208 | 1.113809101 | 0.25540773 | 0.528760053 |
| 302 | 0.697198045 | −0.41500676 | −2.35076003 | −0.60639529 |
| 303 | 0.10667178 | 3.580489288 | 0.25893587 | 2.329367856 |
| 306 | 0.561360663 | −0.17793966 | −1.63250554 | −0.7564969 |
| 307 | 1.583243229 | 1.398558046 | 0.152423 | −0.13988304 |
| 308 | −0.067380931 | 0.74278658 | 0.29217479 | 0.180866298 |
| 310 | 0.238202662 | 0.926241567 | −0.66649303 | 0.508184193 |
| 312 | 0.714965519 | −0.45511207 | −2.34849436 | −0.9953911 |
| 314 | 0.736369813 | −0.52068396 | 0.53882253 | −0.7059813 |
| 316 | 2.314558863 | −0.25458611 | 0.22080129 | −0.04142716 |
| 317 | 1.095005005 | 0.057439852 | −1.20728654 | 0.035895107 |
| 318 | −0.111714595 | −0.61079351 | −1.16010053 | 1.102488007 |
| 319 | −0.264829849 | 0.540388888 | 0.10729709 | −0.57215449 |
| 321 | 1.243861203 | −0.75229123 | 0.05515858 | −0.34659253 |
| 322 | 0.956379568 | 2.838565742 | 2.7997689 | 0.805938034 |
| 323 | 1.884902746 | 0.813499245 | 0.86344403 | −0.1241887 |
| 324 | 0.189037208 | 1.105600415 | 0.48460989 | 0.285938173 |
| 325 | 0.791400443 | 2.454239197 | 1.54315324 | 1.416449646 |
| 328 | 1.22836182 | 2.190068443 | 2.48751772 | 0.126982574 |
| 329 | 1.800767509 | 1.372656013 | 2.09551175 | 2.849728342 |
| 330 | 2.688999059 | 0.017422444 | 0.34929031 | 0.108155361 |
| 331 | −0.223648429 | 0.873635097 | 1.78683863 | 0.126324441 |
| 332 | 1.884902746 | −0.46695445 | 0.1761545 | −0.11026722 |
| 333 | 0.956379568 | 2.838565742 | 2.7997689 | 0.805938034 |
| 334 | 0.569368001 | 2.811464091 | 1.88866785 | −0.16122533 |
| 335 | 1.931053264 | 2.306571877 | 4.45651797 | 4.474221307 |

TABLE 7-continued

| Material No. | MORV value for Equation a.) | MORV Value for Equation b.) | MORV Value for Equation c.) | MORV value for Equation d.) |
|---|---|---|---|---|
| 336 | 1.355107839 | −0.49142588 | 0.83879083 | 0.18350392 |
| 338 | 1.025467157 | −0.99345477 | 0.57780149 | −0.19101275 |
| 339 | 1.216559787 | −0.68632827 | 0.71921804 | 0.140021721 |
| 342 | 2.073599715 | −0.19777074 | −0.44964804 | −0.71885866 |
| 343 | 3.375840967 | 3.294907583 | 5.0378352 | 4.14804591 |
| 344 | 0.926453735 | 1.336260845 | 2.20088072 | 0.226359561 |
| 346 | −0.133453942 | −0.27276578 | 0.95852923 | −0.88404805 |
| 347 | −0.414858428 | −0.94736055 | 1.9452074 | −1.32753709 |
| 349 | 0.011110326 | 0.415952358 | 1.08076289 | 2.638925816 |
| 350 | −1.366284701 | −1.3912958 | −0.0683659 | 1.205395618 |
| 352 | 2.592229701 | 2.014162407 | −0.56599991 | −0.19676404 |
| 353 | 2.347680291 | 1.432589328 | 3.81650185 | 2.28664738 |
| 354 | −0.094599823 | 0.704257624 | 0.8494127 | −0.05632553 |
| 355 | −0.534528735 | −0.26820008 | 0.69328667 | 0.63557685 |
| 356 | 0.71431796 | 0.568464069 | 1.14931631 | 0.32594963 |
| 358 | 1.637857828 | 1.932629993 | 0.68535871 | −1.06298922 |
| 359 | 3.169264285 | 2.326146291 | 5.44251947 | 3.621423972 |
| 360 | 2.824830639 | 3.29829616 | 3.43870859 | 3.771256974 |
| 361 | 0.772183137 | 0.62924397 | 1.14549597 | 0.743423792 |
| 362 | 2.158106604 | −0.08901432 | 0.85035629 | −0.37323677 |
| 363 | 1.485114303 | −0.85819594 | 0.70929196 | 4.132013298 |
| 364 | −0.661168364 | −0.30270875 | 2.49237859 | −0.7675819 |
| 365 | −0.518303431 | −2.08665423 | 0.5658944 | −1.10451499 |
| 366 | −0.501301831 | 0.561788544 | 0.14113617 | 0.610082057 |
| 368 | −0.106125097 | 1.092782715 | −0.89571841 | −0.08594454 |
| 369 | 1.43532227 | 1.656262941 | −1.09448841 | 1.674272267 |
| 370 | 1.064083705 | −1.08482967 | 0.35640283 | 0.866246621 |
| 371 | 1.933819902 | 0.975863726 | 1.62799441 | 1.492919426 |
| 372 | 1.933819902 | 0.975863726 | 1.62799441 | 1.492919426 |
| 373 | 0.274120553 | 2.246646022 | 2.93946992 | 2.617412085 |
| 374 | 0.940949346 | 2.935858163 | 0.52084392 | 0.847114052 |
| 375 | 0.177236108 | 2.745061961 | 0.76268843 | 0.373809692 |
| 376 | −0.999571921 | 0.579320229 | −0.06019938 | −0.94280945 |
| 377 | 0.521811983 | −0.8476641 | 0.7732327 | 1.729406547 |
| 378 | −0.532701772 | −2.17823188 | 1.26760147 | 0.815211357 |
| 379 | −0.684994963 | 0.018353057 | −0.8170018 | 0.582030709 |
| 381 | 1.592237677 | 1.373054134 | 0.60184939 | −0.30300485 |
| 385 | 0.967501839 | 0.136172137 | 1.3645564 | 0.374341215 |
| 385 | 0.967501839 | 0.136172137 | 1.3645564 | 0.374341215 |
| 386 | 1.247138794 | −0.97883463 | 0.03688288 | −0.57321578 |
| 387 | 0.785485559 | −1.23629818 | −0.07759084 | −0.71795736 |
| 388 | 1.503632155 | −0.13455265 | 0.86630165 | 0.102845335 |
| 388 | 1.503632155 | −0.13455265 | 0.86630165 | 0.102845335 |
| 390 | 0.811363694 | 0.872605919 | −0.17445198 | 1.358866557 |
| 391 | 1.653006495 | −0.44095837 | 0.46475017 | −0.16817306 |
| 394 | 1.043989895 | −0.82625074 | 0.40893134 | −0.10417542 |
| 397 | 1.430046723 | −0.79407262 | 0.15684862 | −0.4384694 |
| 398 | −1.401723491 | 0.271079592 | 1.35530191 | −0.63550333 |
| 400 | 0.762211626 | −1.06778628 | −0.93642574 | −0.13193338 |
| 407 | 0.591198428 | −0.8943503 | 1.41392426 | 2.694863328 |
| 412 | −0.067309295 | −0.21963004 | 0.57788677 | −1.22740398 |
| 413 | 0.630456164 | 1.538096427 | 2.10994563 | 2.45668637 |
| 414 | 0.460631327 | 3.678501689 | 1.18326431 | 1.28320952 |
| 415 | 0.060485009 | −1.37776759 | −0.22689728 | 2.328813337 |
| 416 | 1.864088631 | 0.2451067 | 1.63260125 | 1.855346924 |
| 417 | −0.747017264 | −2.60335412 | 0.85092701 | 3.525229717 |
| 418 | 3.678359573 | 3.437930194 | 4.42449746 | 0.716864637 |
| 419 | −0.131519393 | 0.731836014 | 0.81604919 | −1.29993979 |
| 420 | 0.11276779 | −0.13029453 | 0.19422843 | 0.853490939 |
| 421 | 2.819997124 | 0.193567405 | 1.15903162 | 1.748390255 |
| 424 | −0.211768579 | 1.46336231 | −0.93580247 | −1.48749449 |
| 425 | −1.467980751 | −2.41196874 | −0.34454968 | 2.161517022 |
| 426 | 2.176374648 | 2.131594325 | 1.99252316 | 0.002774099 |
| 428 | 2.10568799 | 0.336366154 | −1.41176883 | 0.827982605 |
| 429 | 2.179080731 | 0.811454228 | −0.58304782 | 0.827982605 |
| 432 | 0.814675557 | −0.13076033 | 1.07380397 | −0.01560954 |
| 436 | 0.003614069 | −0.4704298 | 1.6004974 | −1.27605297 |
| 437 | −0.070955783 | −0.17246926 | 0.32599434 | 0.682083059 |
| 438 | 0.71141055 | −0.62729405 | 0.6220964 | 0.498836975 |
| 439 | −2.152188932 | −1.81662702 | 0.66042162 | −1.57001886 |
| 440 | 0.194444196 | 0.880854446 | 0.80016905 | 0.373809692 |
| 441 | 2.349282571 | 1.734747324 | 1.71148239 | 1.274963632 |
| 442 | 0.243841724 | 0.036287037 | 0.51243015 | 0.361825534 |
| 443 | −0.131519393 | 0.731836014 | 0.81604919 | −1.29993979 |
| 444 | 0.607958335 | 1.910541857 | −0.42710132 | −0.46909656 |
| 445 | −0.047486491 | 1.045012945 | −0.25220201 | −0.31982826 |
| 447 | 0.611981677 | 0.559261438 | −0.31210071 | −2.20421695 |

TABLE 7-continued

| Material No. | MORV value for Equation a.) | MORV Value for Equation b.) | MORV Value for Equation c.) | MORV value for Equation d.) |
|---|---|---|---|---|
| 448 | 0.45491409 | 0.804084437 | 0.03088748 | −0.17549737 |
| 449 | 0.323968221 | −1.00428076 | −1.65151616 | 1.031096548 |
| 450 | 1.433196296 | −0.12277841 | 3.46809784 | −0.14760118 |
| 453 | 1.138642907 | 0.238344138 | −0.56453732 | −0.60639529 |
| 454 | 0.689556954 | −0.32116049 | 0.17614165 | 0.99165159 |
| 455 | −0.978653338 | −0.96381951 | 0.37950282 | 0.793341469 |
| 457 | 2.740852074 | 1.146976436 | 0.01429902 | 0.909817098 |
| 459 | 2.034203389 | −0.06483391 | 0.25864307 | 0.096715771 |
| 461 | 0.405441454 | 3.029508918 | 1.66201629 | 0.621375526 |
| 462 | 1.348588872 | 2.252065606 | 1.98535615 | 0.126982574 |
| 463 | 2.402548765 | 0.141297665 | 0.32401564 | 0.165555831 |
| 464 | 1.396358739 | −0.35292634 | 0.11760582 | −0.13960954 |
| 465 | 0.940569103 | 1.267891616 | 1.68420132 | 1.263608034 |
| 466 | −0.191220659 | 0.067062979 | 2.24237992 | 0.125280183 |
| 467 | 0.940569103 | 1.267891616 | 1.68420132 | 1.263608034 |
| 468 | 0.123370943 | 1.164309475 | 0.17099727 | −0.95446701 |
| 469 | 0.925252053 | −0.57178441 | 0.69807561 | −0.59133195 |
| 470 | 2.237616041 | 1.810156128 | −0.58140154 | 1.320304914 |
| 471 | 1.714516544 | −0.62135116 | 0.23636624 | −0.2706853 |
| 472 | 0.605628283 | 0.938001104 | 0.50028363 | 0.743911872 |
| 473 | 0.093847515 | −1.1973016 | −0.26960381 | 1.829684619 |
| 474 | 0.696773849 | 1.065592689 | 0.37607733 | −0.19214193 |
| 475 | 1.405352842 | 0.379589036 | 0.27781476 | 0.041425889 |
| 477 | 0.237582954 | 0.629327199 | 0.45159895 | −1.59912382 |
| 478 | 1.360648836 | 0.598053217 | 2.00883441 | −0.0827715 |
| 479 | 2.214928637 | −0.24358938 | −0.3486103 | 0.9190125 |
| 480 | 1.933819902 | −0.3826187 | 0.97439148 | 1.491603428 |
| 480 | 1.933819902 | −0.3826187 | 0.97439148 | 1.491603428 |
| 481 | 0.612364301 | −0.26364231 | −1.3201026 | −1.62884377 |
| 482 | 1.604448424 | 1.286308964 | −0.34289284 | 0.887781648 |
| 482 | 1.604448424 | 1.286308964 | −0.34289284 | 0.887781648 |
| 484 | 3.269313083 | 2.336715633 | 3.65534824 | 2.158890088 |
| 486 | 1.530484593 | 1.052491466 | 3.11297562 | 0.430146348 |
| 487 | 2.889323404 | 2.226094104 | 4.12877599 | 2.184426542 |
| 488 | 1.062548487 | 4.75312035 | 2.78435853 | 2.01925207 |
| 491 | 0.397432667 | −0.20071274 | 0.842202 | 1.944142408 |
| 493 | 0.270731661 | −0.7406408 | −1.17192239 | 1.401933582 |
| 495 | 0.298981649 | 0.854414067 | −2.2714622 | −0.62848261 |
| 496 | 0.565278409 | 0.659352661 | −0.00159534 | 0.384991859 |
| 497 | 2.972647554 | 1.210988046 | 0.08629653 | 0.991649406 |
| 498 | 2.863652137 | 0.229707592 | −0.75515466 | −0.06022029 |
| 502 | 0.478208715 | 1.827989577 | 0.67676345 | −0.88328385 |
| 503 | 0.845706083 | 1.117392544 | −0.21773539 | 0.272770415 |
| 504 | 0.837488879 | 0.874463134 | −0.08311625 | 0.149327397 |
| 505 | 1.749446006 | 0.076054765 | −0.59137073 | 0.291488011 |
| 509 | 0.716903285 | −0.22917288 | −1.93027881 | −1.52173529 |
| 510 | 0.241638743 | 0.769444787 | −0.07283731 | −0.38771737 |
| 512 | 0.556069536 | −0.47514685 | −1.88388474 | −1.67297277 |
| 515 | 0.23291131 | 0.598998195 | −0.99553291 | −0.40829542 |
| 517 | 0.784181146 | −0.20530019 | −1.89414748 | 0.152726109 |
| 518 | 0.742030255 | 0.281479436 | −1.4156326 | −1.91369695 |
| 519 | 0.367442761 | −0.50911405 | −0.77651804 | 3.081125259 |
| 520 | 1.28335174 | −0.16976166 | 0.19676128 | 1.493753388 |
| 521 | −1.105672292 | −1.29204085 | −0.95149628 | 1.817322011 |
| 522 | 0.714965519 | −0.45511207 | −2.34849436 | −0.9953911 |
| 524 | 0.325255266 | 1.131242708 | −2.79377204 | −0.62848261 |
| 525 | −0.210625832 | 0.979060885 | 0.37926876 | −2.08002977 |
| 526 | 0.698504484 | 0.548193178 | 0.92265651 | 0.500152973 |
| 527 | 0.420012766 | 1.731459464 | −0.23341719 | 0.139565409 |
| 528 | 0.161304111 | 0.66712144 | 0.58401752 | 0.373809692 |
| 529 | 0.911890585 | 0.353572744 | 1.04706167 | 1.001090055 |
| 530 | 1.670680003 | 0.86138741 | −0.27652639 | 1.174059185 |
| 531 | −0.169223695 | 1.172917966 | −0.11306441 | 0.099121666 |
| 532 | 2.237616041 | 1.438074134 | 0.31117554 | −0.71786492 |
| 534 | 1.205873658 | 1.32208026 | 1.21816392 | −0.5027271 |
| 535 | 0.999469738 | 0.056406435 | 0.72382479 | −0.61170287 |
| 536 | 0.63876931 | −0.39111525 | 0.08747854 | −0.66833729 |
| 537 | 0.689953348 | 1.206425159 | 0.58870271 | 0.198159994 |
| 538 | 0.54988634 | −0.32842011 | 0.69258273 | −0.81953404 |
| 540 | 0.735538933 | −0.20826876 | 0.6955468 | −0.7170218 |
| 541 | 1.097368973 | 0.740159871 | 0.12012053 | 0.137772993 |
| 542 | −0.24632881 | −0.09354384 | −0.13580399 | 0.599029186 |
| 544 | 0.687639306 | −0.30861817 | 1.14537443 | −1.12865481 |
| 546 | 1.670680003 | 1.94609957 | 0.19633838 | 1.14825764 |
| 547 | −0.24632881 | −0.23975349 | −0.01449288 | 0.574861147 |
| 548 | 1.349418105 | −0.29885837 | 0.42849141 | 0.008671721 |
| 549 | 0.623933699 | −0.62776258 | −1.2835205 | −0.23131507 |

TABLE 7-continued

| Material No. | MORV value for Equation a.) | MORV Value for Equation b.) | MORV Value for Equation c.) | MORV value for Equation d.) |
|---|---|---|---|---|
| 550 | 1.091300413 | −0.33969057 | 0.91994098 | 0.043900994 |
| 550 | 1.091300413 | −0.33969057 | 0.91994098 | 0.043900994 |
| 551 | 1.172668936 | −0.39476924 | −0.61394794 | −0.16425167 |
| 552 | 1.434150355 | 1.041294025 | 0.32000606 | 1.24279868 |
| 553 | 1.040907688 | −0.38050079 | −0.95306497 | −0.03036268 |
| 554 | 0.623933699 | −0.65991007 | −1.27562979 | −0.61529805 |
| 555 | 0.623933699 | −0.09654208 | −0.6432411 | 1.36608372 |
| 556 | 0.623933699 | −0.62776258 | −1.2835205 | −0.23131507 |
| 557 | −1.043779684 | 0.358151507 | 0.96578333 | −0.7498558 |
| 558 | 3.113548387 | 0.901949497 | −0.07402944 | 2.171129217 |
| 559 | 1.433732801 | 2.854621121 | 1.81079379 | 0.893806123 |
| 560 | 0.793851811 | 0.195900744 | 1.13222828 | −0.38432626 |
| 561 | 1.874725149 | 0.921395625 | 3.05642524 | 2.616508159 |
| 562 | −1.30410643 | −2.63450231 | 0.12574616 | 1.001870337 |
| 563 | −0.153585698 | 2.733591064 | 2.12854196 | 3.424603045 |
| 565 | 3.655479783 | 3.751479035 | 5.51820797 | 3.282822615 |
| 566 | 4.034374094 | 3.755759834 | 4.82506006 | 3.190861648 |
| 567 | 4.203811008 | 3.627632534 | 4.68751919 | 3.372829008 |
| 568 | 1.643514525 | 0.827299302 | 0.70706274 | 2.545428997 |
| 569 | 2.692371513 | 3.589810155 | 4.40390088 | 4.506937878 |
| 570 | 1.707556133 | 2.400065573 | 1.78745169 | 2.655458557 |
| 571 | 1.862893827 | 2.803280605 | 0.98209954 | 3.188564781 |
| 572 | 1.203581368 | 0.798608763 | 2.67898788 | 1.659633314 |
| 573 | 2.459623568 | 2.656773866 | 3.54771795 | 2.085649266 |
| 574 | 2.878405284 | 1.770500246 | 4.00464111 | 4.859737959 |
| 575 | −0.395731956 | 0.325594009 | 0.98982713 | −0.25791379 |
| 576 | −0.2346025 | 0.890438549 | −0.13206526 | −0.83961838 |
| 577 | 0.484934913 | 2.001798597 | −0.11430063 | −0.05230593 |
| 578 | 1.138642907 | −0.72228381 | −1.0321 | −0.60639529 |
| 579 | −2.722013313 | −3.79238321 | −1.13572295 | 0.953543134 |
| 580 | 1.138642907 | −0.66601616 | −0.95089973 | 1.036450105 |
| 581 | 1.105119249 | −0.82090309 | −0.06184517 | −0.90904158 |
| 582 | 2.092976965 | −0.31228784 | 0.08755137 | −0.62955362 |
| 583 | −0.24632881 | −1.33540368 | −0.96483147 | 0.624830731 |
| 584 | 2.237616041 | 0.30800753 | −0.44296441 | −0.71918014 |
| 585 | 0.634021669 | −0.28724544 | −0.74527157 | −1.361765 |
| 586 | 1.313957377 | 0.449601 | 1.50810166 | −0.30998322 |
| 587 | 0.304876136 | −0.43283205 | 1.23096012 | 0.398961811 |
| 588 | 0.449793066 | 0.007950225 | 0.8004147 | −0.63434071 |
| 589 | −0.681766404 | 1.08547116 | 0.54331319 | −2.16710754 |
| 591 | −0.34676031 | −0.77573166 | 1.85884084 | 0.312272735 |
| 592 | −1.573190219 | 2.29028194 | 1.86285367 | 0.687279186 |
| 594 | −1.45374647 | 0.452156392 | 2.48970747 | 0.858468114 |
| 595 | 0.058003677 | −1.91126878 | 1.52586392 | −0.07528071 |
| 599 | 1.485777974 | 1.54384772 | 0.79002365 | −0.09069773 |
| 600 | 1.914093549 | 0.841364523 | 0.15173954 | 0.255445859 |
| 601 | 1.203870517 | 1.17864533 | 1.22686262 | 0.453935114 |
| 602 | 0.771984982 | 0.66859171 | −0.37427136 | 0.07599515 |
| 603 | 3.218950175 | 1.464118271 | 2.47512497 | 1.214429025 |
| 604 | 2.710087358 | 1.517756148 | 0.35088855 | 0.603171932 |
| 605 | 0.703615734 | 0.42129186 | 0.39567696 | 0.41729786 |
| 606 | 0.055463315 | 1.972687323 | 3.42898264 | 1.395457482 |
| 607 | −0.146397553 | −2.05649732 | 0.17598641 | 1.900931587 |
| 608 | 1.473771668 | 2.08260463 | −1.09319437 | 0.44289209 |
| 609 | −0.466215117 | 0.845009196 | 1.89800228 | 0.840292062 |
| 610 | 2.14236439 | 1.079695535 | 0.29060257 | 1.329215628 |
| 611 | 1.078583502 | 1.707732184 | −0.73721672 | −0.87923138 |
| 612 | −0.128136098 | 1.038320983 | −0.63703066 | 0.184527669 |
| 613 | 1.599427115 | 3.615521066 | 0.43343413 | −0.1515479 |
| 614 | 1.489603514 | 2.706865637 | −0.06242639 | −0.47244791 |
| 615 | 1.960664614 | 4.490550162 | 2.26962278 | 0.346542121 |
| 616 | 2.689328335 | 3.692579375 | 2.01499213 | 1.348800283 |
| 617 | −0.845027889 | 0.504788036 | 0.4957383 | −0.65628324 |
| 618 | −0.461016335 | 1.612995126 | 1.09551709 | −1.62235977 |
| 619 | −0.222804396 | 0.361727974 | 0.62743416 | −1.02982449 |
| 620 | 0.745610019 | −0.76737462 | −0.67364137 | 1.696394301 |
| 621 | 3.671429366 | 1.708460032 | 4.57083156 | 1.955988764 |
| 624 | 2.139270802 | 2.093130621 | 2.5533383 | 3.30383102 |
| 625 | 0.665423108 | 1.356936283 | 1.5515704 | 1.874119646 |
| 626 | 1.292942787 | 0.621140137 | 2.28513785 | 1.042322574 |
| 627 | 1.14724223 | −0.51104438 | 1.01088446 | 1.51232276 |
| 628 | 1.44418619 | 3.825155203 | −0.84341678 | −0.02251455 |
| 631 | 2.622138509 | 5.106659136 | 4.48303003 | 2.115425367 |
| 632 | 2.450328692 | 4.670297017 | 4.54579766 | 2.15781135 |
| 633 | 1.560465308 | 2.636096631 | 2.45546606 | 0.920962489 |
| 635 | 1.510161132 | 2.388971583 | −0.63579931 | 1.939575919 |
| 636 | 1.433842763 | 0.529693203 | −0.23195491 | 1.22356734 |

TABLE 7-continued

| Material No. | MORV value for Equation a.) | MORV Value for Equation b.) | MORV Value for Equation c.) | MORV value for Equation d.) |
|---|---|---|---|---|
| 638 | 1.921725015 | 0.758255259 | 0.81570609 | 3.615611357 |
| 639 | 0.422001837 | −0.14885323 | −0.00660617 | 1.726576493 |
| 640 | 0.865825265 | −0.28827025 | −0.54129473 | 0.283616979 |
| 641 | 0.813978315 | 0.509726232 | 0.37457254 | 0.842075065 |
| 644 | 0.85173251 | 0.664325682 | 1.88299246 | 0.951603698 |
| 645 | 0.417907652 | −1.00347186 | 0.9667556 | −0.47157656 |
| 647 | 0.221569324 | −1.2239438 | 0.91464498 | −0.19166679 |
| 649 | −0.560315649 | −0.67419393 | −0.02482011 | 1.492767049 |
| 650 | 1.640396187 | 0.328871961 | 0.04729888 | 0.912259803 |
| 651 | 0.672555558 | −0.9987845 | 0.48545476 | −0.13530683 |
| 652 | −0.995969271 | −1.38653208 | −0.49268035 | 0.944524468 |
| 653 | 1.203949791 | 0.0153333 | −0.10401424 | 0.73323846 |
| 655 | 1.334772083 | 0.418728831 | −0.92221842 | 1.317365259 |
| 658 | 0.414934548 | 0.314990682 | 2.78051829 | 2.656854539 |
| 659 | 3.996948911 | 1.915319951 | 3.03990612 | 5.764113617 |
| 660 | 2.175041013 | 1.882945358 | 0.07779745 | −0.18323732 |
| 661 | −0.316755016 | 1.64607349 | 2.76327471 | 2.024910676 |
| 662 | 0.258228842 | 0.844792644 | 0.1924797 | 0.098776211 |
| 663 | 1.521826905 | 1.097809988 | 2.13583044 | 1.30609234 |
| 664 | 0.708920214 | −0.27795513 | 0.15395433 | 0.014791904 |
| 665 | 0.630772742 | −0.34278374 | 0.49097281 | −0.0565644 |
| 667 | 0.812238101 | 0.195908668 | 0.21564664 | 0.219336109 |
| 668 | 1.529097453 | 2.246515706 | 1.4678099 | −0.81836944 |
| 671 | 1.453855457 | −0.51177209 | −0.78608937 | 0.361715513 |
| 672 | 0.771613806 | −0.81209599 | −0.85297613 | 0.084880782 |
| 673 | 1.874725149 | 0.921395625 | 3.05642524 | 2.616508159 |
| 674 | 5.912391366 | 3.468705262 | 6.81994671 | 7.217631788 |
| 675 | 0.525794155 | 0.473286101 | 2.51749677 | 2.935001452 |
| 676 | 0.623704257 | 1.523736626 | 2.50208859 | 2.474137331 |
| 677 | −0.548848405 | 0.058004962 | 1.07849806 | 2.361730638 |
| 678 | 4.818555677 | 1.506257638 | 4.96635528 | 5.508133385 |
| 679 | 4.332202737 | 2.699343437 | 5.65576391 | 5.021298111 |
| 680 | 4.042984412 | 4.75506829 | 4.65903898 | 4.913020939 |
| 681 | 0.5959536 | 2.091803965 | −0.14697928 | −0.71889234 |
| 683 | 0.87899671 | 0.043210589 | 1.37554648 | −0.60198897 |
| 684 | 2.349844428 | 1.181400632 | 2.15359469 | 2.136987013 |
| 686 | 1.024635336 | 1.040500794 | 0.9820242 | −1.16405004 |
| 687 | 0.551495677 | 0.66297128 | −0.45433071 | −1.28827912 |
| 691 | 1.609835015 | 2.898881191 | −0.99203246 | −0.15162554 |
| 692 | 2.002379485 | 3.95875961 | 1.1705779 | 0.346542121 |
| 693 | 4.264631423 | 4.375626605 | 0.93418004 | 0.114988571 |
| 693 | 4.264631423 | 4.375626605 | 0.93418004 | 0.114988571 |
| 694 | 4.858313721 | 4.772826468 | 3.58732214 | 2.558402204 |
| 696 | 2.99409154 | 3.843066736 | 2.50597637 | 1.205022789 |
| 697 | 0.407534444 | 2.829113684 | 2.16548165 | 0.756766079 |
| 698 | 0.983060431 | 2.328872529 | 1.67788951 | 0.805938034 |
| 699 | 0.996500165 | 0.60129571 | −0.27496491 | −0.22179967 |
| 700 | 0.698400489 | 0.514637899 | 1.14265307 | 0.816064314 |
| 701 | 0.592372435 | −0.67812322 | −1.75051912 | −0.51109618 |
| 702 | −0.211768579 | 1.46336231 | −0.93580247 | −1.48749449 |
| 703 | 0.372029303 | 0.866016277 | −0.91679974 | 0.347054507 |
| 704 | 1.187861135 | 0.858978871 | 0.1265005 | 0.217668671 |
| 706 | 0.193569186 | 1.623921627 | 0.08867618 | 0.808617424 |
| 707 | 0.819562098 | 3.57840156 | 3.38080377 | 1.26599216 |
| 708 | 2.391828225 | 1.877690145 | 3.85935427 | 1.647356195 |
| 709 | 1.280902077 | 2.17019575 | 3.40315777 | 0.126982574 |
| 710 | 1.454593977 | 3.128186882 | −2.26368122 | −0.02251455 |
| 711 | −0.783387499 | 1.465620573 | 1.22912535 | −1.41213701 |
| 712 | 1.936489942 | 2.528373237 | 2.13424487 | 2.393940425 |
| 713 | 1.303999908 | 2.146563611 | −0.26420591 | −0.01477791 |
| 714 | 2.3584433 | 3.778880151 | 3.4396901 | 1.593719007 |
| 715 | 4.023918591 | 3.403899942 | 5.07447567 | 4.880181625 |
| 716 | 0.981194248 | 1.73892162 | 2.21166953 | 2.738129365 |
| 717 | 0.983060431 | 2.328872529 | 1.67788951 | 0.805938034 |
| 718 | 1.241840746 | 3.430871861 | 0.55000978 | 1.073616332 |
| 719 | 1.483275952 | 3.037398628 | −1.55547275 | −0.47244791 |
| 720 | 2.372311412 | 3.403234423 | −0.21191089 | −0.08519829 |
| 721 | 2.128185431 | 0.274654772 | 0.47626043 | 2.465333527 |
| 722 | 0.616377169 | −0.58753328 | 0.48821573 | 1.063402884 |
| 723 | −1.273274319 | −1.12897478 | 1.71118519 | 4.067480158 |
| 724 | 2.103515193 | 0.165377929 | −0.18223896 | 0.288303217 |
| 725 | 0.983060431 | 2.328872529 | 1.67788951 | 0.805938034 |
| 726 | 2.887615733 | 3.282342953 | 1.95034945 | 2.462290186 |
| 727 | 2.241052707 | 2.13951389 | 0.36814978 | 0.371689426 |
| 730 | 1.121105724 | −0.20397307 | −0.15741334 | 0.897609916 |
| 731 | 1.437838545 | −0.09620743 | 0.02756967 | 1.949139525 |
| 733 | −0.46922259 | 1.067777032 | 1.61226345 | 0.185415155 |

TABLE 7-continued

| Material No. | MORV value for Equation a.) | MORV Value for Equation b.) | MORV Value for Equation c.) | MORV value for Equation d.) |
|---|---|---|---|---|
| 735 | −0.081273581 | 1.192925027 | 1.67970188 | 0.33874614 |
| 736 | −0.13000788 | 1.099012031 | 1.64139691 | 0.248287146 |
| 738 | 1.670680003 | −0.20756775 | −0.73755051 | −0.84924056 |
| 740 | −1.532691904 | −2.55214711 | 0.57438104 | 0.555698696 |
| 741 | 1.407504561 | 0.048284736 | 1.01405149 | −2.2579901 |
| 742 | 0.644803847 | 0.644647752 | 1.35192052 | −0.62780087 |
| 743 | 0.174679072 | 0.169515693 | 0.62350977 | −0.08144308 |
| 744 | 0.02068385 | 0.648730454 | −0.04946215 | 0.214634634 |
| 745 | 0.741424752 | 0.523647641 | 0.52863925 | −0.65426285 |
| 746 | 1.285306965 | 1.929408375 | 0.85560877 | −1.4619958 |
| 748 | −1.513804897 | −1.10823383 | 1.09397284 | −0.88975989 |
| 750 | 2.554017714 | 3.544542579 | 4.42317523 | 1.647356195 |
| 752 | 2.592229701 | 1.158945916 | 0.24149847 | −0.58379051 |
| 754 | 1.649506181 | 1.31981993 | 2.36997533 | 0.406081966 |
| 755 | −0.028552173 | 0.253838465 | 0.95694896 | −0.16565786 |
| 757 | 1.446915042 | 0.673406021 | −0.6641103 | −1.80002119 |
| 758 | 5.933043009 | 5.716461604 | 6.67410554 | 4.433272782 |
| 760 | −3.195604514 | −2.60998376 | −0.11222221 | 0.792186468 |
| 761 | 0.286783044 | −0.52414055 | −0.57593161 | 0.628896611 |
| 763 | 1.405567948 | −0.84372738 | −1.32379279 | −0.50314577 |
| 766 | 0.279442569 | −1.00722191 | −0.18524031 | 2.487147765 |
| 767 | −1.32777782 | −2.36136561 | −0.79602501 | 1.247063893 |
| 768 | −0.692560954 | −1.92177717 | 0.46687554 | 2.400762497 |
| 769 | 1.889999468 | 1.112266205 | 0.82815523 | 0.525271623 |
| 770 | 2.237616041 | 2.282141767 | −0.149966 | −0.71866539 |
| 771 | 0.909356011 | 0.368597887 | 1.03689838 | 1.001198751 |
| 772 | 1.328601831 | 0.715296776 | 0.20358825 | 1.147403521 |
| 774 | 2.002379485 | 3.95875961 | 1.1705779 | 0.346542121 |
| 775 | 1.936489942 | 2.528373237 | 2.13424487 | 2.393940425 |
| 776 | 1.495019673 | 4.35984375 | 2.59969954 | 2.95313487 |
| 777 | 0.206892499 | −0.57813502 | −0.32983 | 0.781221286 |
| 778 | 1.340232187 | −0.11034804 | 0.35759778 | 1.690582999 |
| 779 | 0.595257521 | −0.85639987 | 0.19436224 | −0.73333902 |
| 781 | 2.187955186 | 2.571774369 | 2.74817529 | −0.52827851 |
| 782 | 0.893855657 | 0.63313304 | 1.19104388 | −1.61620514 |
| 784 | −0.275919571 | −1.64491584 | 0.60429762 | −1.5580623 |
| 786 | −0.043537347 | 1.337721065 | −0.56551398 | −0.02167052 |
| 788 | 2.147983695 | 1.250042565 | 1.72576392 | 1.626956379 |
| 789 | −0.624451013 | 0.76248127 | −0.79219481 | −0.73513092 |
| 791 | 0.227060873 | −0.04783658 | −0.16862915 | 1.166609659 |
| 792 | 0.90746622 | 1.643598677 | 0.26467094 | 0.396081003 |
| 796 | 0.811374104 | 0.766579899 | 0.10161642 | 0.135186519 |
| 797 | −0.185638022 | 0.53853264 | 0.65441562 | −0.25681926 |
| 799 | 0.657769581 | 0.095543194 | 0.89522656 | 0.558428618 |
| 800 | 0.227060873 | −0.04783658 | −0.16862915 | 1.166609659 |
| 802 | −0.660595577 | 1.597474466 | 1.49106895 | −0.20429128 |
| 803 | 1.706162052 | 0.623892414 | 0.59662073 | 0.7745661 |
| 804 | 3.478490379 | 2.348697011 | 3.96279011 | 2.456963386 |
| 805 | 0.377241729 | 0.83329773 | 0.1712741 | 1.057125999 |
| 806 | 2.863652137 | 0.771287371 | −0.4183972 | −0.44551461 |
| 807 | 1.794279084 | 0.711717977 | 0.35187068 | −1.0208486 |
| 808 | 0.408210632 | 0.633556897 | −0.37022584 | 0.717270748 |
| 810 | −2.506277966 | −2.61703099 | 0.87880054 | −0.72832121 |
| 811 | −0.789075789 | −0.15346024 | 0.64720487 | −0.48507671 |
| 812 | −1.395132583 | −2.59063834 | 0.14973761 | 0.623759794 |
| 814 | 0.414608216 | −0.23108581 | 1.15081653 | −1.10351559 |
| 817 | −0.24632881 | −0.09354384 | −0.13580399 | 0.599029186 |
| 819 | 0.805916178 | 0.96701754 | −0.8811308 | −1.23858491 |
| 820 | 0.744770665 | −0.73855596 | −0.2249849 | −0.2981968 |
| 821 | 1.099377934 | −0.55297074 | −0.58846144 | −1.64325365 |
| 824 | −0.183625049 | 1.183962609 | 1.63494269 | 0.25504959 |
| 826 | 1.678825829 | 1.234136613 | 1.45948258 | 0.224375571 |
| 827 | 2.592229701 | 0.621958527 | −0.52522117 | −0.19676404 |
| 828 | 2.592229701 | 0.57915141 | −0.51767373 | −0.58077497 |
| 829 | 1.670680003 | 1.284791367 | 0.14864516 | −0.84985664 |
| 831 | 1.116827432 | −0.75462162 | 0.39137278 | −0.04171761 |
| 832 | 0.516805788 | −0.98195801 | −1.03806082 | −0.25383454 |
| 833 | 1.490368312 | 0.080687244 | −0.97130296 | 0.833722265 |
| 834 | −0.369014518 | −1.35841128 | −1.27372214 | 1.351157886 |
| 835 | 0.914072736 | −0.8695664 | 0.36889122 | −0.08606658 |
| 836 | 0.998848923 | −0.42464651 | −0.23731009 | 0.395895785 |
| 837 | 1.670680003 | 0.070165381 | −0.64700996 | −0.85055617 |
| 838 | 0.810918992 | −0.75696962 | −0.21854084 | 0.836677293 |
| 839 | 1.066219316 | −0.66764691 | −0.49983634 | 0.669914 |
| 840 | 1.078821776 | −0.72511699 | −1.00012288 | −0.15789319 |
| 845 | −0.163950017 | −0.21616766 | 0.65276069 | −0.52575739 |
| 846 | 0.665621985 | −3.16625248 | 0.34329102 | −1.44312939 |

TABLE 7-continued

| Material No. | MORV value for Equation a.) | MORV Value for Equation b.) | MORV Value for Equation c.) | MORV value for Equation d.) |
|---|---|---|---|---|
| 847 | −0.233400992 | −1.15488444 | 0.83051343 | −1.85751897 |
| 848 | −0.631135606 | 0.037691556 | 0.57903451 | −0.9926 |
| 849 | 1.707541313 | 0.010345383 | 0.48581606 | 1.513341091 |
| 850 | 1.447075297 | 0.022864201 | 0.99130501 | 0.473154634 |
| 851 | −0.24632881 | −0.23975349 | −0.01449288 | 0.574861147 |
| 852 | 1.176028423 | −0.85747031 | −0.72464089 | 0.30542841 |
| 856 | 2.237616041 | 0.345329597 | −0.60597063 | −0.71581056 |
| 858 | −1.47960224 | −2.5770536 | −1.03619781 | 0.847300104 |
| 864 | 1.670680003 | 1.284791101 | 0.14864516 | −0.84985664 |
| 865 | 1.670680003 | 1.916382859 | 0.6998144 | 1.124089601 |
| 866 | 1.024819853 | −0.7521596 | 0.35073152 | −2.14193241 |
| 868 | 2.237616041 | −0.17986241 | −0.86317199 | 1.325805381 |
| 869 | 1.747776963 | −0.25802105 | −1.11614995 | −0.77093434 |
| 870 | 2.592229701 | 2.030913569 | −0.50618719 | 1.463926567 |
| 871 | 2.592229701 | 2.510587108 | −0.07540594 | −0.58371481 |
| 872 | 1.800767509 | 1.372656013 | 2.09551175 | 2.849728342 |
| 873 | 1.849432484 | 4.556065495 | −0.39732139 | −0.67726477 |
| 875 | 0.201768224 | 0.618509503 | −0.39732139 | −0.67726477 |
| 876 | 2.237616041 | 1.553468488 | −0.72864242 | −0.33330779 |
| 877 | 0.323968221 | −1.00428076 | −1.65151616 | 1.031096548 |
| 878 | 0.783570663 | 2.023288951 | −0.03975252 | 0.474038265 |
| 879 | 1.187592149 | 1.464239711 | 0.67009263 | 1.103774764 |
| 880 | −0.192632911 | 0.142411101 | 0.79310676 | 0.125548041 |
| 881 | 1.071875228 | 0.911734331 | −1.50008456 | 0.185176261 |
| 882 | 0.798806784 | −0.1516478 | −0.64900063 | −0.77199025 |
| 883 | −0.671908804 | −0.65984824 | 0.5238174 | −0.85314111 |
| 884 | 2.863652137 | 1.896850773 | 0.06443558 | −0.44689505 |
| 885 | 2.314558863 | −0.25458637 | 0.22080129 | −0.04142716 |
| 886 | 2.314558863 | −0.25458637 | 0.22080129 | −0.04142716 |
| 888 | 0.131224024 | 0.21510779 | −1.70996346 | 0.964902175 |
| 889 | 0.742030255 | 0.281479436 | −1.4156326 | −1.91369695 |
| 890 | 1.071875228 | 0.911734331 | −1.50008456 | 0.185176261 |
| 891 | 0.742030255 | 0.281479436 | −1.4156326 | −1.91369695 |
| 892 | 1.749446006 | 0.076054765 | −0.59137073 | 0.291488011 |
| 893 | 0.869958847 | 0.843158237 | 0.61532515 | 3.158279932 |
| 894 | 1.749446006 | 0.076054765 | −0.59137073 | 0.291488011 |
| 897 | −0.047486491 | 1.045012945 | −0.25220201 | −0.31982826 |
| 899 | 0.784181146 | −0.20530019 | −1.89414748 | 0.152726109 |
| 900 | 0.784181146 | −0.20530019 | −1.89414748 | 0.152726109 |
| 901 | −0.440378333 | 0.918089245 | 0.03050609 | −1.62235977 |
| 902 | −0.2346025 | 0.890438419 | −0.13206526 | −0.83961838 |
| 903 | −0.440378333 | 0.918089245 | 0.03050609 | −1.62235977 |
| 904 | −1.320466583 | −2.49763118 | 0.9787365 | −1.85867969 |
| 905 | −0.386224123 | −0.24799559 | 1.19406353 | −1.61243489 |
| 908 | 1.878331515 | 1.287303121 | 0.11530502 | 1.132065786 |
| 909 | 0.614968453 | −1.61827184 | −0.80789799 | −0.66927285 |
| 912 | 0.530707518 | 0.774109528 | 3.0396125 | 4.394775258 |
| 913 | 0.337020095 | 1.531840025 | 0.10544973 | 0.347450471 |
| 914 | 0.774589061 | 1.224705331 | 1.87994281 | −0.11684579 |
| 916 | −0.363201351 | 0.35600238 | −1.20673542 | 2.056973054 |
| 918 | 0.153047955 | 0.702054562 | 0.76757802 | 0.096096862 |
| 919 | 2.891894151 | 2.295157633 | 3.54101626 | 1.984030826 |
| 920 | 1.292959895 | 0.808281618 | 2.92956952 | 2.204248324 |
| 921 | −0.465333775 | 0.862817284 | 0.1439546 | 0.64701735 |
| 922 | 1.54265003 | 0.291977233 | 0.79089158 | 0.801314068 |
| 923 | 1.340862559 | 0.503169303 | 0.53213093 | 3.164832031 |
| 924 | 0.158497146 | 1.507280765 | 2.25315926 | 1.173977914 |
| 925 | 1.23162703 | 1.671882685 | 3.1838372 | −0.22917041 |
| 926 | 2.608734063 | 3.080604939 | −0.69726361 | −0.36219702 |
| 927 | 1.879182741 | 3.409153142 | 2.48473663 | 3.409954437 |
| 928 | −0.093106169 | 0.019939108 | 0.15932154 | 1.229749745 |
| 929 | 1.670680003 | 1.94609957 | 0.19633838 | 1.14825764 |
| 930 | 3.052627325 | 0.956834107 | −0.29721209 | −0.31007607 |
| 931 | 0.367631287 | 0.501274945 | −1.31074554 | −0.39331005 |
| 933 | 3.702965303 | 3.03402795 | 4.33630831 | 4.238503729 |
| 937 | 0.570011387 | 0.097928934 | 1.03350455 | −0.13392581 |
| 939 | 1.801474588 | 0.770314085 | 0.70188154 | 0.22333959 |
| 940 | −0.412950838 | −0.1781887 | 0.50649275 | −0.57215449 |
| 941 | 1.691004766 | −0.42331992 | 0.66279648 | 0.0318465 |
| 942 | 1.451782586 | −0.565439 | −0.32447381 | −0.43378383 |
| 943 | 1.188491672 | 0.120632811 | 0.20106994 | 3.078484746 |
| 945 | 1.214814941 | 0.806987609 | 0.47605587 | 1.372949466 |
| 946 | 0.561732094 | 1.21448402 | 0.35542793 | −1.03704442 |
| 947 | 0.956565856 | 1.505997176 | 0.88115653 | −0.60583691 |
| 948 | 0.592575441 | 1.383482681 | 0.93567635 | 1.058669028 |
| 950 | 0.343657562 | −0.85471906 | −0.21125904 | 1.184648122 |
| 951 | 1.236659334 | 3.828926809 | 1.57729777 | −0.31942874 |

TABLE 7-continued

| Material No. | MORV value for Equation a.) | MORV Value for Equation b.) | MORV Value for Equation c.) | MORV value for Equation d.) |
|---|---|---|---|---|
| 953 | 1.836389049 | 0.755753735 | −0.36014522 | 1.262853393 |
| 953 | 1.836389049 | 0.755753735 | −0.36014522 | 1.262853393 |
| 954 | 1.001653875 | −0.85635082 | 0.89224781 | −0.39245818 |
| 955 | −0.122918652 | −0.846489 | −0.63367729 | 1.182912962 |
| 956 | 0.589766639 | −0.9783487 | −0.67638264 | −0.38772225 |
| 958 | 0.715082397 | −0.90020686 | 0.86817768 | 0.030652004 |
| 959 | 1.609198886 | 0.500797943 | 0.795571 | 0.908389449 |
| 960 | 0.952787327 | −0.90555475 | −0.17381408 | 0.06786323 |
| 962 | 1.836429446 | 0.208275147 | −0.14300625 | 1.067462181 |
| 965 | 1.9158432 | 0.35211823 | −1.02174589 | 0.625657932 |
| 967 | 1.383869627 | 0.274520494 | −0.11659267 | 0.840327437 |
| 969 | −0.445579934 | −1.68867059 | −0.5241276 | 2.233793943 |
| 971 | 0.736419048 | 0.409875189 | −0.63140848 | 0.034514594 |
| 973 | 1.073465817 | 2.18418874 | 2.01361447 | −0.93754437 |
| 974 | 0.130904221 | 1.882440008 | 1.85101055 | 0.112524893 |
| 976 | −0.236681385 | −0.09745533 | 0.1779313 | 2.08923366 |
| 977 | 0.904402612 | 0.936956925 | 0.87731788 | 0.102346515 |
| 978 | 2.201759817 | 2.123549573 | 3.7881607 | 2.358768953 |
| 980 | 1.784266982 | 1.845281076 | 3.42873622 | −0.31098233 |
| 981 | −0.225023329 | 0.087962898 | −0.29053012 | 0.514272787 |
| 982 | −0.231175318 | −0.0159671 | 1.27391892 | 1.090487158 |
| 983 | 0.889215441 | 0.24321159 | 0.06877629 | 0.816247177 |
| 985 | 1.864634345 | 0.133647536 | 1.29803755 | 1.951226654 |
| 986 | 0.511450274 | −2.33512445 | −0.56246315 | −0.42184152 |
| 987 | 0.847260813 | 0.368638185 | 0.4114346 | 0.219336109 |
| 988 | 1.596170102 | 1.592158381 | 0.30052357 | 0.283467897 |
| 993 | −3.549941097 | −2.6847861 | −0.17502622 | 1.41034664 |
| 994 | 0.445802042 | 0.899738574 | 0.61059602 | 0.323194673 |
| 995 | 0.949498724 | 0.357111159 | 0.28371155 | −0.14156488 |
| 998 | 2.197271885 | 1.578871826 | 0.90563334 | 1.056619658 |
| 998 | 2.197271885 | 1.578871826 | 0.90563334 | 1.056619658 |
| 1000 | 1.456120673 | 0.626173572 | 0.07683183 | −0.43324035 |
| 1001 | −0.440378333 | 0.918089245 | 0.03050609 | −1.62235977 |
| 1002 | 0.819929066 | 0.459101825 | −0.09227583 | 0.324342063 |
| 1003 | 1.64412453 | −0.09343399 | 0.70197344 | 3.710273595 |
| 1004 | 0.796928207 | 0.459954079 | −0.88538616 | 0.152000937 |
| 1005 | 0.044923203 | −0.19994963 | 0.60082875 | 0.258347835 |
| 1006 | −0.320452673 | −0.33232662 | −0.52315783 | 1.406273663 |
| 1007 | 4.040291133 | 3.474551355 | 3.57146797 | 3.565985043 |
| 1008 | 0.764519082 | 0.917635102 | 2.88258762 | 2.319622474 |
| 1009 | −0.071112206 | 0.539362906 | 2.98048732 | 0.580423329 |
| 1010 | −0.689737481 | 0.547928768 | 1.98805626 | −0.76653376 |
| 1011 | 0.343668917 | 0.931501008 | −0.05483722 | 0.395369857 |
| 1012 | 1.926713131 | 0.124849138 | −0.09654906 | 1.126499382 |
| 1016 | 0.124247716 | 0.193102712 | 0.39003599 | 1.737670628 |
| 1017 | 0.131224136 | 0.21510779 | −1.70996346 | 0.964902175 |
| 1018 | 0.499624069 | 0.962843507 | 0.77617619 | −1.15296947 |
| 1019 | 0.813491983 | 0.322635656 | 0.02800396 | 0.599500927 |
| 1020 | 0.715468114 | 1.015469049 | 1.45994989 | 0.352548581 |
| 1021 | −1.176339404 | 1.539767848 | −0.14427147 | 1.389902738 |
| 1022 | 1.364966718 | 1.690570939 | 2.05914194 | 2.364375484 |
| 1023 | 2.154641091 | 0.800066339 | 0.85365652 | 0.965810338 |
| 1024 | 2.302280068 | 1.252164308 | 1.73414439 | 1.549538352 |
| 1025 | 1.878331515 | 1.287303121 | 0.11530502 | 1.132065786 |
| 1026 | 2.97722987 | 2.096441965 | 3.87172868 | 0.550274831 |
| 1027 | 2.474381478 | 1.950326182 | 3.81861867 | 1.366897355 |
| 1028 | 1.778414353 | 3.114931059 | 4.47690731 | 6.054314034 |
| 1029 | 3.672910795 | 2.760483725 | 3.26915034 | 3.042677588 |
| 1030 | −0.604959715 | −2.13584086 | 0.8687855 | 0.024144016 |
| 1031 | 2.012732245 | 2.293857161 | 0.54405555 | 1.261882121 |
| 1032 | −1.086688867 | 0.953083194 | 2.92177054 | 0.876865185 |
| 1033 | 1.617520676 | 1.008017006 | 2.21183536 | −0.1288484 |
| 1035 | 2.506372295 | 3.419954592 | 4.58206882 | 4.134341651 |
| 1036 | −0.675805062 | −0.15357004 | 0.94597719 | 3.966016669 |
| 1037 | −0.275092569 | −0.67687665 | −0.52763797 | 1.489972106 |
| 1038 | 2.753559643 | 3.81185814 | 2.71344734 | 2.243351472 |
| 1039 | 0.65087433 | 0.026885305 | −0.0153558 | 0.011870127 |
| 1040 | 0.141526548 | −1.65455278 | 0.50170705 | −1.90794 |
| 1041 | 0.458680435 | −0.69730218 | −0.48806249 | 0.586073092 |
| 1042 | −0.513264812 | −0.22001961 | 0.36339519 | 1.03208599 |
| 1043 | −1.497887014 | −1.76116109 | −0.76634926 | 1.137002742 |
| 1045 | 2.863652137 | 1.96790869 | 0.43661485 | −0.44756897 |
| 1046 | 0.981194248 | 1.73892162 | 2.21166953 | 2.738129365 |
| 1047 | 0.981194248 | 1.73892162 | 2.21166953 | 2.738129365 |
| 1051 | 0.70261974 | −0.22197386 | 0.19710806 | −2.37196477 |
| 1052 | 0.662126832 | 0.741436531 | 0.61672724 | 0.289359903 |
| 1053 | 0.87463644 | −0.19717783 | 1.2664131 | −0.4187507 |

TABLE 7-continued

| Material No. | MORV value for Equation a.) | MORV Value for Equation b.) | MORV Value for Equation c.) | MORV value for Equation d.) |
|---|---|---|---|---|
| 1054 | 0.284558077 | −1.46754925 | −0.03124571 | 0.587227244 |
| 1055 | 0.885837831 | −0.91907796 | −0.45817355 | −1.1936897 |
| 1057 | 0.790964847 | 1.387925398 | −0.18370692 | 1.302393792 |
| 1058 | −1.052897931 | −0.85226912 | 0.90324527 | −1.09684959 |
| 1059 | −0.871565421 | −0.17856476 | 1.51267137 | −1.52734367 |
| 1060 | 3.311161199 | 3.074783921 | 2.10199297 | 1.822541682 |
| 1061 | −0.655128061 | 0.497032417 | 0.92381279 | −0.56348341 |
| 1062 | −0.443129049 | 0.96200606 | 1.51641349 | −0.22974864 |
| 1063 | 1.385675542 | 0.738759296 | 1.1677069 | 0.501211562 |
| 1064 | 1.670680003 | −0.20756775 | −0.73755051 | −0.84924056 |
| 1065 | 1.43532227 | 1.656262941 | −1.09448841 | 1.674272267 |
| 1066 | 1.670680003 | 1.284791101 | 0.14864516 | −0.84985664 |
| 1067 | 2.237616041 | 0.345329863 | −0.60597063 | −0.71581056 |
| 1069 | −0.24632881 | −0.23975349 | −0.01449288 | 0.574861147 |
| 1070 | 1.670680003 | 0.070165381 | −0.64700996 | −0.85055617 |
| 1071 | −1.02687397 | −0.36244273 | 0.13010074 | 0.535909448 |
| 1072 | 1.670680003 | 1.94609957 | 0.19633838 | 1.14825764 |
| 1073 | 2.237616041 | 1.438074134 | 0.31117554 | −0.71786492 |
| 1074 | −0.192632911 | 0.142411101 | 0.79310676 | 0.125548041 |
| 1075 | 0.909356011 | 0.368597887 | 1.03689838 | 1.001198751 |
| 1076 | 0.812238101 | 0.195908668 | 0.21564664 | 0.219336109 |
| 1077 | 0.325255266 | 1.131242708 | −2.79377204 | −0.62848261 |
| 1078 | 0.325255266 | 1.131242708 | −2.79377204 | −0.62848261 |
| 1079 | 0.85330799 | −0.6855194 | −0.90046979 | −0.46415796 |
| 1081 | −0.131519393 | 0.731836014 | 0.81604919 | −1.29993979 |
| 1082 | 0.744770665 | 0.155243763 | −1.8029919 | 1.023503542 |
| 1083 | 1.415726941 | 0.086297223 | 3.43559555 | −0.12964168 |
| 1084 | 0.161304111 | 0.66712144 | 0.58401752 | 0.373809692 |
| 1085 | −0.72863532 | −0.2873027 | 2.21251376 | 3.003873022 |
| 1088 | −1.1773616 | −0.23258175 | 0.40529195 | 0.994988969 |
| 1089 | 2.769817302 | 1.661618789 | 3.97585272 | 1.059236597 |
| 1090 | 3.052627325 | 0.420821685 | −0.57080756 | 1.751222205 |
| 1091 | −3.379896722 | −3.71174986 | 2.53586709 | 0.644702886 |
| 1093 | 0.72304265 | 1.667011476 | 2.53982093 | 2.7903213 |
| 1095 | 0.744219765 | 1.372184572 | 0.15852396 | 1.126053442 |
| 1097 | 4.407270402 | 2.670641491 | 5.02636153 | 5.361271976 |
| 1098 | −1.85804837 | −2.59071226 | −0.46522239 | 0.655734646 |
| 1099 | 0.745797788 | −0.20547378 | 4.27836342 | 4.646390386 |
| 1102 | 2.068748434 | −0.24299896 | 0.07214682 | −1.11758276 |
| 1104 | 1.018876287 | 0.025163067 | −0.1106021 | 0.838914654 |
| 1105 | 2.387326861 | 3.865456674 | 2.2251199 | 0.728667998 |
| 1107 | 2.352582059 | 2.595496601 | 3.20492728 | 2.844590737 |
| 1110 | 0.302703712 | 0.599942142 | −0.25637571 | −0.03195517 |
| 1111 | 0.750930333 | 0.656784751 | 1.68326413 | 0.329846578 |
| 1112 | −0.205527848 | 0.287622624 | −0.00340777 | 0.59203719 |
| 1115 | 0.999825037 | 0.662221152 | 0.43571192 | 0.342558518 |
| 1116 | 0.873381263 | 1.544324176 | 0.13703728 | −0.38172701 |
| 1117 | −0.682983903 | 1.798204302 | 2.42110319 | −0.39173951 |
| 1118 | 0.069769623 | 0.496895599 | 0.67857133 | −0.14954441 |
| 1119 | −0.671908804 | −0.65984824 | 0.5238174 | −0.85314111 |
| 1120 | 0.953790113 | 1.106552668 | 3.00006904 | 1.585038764 |
| 1121 | −1.184630973 | 2.476138312 | 4.80971952 | 2.450646806 |
| 1122 | −1.02687397 | −0.36244273 | 0.13010074 | 0.535909448 |
| 1125 | 0.387315524 | −0.36101406 | 1.14153708 | −0.75303953 |
| 1126 | 1.021783831 | −0.0070257 | −0.14327539 | 3.954381426 |
| 1127 | 0.990592079 | 0.305612583 | 0.14155512 | −0.29526854 |
| 1128 | 0.990592079 | 0.305612583 | 0.14155512 | −0.29526854 |
| 1129 | 3.18966648 | 3.284362987 | 4.49398568 | 3.950809104 |
| 1131 | 1.650621055 | 1.545704806 | 2.37535081 | 1.259373143 |
| 1133 | −1.519747805 | −0.60804324 | 0.02746106 | 0.590708892 |
| 1134 | 0.815942067 | −0.16126019 | −0.54117238 | 0.613093526 |
| 1135 | 0.626973385 | 1.998305877 | 2.61706075 | 1.570404253 |
| 1136 | 2.812199484 | 1.353198146 | 2.05618426 | 1.869204406 |
| 1137 | 2.208307057 | 1.387136198 | 3.21521374 | 2.069795393 |
| 1138 | 1.670680003 | 1.316442078 | 0.14822999 | −0.46985154 |
| 1139 | 1.408517438 | 0.890457374 | 1.24524408 | 0.685687797 |
| 1140 | 2.765860952 | 2.525539595 | 4.12464228 | 3.833744077 |
| 1141 | −0.484394663 | 0.677713073 | −0.22783646 | −0.37267608 |
| 1142 | 2.54335679 | 4.298105601 | 3.36234238 | 2.684404542 |
| 1143 | 4.204367611 | 3.062126931 | 3.4234313 | 2.072899554 |
| 1144 | 2.479165229 | 3.226545885 | 4.65897152 | 4.952127235 |
| 1145 | 2.479158921 | 3.226545885 | 4.65897152 | 4.952127235 |
| 1146 | 0.774334025 | 1.075800774 | 1.06893156 | 1.011113116 |

TABLE 7-continued

| Material No. | MORV value for Equation a.) | MORV Value for Equation b.) | MORV Value for Equation c.) | MORV value for Equation d.) |
|---|---|---|---|---|
| 1147 | 0.844648531 | 1.21935371 | 2.59138595 | 0.805938034 |
| 1148 | 2.906236436 | 1.550674121 | 3.56959167 | 2.832126896 |
| 1149 | 2.837627443 | 3.707154326 | 4.53384262 | 2.625871865 |
| 1151 | 1.283224242 | 2.096933397 | 1.288975199 | 1.960766680 |
| 1152 | 1.978618006 | 2.732613301 | 2.195942117 | 1.683156477 |

Suitable Fibrous Structures and Equipment

A non-limiting list of suppliers of suitable fibrous structures, for example sanitary tissue products, polybags, and/or paper cartons that can be used in the manufacture of the fibrous structures of the present invention is as follows: Procter & Gamble of Cincinnati, Ohio, USA; International Paper Products of Memphis, Tenn. USA; and Kimberly Clark, of Irving, Tex., USA. Suitable equipment and processes for making such fibrous structures can be obtained from Fameccanica Group of Pescara, Italy. Suitable equipment and processes for adding the malodor reduction materials to said fibrous structures can be obtained from Nordson of Duluth Ga., USA.

Compositions and Methods

In one example, a fibrous structure of the present invention, for example a sanitary tissue product, for example a toilet tissue, a polybag, and/or paper carton, comprises:
  a) a sum total of from about 0.0001 mg to about 50 mg, and/or from about 0.001 mg to about 7 mg, and/or from about 0.005 mg to about 5 mg, and/or from about 0.01 mg to about 4 mg of one or more malodor reduction materials, and/or 1 to about 20 malodor reduction materials, and/or 1 to about 15 malodor reduction materials, and/or 1 to about 10 malodor reduction materials, and/or each of said malodor reduction materials having a MORV of at least 0.5, and/or from 0.5 to 10, and/or from 1 to 10, and/or from 1 to 5, and/or each of said malodor reduction materials having a Universal MORV, or said sum total of malodor reduction materials having a Blocker Index of less than 3, and/or less than about 2.5 and/or less than about 2 and and/or less than about 1 and/or 0 and/or a Blocker Index average of 3 to about 0.001. As the other ranges above are tightened, the malodor reduction material(s) provide less and less of a scent impact, while continuing to counteract malodors.

In one aspect of said fibrous structure, said sum total of malodor reduction materials has a Blocker Index of less than 3, and/or less than about 2.5 and/or less than about 2 and/or less than about 1 and/or 0 and/or a Blocker Index average of 3 to about 0.001.

In one aspect of said fibrous structure, each of said malodor reduction materials has a MORV of at least 0.5, and/or from 0.5 to 10, and/or from 1 to 10, and/or from 1 to 5, and/or each of said malodor reduction materials having a Universal MORV.

In one aspect of said fibrous structure, said sum total of malodor reduction materials has a Fragrance Fidelity Index average of 3 to about 0.001 Fragrance Fidelity Index, and/or each malodor reduction material in said sum total of malodor reduction materials has a Fragrance Fidelity Index of less than 3, and/or less than 2, and/or less than 1 and/or each malodor reduction material in said sum total of malodor reduction materials has a Fragrance Fidelity Index of 0.

In one aspect of said fibrous structure, said fibrous structure comprises a perfume, the ratio of said perfume to said sum total of malodor reduction material is from about 300,000:1 to about 1:1 and/or from about 100,000:1 to about 1:1 and/or from about 50,000:1 to about 1:1 and/or from about 15,000:1 to about 1:1 and/or from about 5,000:1 to about 1:1 and/or from about 1,000:1 to about 1:1 and/or from about 50:1 to about 1:1, and/or from about 20:1 to about 1:1.

In one aspect of said fibrous structure, said fibrous structure comprises one or more malodor reduction materials; and/or one or more malodor reduction materials selected from the group consisting of Table 1 materials numbers 1, 2, 3, 4, 7, 9, 10, 11, 13, 14, 16, 17, 18, 21, 22, 23, 25, 28, 29, 30, 31, 32, 33, 34, 35, 36, 37, 38, 39, 42, 43, 47, 48, 49, 50, 52, 57, 61, 62, 63, 64, 65, 67, 68, 69, 70, 71, 74, 75, 76, 77, 78, 79, 80, 82, 83, 85, 91, 92, 93, 98, 100, 101, 102, 103, 104, 105, 106, 108, 109, 110, 112, 113, 114, 117, 119, 120, 122, 123, 126, 128, 130, 134, 135, 137, 140, 141, 142, 143, 145, 146, 148, 149, 152, 153, 155, 156, 158, 159, 161, 162, 167, 168, 170, 174, 175, 176, 177, 178, 179, 182, 183, 184, 185, 186, 187, 189, 190, 192, 193, 195, 196, 197, 199, 206, 208, 209, 210, 211, 212, 215, 218, 221, 227, 228, 229, 230, 231, 233, 234, 238, 242, 243, 244, 246, 247, 249, 252, 253, 254, 256, 259, 260, 261, 263, 267, 269, 271, 274, 276, 277, 278, 280, 281, 285, 286, 288, 289, 290, 292, 293, 294, 295, 296, 300, 301, 303, 307, 316, 317, 318, 321, 322, 323, 324, 325, 328, 329, 330, 331, 332, 333, 334, 335, 336, 338, 339, 342, 343, 344, 347, 349, 350, 352, 353, 356, 358, 359, 360, 361, 362, 363, 364, 368, 369, 370, 371, 372, 373, 374, 375, 377, 378, 381, 385, 386, 388, 390, 391, 394, 397, 398, 407, 413, 414, 415, 416, 417, 418, 421, 424, 425, 426, 428, 429, 432, 436, 441, 444, 445, 449, 450, 453, 457, 459, 461, 462, 463, 464, 465, 466, 467, 468, 470, 471, 473, 474, 475, 478, 479, 480, 482, 484, 485, 486, 487, 488, 491, 493, 497, 498, 501, 502, 503, 505, 519, 520, 521, 524, 527, 529, 530, 531, 532, 534, 537, 541, 544, 546, 548, 550, 551, 552, 553, 555, 558, 559, 560, 561, 562, 563, 565, 566, 567, 568, 569, 570, 571, 572, 573, 574, 577, 578, 580, 581, 582, 584, 586, 587, 589, 591, 592, 594, 595, 599, 600, 601, 603, 604, 606, 607, 608, 609, 610, 611, 612, 613, 614, 615, 616, 618, 620, 621, 624, 625, 626, 627, 628, 631, 632, 633, 635, 636, 638, 639, 644, 649, 650, 653, 655, 658, 659, 660, 661, 663, 668, 671, 673, 674, 675, 676, 677, 678, 679, 680, 681, 682, 683, 684, 686, 691, 692, 693, 694, 696, 697, 698, 700, 702, 704, 706, 707, 708, 709, 710, 711, 712, 713, 714, 715, 716, 717, 718, 719, 720, 721, 722, 723, 724, 725, 726, 727, 730, 731, 733, 735, 736, 738, 741, 742, 746, 748, 750, 752, 754, 757, 758, 763, 764, 766, 767, 768, 769, 770, 771, 772, 774, 775, 776, 778, 781, 782, 786, 788, 791, 792, 800, 802, 803, 804, 805, 806, 807, 814, 821, 824, 826, 827, 828, 829, 831, 833, 834, 837, 839, 840, 849, 850, 852, 856, 864, 865, 866, 868, 869, 870, 871, 872, 873, 876, 877, 878, 879, 881, 884, 885, 886, 890, 892, 893, 894, 897, 905, 908, 912, 913, 914, 916, 919, 920, 922, 923, 924, 925, 926, 927, 928, 929, 930, 933, 937, 939, 941, 942, 943, 945, 946, 947, 948, 950, 951, 953, 954, 955, 959, 962, 965, 967, 969, 973, 974, 976, 978, 980, 982, 985, 988, 993, 998, 1000, 1003, 1006, 1007, 1008, 1009, 1010, 1012, 1016, 1020, 1021, 1022, 1023, 1024, 1025, 1026, 1027, 1028, 1029, 1031, 1032, 1033, 1035, 1036, 1037, 1038, 1042, 1043, 1045, 1046, 1047, 1053, 1057, 1059, 1060, 1062, 1063, 1064, 1065, 1066, 1067, 1070, 1072, 1073, 1075, 1077, 1078, 1082, 1083, 1085, 1089, 1090, 1091, 1093, 1095, 1097, 1099, 1102, 1104, 1105, 1107, 1111, 1113, 1116, 1117, 1120, 1121, 1125, 1126, 1129, 1131, 1135, 1136, 1137, 1138, 1139, 1140, 1142, 1143, 1144, 1145, 1146, 1147, 1148, 1149, 1151, 1152, Table 2 materials numbers 2, 23, 141, 185, 227, 230, 246, 248, 343, 359, 565, 631, 659, 674, 678, 679, 715, 758, 1028, 1097, Table 3 materials numbers 12, 19, 20, 24, 26, 27, 53, 54, 55, 59, 72, 73, 81, 84, 96, 97, 107, 111, 115, 116, 125, 133, 147, 150, 151, 154, 157, 163, 166, 169, 181, 191, 194, 198, 201, 204, 205, 213, 214, 232, 237, 239, 255, 258, 264, 270, 273, 275, 282, 283, 284, 287, 302, 306, 308, 310, 312, 314, 319, 346, 354, 355, 365, 366, 376, 379, 387, 400, 412, 419, 420, 437, 438, 439, 440, 442, 443, 447, 448, 454, 455, 469, 472, 477, 481, 492, 495, 496, 504, 509, 510, 512, 515, 517, 518, 522, 525, 526, 528, 535, 536, 538, 540, 542, 547, 549, 554, 556, 557, 575, 576, 579, 583, 585, 588, 602, 605, 617, 619, 640, 641, 645, 647, 651, 652, 662, 664, 665, 667, 672, 687, 699, 701, 703, 740, 743, 744, 745, 755, 760, 761, 777, 779, 784, 789, 796, 797, 799, 808, 810, 811, 812, 817, 819, 820, 832, 835, 836, 838, 845, 846, 847, 848, 851, 858, 875, 880, 882, 883, 888, 889, 891, 899, 900, 901, 902, 903, 904, 909, 918, 921, 931, 940, 956, 958, 960, 971, 977, 981, 983, 986, 987, 994, 995, 1001, 1002, 1004, 1005, 1011, 1017, 1018, 1019, 1030, 1039, 1040, 1041, 1051, 1052, 1054, 1055, 1058, 1061, 1069, 1071, 1074, 1076, 1079, 1081, 1084, 1088, 1098, 1110, 1112, 1115, 1118, 1119, 1122, 1127, 1128, 1133, 1134, 1141, and mixtures thereof; and/or said one or more malodor reduction materials is selected from the group consisting of Table 1 materials numbers 1, 2, 3, 4, 7, 9, 10, 11, 13, 14, 16, 17, 18, 21, 22, 23, 25, 28, 29, 30, 31, 32, 33, 34, 35, 36, 37, 38, 39, 42, 43, 47, 48, 49, 50, 52, 57, 61, 62, 63, 64, 65, 67, 68, 69, 70, 71, 74, 75, 76, 77, 78, 79, 80, 82, 83, 85, 91, 92, 93, 98, 100, 101, 102, 103, 104, 105, 106, 108, 109, 110, 112, 113, 114, 117, 119, 120, 122, 123, 126, 128, 130, 134, 135, 137, 140, 141, 142, 143, 145, 146, 148, 149, 152, 153, 155, 156, 158, 159, 161, 162, 167, 168, 170, 174, 175, 176, 177, 178, 179, 182, 183, 184, 185, 186, 187, 189, 190, 192, 193, 195, 196, 197, 199, 206, 208, 209, 210, 211, 212, 215, 218, 221, 227, 228, 229, 230, 231, 233, 234, 238, 242, 243, 244, 246, 247, 249, 252, 253, 254, 256, 259, 260, 261, 263, 267, 269, 271, 274, 276, 277, 278, 280, 281, 285, 286, 288, 289, 290, 292, 293, 294, 295, 296, 300, 301, 303, 307, 316, 317, 318, 321, 322, 323, 324, 325, 328, 329, 330, 331, 332, 333, 334, 335, 336, 338, 339, 342, 343, 344, 347, 349, 350, 352, 353, 356, 358, 359, 360, 361, 362, 363, 364, 368, 369, 370, 371, 372, 373, 374, 375, 377, 378, 381, 385, 386, 388, 390, 391, 394, 397, 398, 407, 413, 414, 415, 416, 417, 418, 421, 424, 425, 426, 428, 429, 432, 436, 441, 444, 445, 449, 450, 453, 457, 459, 461, 462, 463, 464, 465, 466, 467, 468, 470, 471, 473, 474, 475, 478, 479, 480, 482, 484, 485, 486, 487, 488, 491, 493, 497, 498, 501, 502, 503, 505, 519, 520, 521, 524, 527, 529, 530, 531, 532, 534, 537, 541, 544, 546, 548, 550, 551, 552, 553, 555, 558, 559, 560, 561, 562, 563, 565, 566, 567, 568, 569, 570, 571, 572, 573, 574, 577, 578, 580, 581, 582, 584, 586, 587, 589, 591, 592, 594, 595, 599, 600, 601, 603, 604, 606, 607, 608, 609, 610, 611, 612, 613, 614, 615, 616, 618, 620, 621, 624, 625, 626, 627, 628, 631, 632, 633, 635, 636, 638, 639, 644, 649, 650, 653, 655, 658, 659, 660, 661, 663, 668, 671, 673, 674, 675, 676, 677, 678, 679, 680, 681, 682, 683, 684, 686, 691, 692, 693, 694, 696, 697, 698, 700, 702, 704, 706, 707, 708, 709, 710, 711, 712, 713, 714, 715, 716, 717, 718, 719, 720, 721, 722, 723, 724, 725, 726, 727, 730, 731, 733, 735, 736, 738, 741, 742, 746, 748, 750, 752, 754, 757, 758, 763, 764, 766, 767, 768, 769, 770, 771, 772, 774, 775, 776, 778, 781, 782, 786, 788, 791, 792, 800, 802, 803, 804, 805, 806, 807, 814, 821, 824, 826, 827, 828, 829, 831, 833, 834, 837, 839, 840, 849, 850, 852, 856, 864, 865, 866, 868, 869, 870, 871, 872, 873, 876, 877, 878, 879, 881, 884, 885, 886, 890, 892, 893, 894, 897, 905, 908, 912, 913, 914, 916, 919, 920, 922, 923, 924, 925, 926, 927, 928, 929, 930, 933, 937, 939, 941, 942, 943, 945, 946, 947, 948, 950, 951, 953, 954, 955, 959, 962, 965, 967, 969, 973, 974, 976, 978, 980, 982, 985, 988, 993, 998, 1000, 1003, 1006, 1007, 1008, 1009, 1010, 1012, 1016, 1020, 1021, 1022, 1023, 1024, 1025, 1026, 1027, 1028, 1029, 1031, 1032, 1033, 1035, 1036, 1037, 1038, 1042, 1043, 1045, 1046, 1047, 1053, 1057, 1059, 1060, 1062, 1063, 1064, 1065, 1066, 1067, 1070, 1072, 1073, 1075, 1077, 1078, 1082, 1083, 1085, 1089, 1090, 1091, 1093, 1095, 1097, 1099, 1102, 1104, 1105, 1107, 1111, 1113, 1116, 1117, 1120, 1121, 1125, 1126, 1129, 1131, 1135, 1136, 1137, 1138, 1139, 1140, 1142, 1143, 1144, 1145, 1146, 1147, 1148, 1149, 1151, 1152, Table 2 materials numbers 2, 23, 141, 185, 227, 230, 246, 248, 343, 359, 565, 631, 659, 674, 678, 679, 715, 758, 1028, 1097, and mixtures thereof and/or said one or more malodor reduction materials is selected from the group consisting of Table 4 materials numbers 7, 14, 39, 48, 183, 199, 206, 212, 215, 229, 260, 261, 281, 329, 335, 353, 360, 441, 484, 487, 488, 501, 566, 567, 569, 570, 573, 574, 603, 616, 621, 624, 627, 632, 663, 680, 684, 694, 696, 708, 712, 714, 726, 750, 764, 775, 776, 788, 804, 872, 919, 927, 933, 978, 1007, 1022, 1024, 1027, 1029, 1035, 1038, 1060, 1089, 1107, 1129, 1131, 1136, 1137, 1140, 1142, 1143, 1144, 1145, 1148, 1149, Table 5 material number 248, and mixtures thereof, and/or said one or more malodor reduction materials is selected from the group consisting of Table 4 material numbers 261, 680, 788, 1129, 1148, 1149, 1151, 1152 and mixtures thereof.

In one aspect of said fibrous structure, said fibrous structure comprises a malodor reduction material wherein one or more of said malodor reduction materials has a log P≥3, and/or at least 1% of said malodor reduction materials have a log P≥3, and/or at least 10% of said malodor reduction materials have a log P≥3, and/or 100% of said malodor reduction materials have a log P≥3.

In one aspect of said fibrous structure, from about 1% to about 99% of said malodor reduction materials have a log P≥3, and/or said one or more malodor reduction materials are selected from the group consisting of Table 1 material numbers 1; 2; 3; 7; 9; 10; 11; 13; 14; 18; 21; 22; 23; 25; 28; 29; 30; 31; 32; 33; 35; 36; 38; 39; 47; 48; 49; 50; 52; 57; 62; 63; 64; 67; 68; 69; 71; 74; 75; 76; 77; 78; 79; 80; 83; 85; 91; 92; 93; 100; 101; 102; 103; 104; 105; 109; 114; 119; 120; 122; 123; 128; 134; 135; 137; 140; 142; 145; 148; 149; 152; 153; 158; 159; 161; 162; 174; 175; 176; 177; 178; 182; 183; 184; 185; 186; 189; 192; 195; 196; 197; 206; 208; 209; 210; 211; 212; 215; 221; 227; 228; 229; 230; 231; 233; 234; 238; 242; 243; 244; 246; 252; 253; 260; 261; 263; 267; 269; 271; 274; 276; 277; 280; 285; 289; 290; 292; 293; 294; 295; 296; 300; 301; 303; 307; 316; 317; 318; 322; 324; 325; 328; 329; 330; 331; 333; 334; 335; 336; 338; 339; 342; 343; 344; 349; 352; 356; 358; 359; 360; 361; 362; 363; 364; 368; 369; 370; 371; 372; 378; 381; 385; 386; 388; 390; 391; 397; 398; 413; 414; 416; 418; 421; 424; 426; 428; 429; 432; 441; 444; 449; 453; 457; 459; 461; 462; 463; 465; 466; 467; 468; 470; 471; 473; 475; 478; 479; 480; 482; 484; 486; 487; 488; 497; 498; 501; 502; 503; 505; 519; 520; 521; 524; 529; 532; 534; 537; 541; 544; 548; 550; 552; 558; 559; 560; 561; 562; 563; 565; 566; 567; 568; 569; 570; 571; 572; 573; 574; 577; 578; 582;

584; 589; 591; 592; 594; 599; 600; 601; 603; 604; 606; 607; 608; 609; 610; 611; 613; 614; 615; 616; 618; 620; 621; 624; 625; 626; 628; 631; 632; 633; 635; 644; 650; 653; 659; 660; 661; 663; 671; 673; 674; 675; 676; 677; 678; 679; 680; 681; 684; 686; 691; 692; 693; 694; 696; 697; 698; 700; 702; 704; 706; 707; 708; 709; 710; 711; 712; 713; 714; 715; 716; 717; 718; 719; 720; 721; 722; 723; 724; 725; 726; 727; 731; 741; 746; 750; 752; 754; 757; 758; 763; 766; 769; 770; 771; 774; 775; 776; 778; 781; 782; 788; 791; 800; 802; 804; 806; 814; 821; 826; 827; 828; 831; 837; 839; 840; 849; 850; 852; 856; 866; 868; 869; 870; 871; 872; 873; 876; 877; 878; 879; 881; 884; 885; 886; 890; 892; 893; 894; 905; 908; 912; 913; 914; 916; 919; 920; 922; 925; 926; 927; 930; 933; 939; 941; 942; 943; 945; 947; 948; 950; 951; 953; 954; 959; 965; 967; 973; 978; 985; 988; 998; 1000; 1003; 1006; 1007; 1008; 1009; 1010; 1016; 1022; 1023; 1024; 1025; 1028; 1029; 1031; 1032; 1033; 1035; 1038; 1045; 1046; 1047; 1053; 1057; 1060; 1062; 1063; 1065; 1067; 1070; 1073; 1075; 1077; 1078; 1082; 1089; 1090; 1093; 1095; 1097; 1099; 1102; 1104; 1105; 1107; 1116; 1120; 1121; 1126; 1129; 1131; 1135; 1136; 1137; 1138; 1140; 1142; 1143; 1144; 1145; 1147; 1148; 1149; 1151; 1152; Table 2 material numbers 2; 23; 185; 227; 230; 246; 248; 343; 359; 565; 631; 659; 674; 678; 679; 715; 758; 1028; 1097; Table 3 material numbers 1; 9; 12; 13; 19; 20; 21; 24; 25; 27; 32; 38; 54; 55; 59; 64; 68; 71; 72; 79; 81; 83; 85; 100; 105; 109; 111; 114; 119; 133; 134; 135; 137; 140; 142; 147; 148; 150; 151; 152; 153; 154; 157; 159; 162; 178; 181; 189; 191; 192; 195; 197; 204; 211; 228; 231; 233; 234; 237; 238; 242; 246; 252; 264; 270; 273; 275; 277; 283; 285; 289; 290; 292; 293; 295; 300; 301; 302; 306; 308; 310; 312; 319; 322; 325; 331; 333; 334; 336; 338; 339; 344; 346; 354; 355; 356; 358; 361; 362; 363; 370; 371; 372; 378; 381; 385; 387; 388; 390; 412; 413; 418; 420; 428; 429; 432; 437; 438; 444; 447; 448; 454; 455; 457; 461; 465; 467; 472; 477; 478; 479; 480; 481; 482; 495; 496; 497; 502; 503; 504; 509; 510; 512; 515; 517; 518; 522; 525; 529; 535; 536; 537; 540; 541; 544; 550; 557; 558; 559; 560; 561; 568; 571; 572; 575; 589; 592; 594; 599; 600; 602; 604; 609; 619; 620; 625; 626; 633; 641; 644; 645; 650; 653; 662; 667; 672; 673; 675; 676; 681; 686; 687; 693; 697; 698; 700; 703; 704; 706; 707; 716; 717; 718; 722; 725; 744; 745; 746; 757; 769; 771; 779; 782; 799; 806; 819; 820; 827; 828; 836; 838; 839; 847; 850; 875; 878; 879; 880; 881; 888; 889; 890; 891; 893; 899; 900; 901; 903; 909; 912; 914; 920; 922; 930; 939; 940; 941; 945; 947; 948; 953; 954; 958; 959; 960; 965; 967; 971; 986; 987; 994; 995; 998; 1000; 1001; 1003; 1005; 1008; 1009; 1010; 1011; 1017; 1018; 1023; 1031; 1032; 1046; 1047; 1051; 1052; 1053; 1054; 1055; 1057; 1058; 1061; 1062; 1063; 1074; 1075; 1076; 1082; 1088; 1093; 1095; 1099; 1102; 1104; 1105; 1115; 1116; 1120; 1127; 1128; 1134; 1135; 1141; 1147; 1148, 1149, and mixtures thereof; and/or said one or more malodor reduction materials is selected from the group consisting of Table 1 material numbers 1; 2; 3; 7; 9; 10; 11; 13; 14; 18; 21; 22; 23; 25; 28; 29; 30; 31; 32; 33; 35; 36; 38; 39; 47; 48; 49; 50; 52; 57; 62; 63; 64; 67; 68; 69; 71; 74; 75; 76; 77; 78; 79; 80; 83; 85; 91; 92; 93; 100; 101; 102; 103; 104; 105; 109; 114; 119; 120; 122; 123; 128; 134; 135; 137; 140; 142; 145; 148; 149; 152; 153; 158; 159; 161; 162; 174; 175; 176; 177; 178; 182; 183; 184; 185; 186; 189; 192; 195; 196; 197; 206; 208; 209; 210; 211; 212; 215; 221; 227; 228; 229; 230; 231; 233; 234; 238; 242; 243; 244; 246; 252; 253; 260; 261; 263; 267; 269; 271; 274; 276; 277; 280; 285; 289; 290; 292; 293; 294; 295; 296; 300; 301; 303; 307; 316; 317; 318; 322; 324; 325; 328; 329; 330; 331; 333; 334; 335; 336; 338; 339; 342; 343; 344; 349; 352; 356; 358; 359; 360; 361; 362; 363; 364; 368; 369; 370; 371; 372; 378; 381; 385; 386; 388; 390; 391; 397; 398; 413; 414; 416; 418; 421; 424; 426; 428; 429; 432; 441; 444; 449; 453; 457; 459; 461; 462; 463; 465; 466; 467; 468; 470; 471; 473; 475; 478; 479; 480; 482; 484; 486; 487; 488; 497; 498; 501; 502; 503; 505; 519; 520; 521; 524; 529; 532; 534; 537; 541; 544; 548; 550; 552; 558; 559; 560; 561; 562; 563; 565; 566; 567; 568; 569; 570; 571; 572; 573; 574; 577; 578; 582; 584; 589; 591; 592; 594; 599; 600; 601; 603; 604; 606; 607; 608; 609; 610; 611; 613; 614; 615; 616; 618; 620; 621; 624; 625; 626; 628; 631; 632; 633; 635; 644; 650; 653; 659; 660; 661; 663; 671; 673; 674; 675; 676; 677; 678; 679; 680; 681; 684; 686; 691; 692; 693; 694; 696; 697; 698; 700; 702; 704; 706; 707; 708; 709; 710; 711; 712; 713; 714; 715; 716; 717; 718; 719; 720; 721; 722; 723; 724; 725; 726; 727; 731; 741; 746; 750; 752; 754; 757; 758; 763; 766; 769; 770; 771; 774; 775; 776; 778; 781; 782; 788; 791; 800; 802; 804; 806; 814; 821; 826; 827; 828; 831; 837; 839; 840; 849; 850; 852; 856; 866; 868; 869; 870; 871; 872; 873; 876; 877; 878; 879; 881; 884; 885; 886; 890; 892; 893; 894; 905; 908; 912; 913; 914; 916; 919; 920; 922; 925; 926; 927; 930; 933; 939; 941; 942; 943; 945; 947; 948; 950; 951; 953; 954; 959; 965; 967; 973; 978; 985; 988; 998; 1000; 1003; 1006; 1007; 1008; 1009; 1010; 1016; 1022; 1023; 1024; 1025; 1028; 1029; 1031; 1032; 1033; 1035; 1038; 1045; 1046; 1047; 1053; 1057; 1060; 1062; 1063; 1065; 1067; 1070; 1073; 1075; 1077; 1078; 1082; 1089; 1090; 1093; 1095; 1097; 1099; 1102; 1104; 1105; 1107; 1116; 1120; 1121; 1126; 1129; 1131; 1135; 1136; 1137; 1138; 1140; 1142; 1143; 1144; 1145; 1147; 1148; 1149; 1151; 1152; Table 2 material numbers 2; 23; 185; 227; 230; 246; 248; 343; 359; 565; 631; 659; 674; 678; 679; 715; 758; 1028; 1097 and mixtures thereof and/or said one or more malodor reduction materials is selected from the group consisting of Table 4 and 5 materials numbers 7; 14; 39; 48; 183; 206; 212; 215; 229; 260; 261; 329; 335; 360; 441; 484; 487; 488; 501; 566; 567; 569; 570; 573; 574; 603; 616; 621; 624; 632; 663; 680; 684; 694; 696; 708; 712; 714; 726; 750; 775; 776; 788; 804; 872; 919; 927; 933; 978; 1007; 1022; 1024; 1029; 1035; 1038; 1060; 1089; 1107; 1129; 1131; 1136; 1137; 1140; 1142; 1143; 1144; 1145; 1148, 1149; 248; and/or said one or more malodor reduction materials is selected from the group consisting of Table 4 and 5 material numbers materials 261; 680; 788; 1129, 1148, 1149, 1151, 1152 and mixtures thereof. Materials having a log P greater than 3 will stay on a fibrous structure longer thus more of such materials will be present when needed/when the fibrous structure is used.

In one aspect of said fibrous structure, said malodor reduction materials are not selected from the group consisting of malodor reduction materials according to Tables 1-3 numbers 302; 288; 50; 157; 1017; 888; 64; 1054; 832; 375; 390; 745; 504; 505; 140; 1012; 498; 362; 103; 356; 1074; 908; 1127; 475; 918; 687; 611; 317; 9; 141; 550; 602; 913; 1005; 521; 10; 215; 370; 335; 378; 1121; 360; 565; 1136; 1129; 655; 369; 1065; 914; 757; 601; 478; 889; 891; 358; 973; 162; 554; 522; 312; 125; 26; 418; 92; 586; 1026; 218; 31; 828; 871; 829; 1066; 287; 269; 769; 701; 1118; 70; 946; 142; 109; 108 or mixtures thereof.

In one aspect of said fibrous structure, said fibrous structure is a sanitary paper product, said sanitary paper product comprising one or more layers of conventional felt-pressed tissue paper, conventional wet-pressed tissue paper, pattern densified tissue paper, starch substrates, high bulk, un-compacted tissue paper and mixtures thereof.

In one aspect of said fibrous structure, said fibrous structure is contained in a polybag or paper carton.

In one aspect of said fibrous structure, said malodor reduction materials are disposed on said polybag or paper carton, and/or on said sanitary tissue product, for example toilet tissue.

In one aspect of said fibrous structure, said fibrous structure is a fibrous structure comprising a lotion and/or surface softening chemistry (softener), such as silicone and/or quaternary ammonium compounds.

In one aspect of said fibrous structure, said fibrous structure is a fibrous structure comprising one or more adjunct ingredients selected from the group consisting of surfactants, inks, dyes, mineral oils, petrolatum, polysiloxanes, cyclodextrins, clays, silicates, aluminates, vitamins, isoflavones, flavones, metal oxides, short chain organic acids (C1-C8), triglycerides (C8-C22), and antioxidants.

In one aspect of said fibrous structure, said fibrous structure comprises an encapsulate comprising one or more of said malodor reduction material(s).

In one aspect, a method of controlling malodors comprising: contacting a fibrous structure, comprising said malodor reduction materials, with a malodor is disclosed.

Test Methods

Malodor reduction materials may be separated from mixtures, including but not limited to finished products such as consumer products and identified, by analytical methods that include GC-MS and/or NMR.

Test Method for Determining Saturation Vapour Pressure (VP)

The saturation Vapour Pressure (VP) values are computed for each PRM in the perfume mixture being tested. The VP of an individual PRM is calculated using the VP Computational Model, version 14.02 (Linux) available from Advanced Chemistry Development Inc. (ACD/Labs) (Toronto, Canada) to provide the VP value at 25° C. expressed in units of torr. The ACD/Labs' Vapor Pressure model is part of the ACD/Labs model suite.

Test Method for Determining the Logarithm of the Octanol/Water Partition Coefficient (Log P)

The value of the log of the Octanol/Water Partition Coefficient (log P) is computed for each PRM in the perfume mixture being tested. The log P of an individual PRM is calculated using the Consensus log P Computational Model, version 14.02 (Linux) available from Advanced Chemistry Development Inc. (ACD/Labs) (Toronto, Canada) to provide the unitless log P value. The ACD/Labs' Consensus log P Computational Model is part of the ACD/Labs model suite.

Test Method for the Generation of Molecular Descriptors

In order to conduct the calculations involved in the computed-value test methods described herein, the starting information required includes the identity, weight percent, and molar percent of each PRM in the perfume being tested, as a proportion of that perfume, wherein all PRMs in the perfume composition are included in the calculations. Additionally for each of those PRMs, the molecular structure, and the values of various computationally-derived molecular descriptors are also required, as determined in accordance with the Test Method for the Generation of Molecular Descriptors described herein.

For each PRM in a perfume mixture or composition, its molecular structure is used to compute various molecular descriptors. The molecular structure is determined by the graphic molecular structure representations provided by the Chemical Abstract Service ("CAS"), a division of the American Chemical Society, Columbus, Ohio, U.S.A. These molecular structures may be obtained from the CAS Chemical Registry System database by looking up the index name or CAS number of each PRM. For PRMs, which at the time of their testing are not yet listed in the CAS Chemical Registry System database, other databases or information sources may be used to determine their structures. For a PRM which has potentially more than one isomer present, the molecular descriptor computations are conducted using the molecular structure of only one of the isomers, which is selected to represent that PRM. The selection of isomer is determined by the relative amount of extension in the molecular structures of the isomers. Of all the isomers of a given PRM, it is the isomer whose molecular structure that is the most prevalent which is the one that is selected to represent that PRM. The structures for other potential isomers of that PRM are excluded from the computations. The molecular structure of the isomer that is the most prevalent is paired with the concentration of that PRM, where the concentration reflects the presence of all the isomers of that PRM that are present.

A molecule editor or molecular sketching software program, such as ChemDraw (CambridgeSoft/PerkinElmer Inc., Waltham, Mass., U.S.A.), is used to duplicate the 2-dimensional molecular structure representing each PRM. Molecular structures should be represented as neutral species (quaternary nitrogen atoms are allowed) with no disconnected fragments (e.g., single structures with no counter ions). The winMolconn program described below can convert any deprotonated functional groups to the neutral form by adding the appropriate number of hydrogen atoms and will discard the counter ion.

For each PRM, the molecular sketching software is used to generate a file which describes the molecular structure of the PRM. The file(s) describing the molecular structures of the PRMs is subsequently submitted to the computer software program winMolconn, version 1.0.1.3 (Hall Associates Consulting, Quincy, Mass., U.S.A.), in order to derive various molecular descriptors for each PRM. As such, it is the winMolconn software program which dictates the structure notations and file formats that are acceptable options. These options include either a MACCS SDF formatted file (i.e., a Structure-Data File); or a Simplified Molecular Input Line Entry Specification (i.e., a SMILES string structure line notation) which is commonly used within a simple text file, often with a file name extension. The SDF file represents each molecular structure in the format of a multi-line record, while the syntax for a SMILES structure is a single line of text with no white space. A structure name or identifier can be added to the SMILES string by including it on the same line following the SMILES string and separated by a space, e.g.: Cl=CC=CC=Cl benzene.

The winMolconn software program is used to generate numerous molecular descriptors for each PRM, which are then output in a table format. Specific molecular descriptors derived by winMolconn are subsequently used as inputs (i.e., as variable terms in mathematical equations) for a variety of computer model test methods in order to calculate values such as: saturation Vapour Pressure (VP); Boiling Point (BP); logarithm of the Octanol/Water Partition Coefficient (log P); Odour Detection Threshold (ODT); Malodour Reduction Value (MORV); and/or Universal Malodour Reduction Value (Universal MORV) for each PRM. The molecular descriptor labels used in the models' test method computations are the same labels reported by the winMolconn program, and their descriptions and definitions can be found listed in the winMolconn documentation. The following is a generic description of how to execute the winMolconn software program and generate the required molecular structure descriptors for each PRM in a composition.

Computing Molecular Structure Descriptors using win-Molconn:

1) Assemble the molecular structure for one or more perfume ingredients in the form of a MACCS Structure-Data File, also called an SDF file, or as a SMILES file.
2) Using version 1.0.1.3 of the winMolconn program, running on an appropriate computer, compute the full complement of molecular descriptors that are available from the program, using the SDF or SMILES file described above as input.
   a. The output of winMolconn is in the form of an ASCII text file, typically space delimited, containing the structure identifiers in the first column and respective molecular descriptors in the remaining columns for each structure in the input file.
3) Parse the text file into columns using a spreadsheet software program or some other appropriate technique. The molecular descriptor labels are found on the first row of the resulting table.
4) Find and extract the descriptor columns, identified by the molecular descriptor label, corresponding to the inputs required for each model.
   a. Note that the winMolconn molecular descriptor labels are case-sensitive.

MORV and Universal MORV Calculation

1.) Input Molecular Descriptor values as determined via the method above into the following four equations:

$$MORV = -8.5096 + 2.8597 \times (dxp9) + 1.1253 \times (knotpv) - 0.34484 \times (e1C2O2) - 0.00046231 \times (idw) + 3.3509 \times (idcbar) + 0.11158 \times (n2pag22) \quad \text{a)}$$

$$MORV = -5.2917 + 2.1741 \times (dxvp5) - 2.6595 \times (dxvp8) + 0.45297 \times (e1C2C2d) - 0.6202 \times (c1C2O2) + 1.3542 \times (CdCH2) + 0.68105 \times (CaasC) + 1.7129 \times (idcbar) \quad \text{b)}$$

$$MORV = -0.0035 + 0.8028 \times (SHCsatu) + 2.1673 \times (xvp7) - 1.3507 \times (c1C1C3d) + 0.61496 \times (c1C1O2) + 0.00403 \times (idc) - 0.23286 \times (nd2). \quad \text{c)}$$

$$MORV = -0.9926 - 0.03882 \times (SdO) + 0.1869 \times (Ssp3OH) + 2.1847 \times (xp7) + 0.34344 \times (e1C3O2) - 0.45767 \times (c1C2C3) + 0.7684 \times (CKetone) \quad \text{d)}$$

Equation a) relates a material's effectiveness in reducing the malodor trans-3-methyl-2-hexenoic acid (carboxylic acid based malodors)

Equation b) relates a material's effectiveness in reducing the malodor trimethylamine (amine based malodors)

Equation c) relates a material's effectiveness in reducing the malodor 3-mercapto-3-methylhexan-1-ol (thiol based malodors)

Equation d) relates a material's effectiveness in reducing the malodor skatole (indole based malodors)

2.) For purpose of the present application, a material's MORV is the highest MORV value from equations 1.)a) through 1.)d).

3.) If all MORV values from equations 1.)a) through 1.)d) above are greater than 0.5, the subject material has a Universal MORV.

Method for Assigning Fragrance Fidelity Index (FFI) and the Blocker Index (BI) for a Malodor Reduction Compound Blocker materials suitable for use in consumer products of the present invention are chosen for their ability to decrease malodor, while not interfering with perception of a fragrance. Material selection is done by assigning two indices to a test sample material from two reference scales in order to rank odor strengths. The two reference scales are the Fragrance Fidelity Index (FFI) scale and the Blocker Index (BI) scale. The FFI ranks the ability of the test sample material to impart a perceivable odor which could cause interference when combined with another fragrance and the BI ranks the ability of the test sample material to reduce malodor perception. The two methods for assigning the indices to a test sample on the FFI and the BI reference scales are given below.

Method for Assigning the FFI to Test Samples

The first step in the method for assigning an FFI on the FFI reference scale is to create the FFI reference swatches. The swatches for the scale are created by treating clean fabrics swatches with a known amount of a known concentration of an ethyl vanillin solution. Fabric swatches for this test are white knit polycotton (4 inch×4 inch) swatches from EMC ordered as PC 50/50. The supplier is instructed to strip the swatches first, stripping involves washing twice with a fragrance-free detergent and rinsing three times.

Making the FFI Reference Swatches

Make three solutions of ethyl vanillin using a 50%/50% EtOH/water as the diluent at the following concentrations: 25 ppm, 120 ppm and 1000 ppm. Pipette 13 µL of each of the three solutions into the middle of a clean swatch resulting in about a 1 cm diameter of the solution in the middle of the swatch. This will create a sensory scale of three swatches with three different odor levels based on the concentration of the solution pipetted onto the swatch. After drying for 30 minutes in a vented hood, the swatches are wrapped in aluminum foil to prevent odor contamination to the treated swatch. A clean untreated swatch is also included as the lowest anchor point of reference for odor strength on the FFI scale. The FFI reference scale swatches should be used within 0.5 to 12 hours and discarded after 12 hours. The swatches are used as scale anchor points when graders evaluate a test sample(s) and are assigned a Fragrance Fidelity Index (FFI) as show in Table 8 below.

At least four perfumers/expert graders are used to rank the ethyl vanillin swatches in the FFI scale. The perfumer/expert grader needs to demonstrate adequate discrimination on the scale. The perfumer/expert panel is asked to rank order swatches according to a scale between 0 and 3. The panel must demonstrate statistical differences between the swatches as seen in Table 8.

TABLE 8

Results FFI of reference swatches from six perfumers/expert graders.

| FFI | Swatch | Expert Grader 1 | 2 | 3 | 4 | 5 | 6 | Ave | Std Dev. |
|---|---|---|---|---|---|---|---|---|---|
| 0 | Control: stripped swatch NIL ethyl vanillin | 0 | 0 | 0.5 | 0 | 0 | 0 | 0.08 | 0.2 |
| 1 | Stripped swatch with 13 μL 25 ppm ethyl vanillin | 0.5 | 0.5 | 0.5 | 1.5 | 0.5 | 1.0 | 0.75 | 0.4 |
| 2 | Stripped swatch with 13 μL 120 ppm ethyl vanillin | 2.0 | 1.5 | 1.5 | 2.0 | 2.0 | 2.0 | 1.8 | 0.2 |
| 3 | Stripped swatch with 13 μL 1000 ppm ethyl vanillin | 3.0 | 2.0 | 3.0 | 3.0 | 3.0 | 3.0 | 2.8 | 0.4 |

The expert graders must demonstrate a full range of 2.5 over the 4 swatches to be acceptably discriminating. Grader 2 in Table 8 has a range of only 2 and is eliminated from the panel. The panel of expert graders must also demonstrated the ability to statistically discriminate between swatches in the scale.

TABLE 9

This table demonstrates acceptable expert graders with an acceptable range and the panel meets the requirement for discriminating statistics.

| FFI | Swatch | Expert Grader 1 | 3 | 4 | 5 | 6 | Ave | Std Dev. |
|---|---|---|---|---|---|---|---|---|
| 0 | Control: stripped swatch NIL ethyl vanillin | 0 | 0.5 | 0 | 0 | 0 | 0.08 | 0.2 |
| 1 | Stripped swatch with 13 μL 25 ppm ethyl vanillin | 0.5 | 0.5 | 1.5 | 0.5 | 1.0 | 0.80 | 0.4 |
| 2 | Stripped swatch with 13 μL 120 ppm ethyl vanillin | 2.0 | 1.5 | 2.0 | 2.0 | 2.0 | 1.9 | 0.2 |
| 3 | Stripped swatch with 13 μL 1000 ppm ethyl vanillin | 3.0 | 3.0 | 3.0 | 3.0 | 3.0 | 3.0 | 0.0 |

The reference swatches represent the 0, 1, 2, and 3 FFIs on the FFI reference scale, Table 9 below. The expert grader should familiarize them self with the strength of the odor on the FFI reference swatches by sniffing each one starting at 0 (the lowest odor strength) and ending at 3 (the highest odor strength). This should be done prior to evaluating the test sample material treated swatch as shown in Table 10 below.

TABLE 10

Swatch treatments comprising the Fragrance Fidelity Index (FFI) reference scale

| Swatch treatment | Conc. of ethyl vanillin | FFI |
|---|---|---|
| Clean fabric swatch w/13 μL ethyl vanillin | 1000 ppm ethyl vanillin | 3 |
| Clean fabric swatch w/13 μL ethyl vanillin | 120 ppm ethyl vanillin | 2 |
| Clean fabric swatch w/13 μL ethyl vanillin | 25 ppm ethyl vanillin | 1 |
| Clean fabric swatch NIL ethyl vanillin | NIL ethyl vanillin | 0 |

Making Swatches Treated with the Test Material

A clean swatch is treated with 13 μL of a known concentration of a test sample material resulting in an about 1 cm of the solution on the clean swatch. Just like the reference swatches, the test sample material swatch is dried in a vented hood for 30 minutes and then wrapped in aluminum foil to prevent contamination. The test material swatches and the FFI reference swatches should be made within 2 hrs. of each other. The test material swatch must be used within 0.5 to 12 hours and discarded after 12 hours.

Assigning the FFI to the Test Material

At least two perfumers/expert graders are used to assign an FFI grade to a test sample. The perfumer/expert grader smells the test sample swatch by holding that swatch 1 inch from their nose with their nose centered over the area where the test sample was pipetted on to the fabric and then assigns the test sample an FFI grade using the FFI reference scale anchor swatches as references. The test sample swatch is assigned an FFI grade at or between numbers on the FFI scale shown in Table 10. In cases where the test sample material is graded greater than 3, the test material is not a blocker material or the concentration of the material needs to be lowered and reevaluated to determine if a lower level has a malodor blocker functionality.

Method for Assigning the BI to Test Sample

The first step in the method for assigning a BI to a test sample material on the BI reference scale is to create the BI reference swatches. The swatches for the scale are created by treating clean fabrics swatches with a known amount of a known volume of isovaleric acid solution at a known concentration. Fabric swatches for this test are white knit polycotton (4 inch×4 inch) swatches from EMC ordered as PC 50/50. The supplier is instructed to strip the swatches first, stripping involves washing twice with a fragrance-free detergent and rinsing three times.

Making the BI Reference Swatches

Make one solution of 0.08% isovaleric acid using 50%/50% EtOH/water as the diluent. The BI scale contains one clean swatch with no malodor applied. Three other swatches each have a different volume of the 0.08% isovaleric acid applied. Pipette 24 of the 0.08% isovaleric acid solution to one clean swatch, 54 of the 0.08% isovaleric acid solution to the next swatch and 20 μL of isovaleric acid to the final clean swatch. These solutions are pipetted to the middle of the swatches. This will create a sensory scale of three swatches with three different odor levels based on the volume of the 0.08% isovaleric acid solution pipetted onto the swatch. After drying for 30 minutes in a vented hood, the swatches are wrapped in aluminum foil to prevent odor contamination to the treated swatch. A clean untreated swatch is also included as the lowest anchor point of reference for malodor strength on the BI scale. The BI reference scale swatches should be used within 0.5 to 12 hours and discarded after 12 hours. The swatches are used as scale anchor points when graders evaluate a test sample(s) and are assigned a Blocker Index (BI) as show in Table 11 below.

At least four perfumers/expert graders are used to rank the isovaleric acid swatches in the BI scale. The perfumer/expert grader needs to demonstrate adequate discrimination on the scale. The perfumer/expert grader is asked to rank order swatches according to a scale between 0 and 3. The panel of graders must demonstrate statistical differences between the swatches as seen in Table 11.

TABLE 11

Results from six perfumers/expert graders to create the BI scale.

| BI | Swatch | Expert Grader | | | | | Ave | Std Dev. |
|---|---|---|---|---|---|---|---|---|
| | | 1 | 2 | 3 | 4 | 5 | | |
| 0 | Control: stripped swatch NIL isovaleric acid | 0 | 0 | 0 | 0 | 0 | 0 | 0 |
| 1 | Stripped swatch with 2 µL 0.08% isovaleric acid | 0.5 | 2.0 | 1.0 | 1.0 | 0.5 | 1.0 | 0.5 |
| 2 | Stripped swatch with 5 µL 0.08% isovaleric acid | 2.0 | 2.5 | 2.0 | 2.0 | 2.0 | 2.1 | 0.2 |
| 3 | Stripped swatch with 20 µL 0.08% isovaleric acid | 3.0 | 3.0 | 3.0 | 3.0 | 2.5 | 2.8 | 0.2 |

The expert graders must demonstrate a full range of 2.5 over the 4 swatches to be acceptably discriminating. The panel of expert graders must also demonstrated the ability to statistically discriminate between swatches in the scale. Expert grader #2 did not demonstrate the ability to discriminate between the swatches and is eliminated from the panel, see Table 12 below.

TABLE 12

This table demonstrates acceptable expert graders with an acceptable range and the panel meets the requirement for discriminating statistics.

| BI | Swatch | Expert Grader | | | | Ave | Std Dev. |
|---|---|---|---|---|---|---|---|
| | | 1 | 3 | 4 | 5 | | |
| 0 | Control: stripped swatch NIL isovaleric acid | 0 | 0 | 0 | 0 | 0 | 0 |
| 1 | Stripped swatch with 2 µL 0.08% isovaleric acid | 0.5 | 1.0 | 1.0 | 0.5 | 0.8 | 0.3 |
| 2 | Stripped swatch with 5 µL 0.08% isovaleric acid | 2.0 | 2.0 | 2.0 | 2.0 | 2.0 | 0 |
| 3 | Stripped swatch with 20 µL 0.08% isovaleric acid | 3.0 | 3.0 | 3.0 | 2.5 | 2.9 | 0.2 |

The reference swatches represent the 0, 1, 2, and 3 BIs on the BI reference scale, Table 12. The expert grader should familiarizes him/herself with the strength of the odor on the BI reference swatches by sniffing each one starting at 0 (the lowest odor strength) and ending at 3 (the highest odor strength). This should be done prior to evaluating the swatch treated with the test material as shown in Table 13 below.

TABLE 13

Swatch treatments comprising the Blocker Index (BI) reference scale.

| Swatch/treatment | Wt. of isovaleric acid | BI |
|---|---|---|
| Clean fabric swatch w/20 µL 0.08% isovaleric acid | 16 mg isovaleric acid | 3 |
| Clean fabric swatch w/5 µL 0.08% isovaleric acid | 4 mg isovaleric acid | 2 |
| Clean fabric swatch w/2 µL 0.08% isovaleric acid | 1.6 mg isovaleric acid | 1 |
| Clean fabric swatch NIL isovaleric acid | NIL isovaleric acid | 0 |

Making the Malodorous Swatch and Treating it with a Test Material

To evaluate the BI, the test material is applied to a malodorous swatch to determine how well the test material blocks the malodor. The malodorous swatch is made by treating a clean swatch with 20 µL of a 0.08% solution of isovaleric acid. Dry the malodorous swatch treated with isovaleric acid in a vented hood for 30 minutes. After drying the malodorous swatch a known concentration of test material solution, between 1 ppm and 100 ppm is pipetted onto the malodorous swatch. Apply the test material solution right on top of the spot where the isovaleric acid solution was applied making an about 1 cm diameter spot. Just like the BI reference swatches, the isovaleric acid+test material swatch is dried in a vented hood for 30 minutes and then wrapped in aluminum foil to prevent contamination. The isovaleric acid+test material swatches and the BI reference swatches should be made within 2 hrs. of each other. The isovaleric acid+test material swatch must be used between 1-12 hours just like the reference swatches. It is sometimes necessary to evaluate several levels of the test material between about 1 and about 100 ppm to determine the BI.

Assigning the BI to the Test Material

At least two perfumers/expert graders are used to assign the BI to the test sample. The expert grader smells the isovaleric acid+test material swatch by holding that swatch one inch from their nose with their nose centered over the area where the Test sample was pipetted on to the fabric and then assigns the isovaleric acid+test material swatch a BI based on ranking its odor strength against the odor strength of the swatches in the BI reference scale. The test sample swatch is assigned a BI at or between numbers on the BI in Table 14 below. In cases where the isovaleric acid+test material swatch odor is greater than 3 on the BI reference scale, this indicates the material is not a blocker or the concentration of the test material needs to be lowered to achieve its blocker functionality.

TABLE 14

Malodor Reduction Compounds with FFI and BI Grades based on the aforementioned Table

| Ref # | CAS# | log P | Name | Conc | FFI | BI |
|---|---|---|---|---|---|---|
| 281 | 54830-99-8 | 3.11 | 3a,4,5,6,7,7a-hexahydro-4,7-methano-1H-indenyl acetate | 10 ppm | 0 | 2.0 |
| | | | | 50 ppm | 0.5 | 2.0 |
| 677 | 139504-68-0 | 3.75 | 1-((2-(tert-butyl)cyclohexyl)oxy)butan-2-ol | 10 ppm | 0 | 2.3 |
| | | | | 50 ppm | 1.8 | 2.0 |
| 962 | 55066-48-3 | 3.17 | 3-methyl-5-phenylpentan-1-ol | 10 ppm | 0 | 2.3 |
| | | | | 50 ppm | 0.5 | 1.7 |
| 261 | 173445-65-3 | 3.29 | 3-(3,3-dimethyl-2,3-dihydro-1H-inden-5-yl)propanal | 10 ppm | 0 | 1.8 |
| | | | | 50 ppm | 1.3 | 1.3 |

TABLE 14-continued

Malodor Reduction Compounds with FFI and BI Grades based on the aforementioned

| Table Ref # | CAS# | log P | Name | Conc | FFI | BI |
|---|---|---|---|---|---|---|
| 1139 | 87731-18-8 | 2.11 | (Z)-cyclooct-4-en-1-yl methyl carbonate | 10 ppm | 0 | 2.0 |
| | | | | 50 ppm | 1.0 | 2.7 |
| | 4430-31-3 | 1.43 | 3,4,4a,5,6,7,8,8a-octahydrochromen-2-one | 10 ppm | 0 | 2.0 |
| | | | | 50 ppm | 0 | 2.0 |
| 204 | 40379-24-6 | 3.89 | 7-methyloctyl acetate | 10 ppm | 0 | 2.0 |
| | | | | 50 ppm | 0 | 2.7 |
| 1005 | 93981-50-1 | 5.59 | ethyl (2,3,6-trimethylcyclohexyl) carbonate | 50 ppm | 0.5 | 2.6 |
| 391 | 106-33-2 | 5.73 | Ethyl laurate | 50 ppm | 0.3 | 2.2 |
| 1148 | 1139-30-6 | 4.06 | Caryophyllene Oxide | 50 ppm | 0.5 | 2.3 |
| 524 | 13877-91-3 3338-55-4 | 4.31 | 3,7-Dimethyl-1,3,6-Octatriene(cis-β ocimene 70%) | 50 ppm | 0 | 2.8 |
| 1149 | 23787-90-8 | 4 | 1,3,4,6,7,8alpha-hexahydro-1,1,5,5-tetramethyl-2H-2,4alpha-methanophtalen-8(5H)-one | 10 ppm | 0 | 1.5 |
| | | | | 50 ppm | 0.8 | 2.3 |
| | 112-42-5 | 4.62 | Undecanol | 50 ppm | 0.8 | 2.3 |
| 174 | 112-53-8 | 5.17 | 1-dodecanol | 50 ppm | 0.5 | 2.3 |
| | 98-52-2 | 2.78 | 4-tert-butyl cyclohexane | 10 ppm | 0 | 2.0 |
| | | | | 50 ppm | 0.3 | 2.0 |
| 109 | 112-39-0 | 6.41 | Methyl palmitate | 10 ppm | | 2.0 |

Malodor control compounds with improved performance at lower levels.

Set forth below in Table 15 are some non-limiting examples of desirable behavior by which the malodor control compound gives improved malodor control at lower concentration. These nonlimiting data provide additional compelling data that malodor is being blocked, not masked.

TABLE 15

| Table Ref # | CAS# | Name | Conc | FFI | BI |
|---|---|---|---|---|---|
| N/A | 68912-13-0 | 8,8-dimethyl-3a,4,5,6,7,7a-hexahydro-1H-4,7-methanoinden-6-yl propionate | 10 ppm | 0 | 1.5 |
| | | | 50 ppm | 0 | 2.2 |
| N/A | TBD | 4,8-dimethyl-1-(methylethyl)-7-oxybiciclo [4.3.0]nonane | 10 ppm | 2.0 | 2.0 |
| | | | 50 ppm | 0.3 | 2.2 |

Retesting malodor reduction compounds at lower levels.

The example below as shown in Table 16 demonstrates that while a malodor control compound could fail to demonstrate odor blocking (BI>2.5) at a higher concentration it should be retested at a lower concentration to determine if it passes.

TABLE 16

| Table Ref # | CAS# | Name | Conc | FFI | BI |
|---|---|---|---|---|---|
| N/A | 173445-65-3 | 1H-Indene-5-propanal, 2,3-dihydro-3,3-dimethyl- | 10 ppm | 0 | 1.5 |
| | | | 50 ppm | 0.5 | 2.7 |

NON-LIMITING EXAMPLES OF MALODOR REDUCTION COMPOSITIONS

Example 1 Compositions Comprising Malodor Reduction Compounds

In the present invention blends enable more potent malodor reduction because blends are useful at a higher % of the product composition before becoming olfactively noticeable. Below are non-limiting examples of malodor reduction compounds.

| Component | CAS# | % wt. Active | | | | |
|---|---|---|---|---|---|---|
| | | A | B | C | D | E |
| 2,2,8,8-tetramethyl-octahydro-1H-2,4a-methanonapthalene-10-one | 29461-14-1 | 35-45 | 15-25 | 5-20 | 10-30 | 15-25 |
| 1H-Indene-ar-propanal,2,3-dihydro-1,1-dimethyl- | 300371-33-9 | 10-20 | 1-30 | NIL | 5-10 | 1-5 |
| Hexadecanoic acid, (2E)-3,7-dimethyl-2,6-octadien-1-yl ester | 3681-73-0 | 35-45 | 10-25 | NIL | 30-40 | 35-50 |
| 1-Pentanol-3-methyl-5-phenyl | 55066-48-3 | 10-20 | 10-25 | 2-10 | 5-17 | 10 |
| 4,7-Methano-1H-inden-5-ol, 3a,4,5,6,7,7a-hexahydro-, 5-acetate | 171102-41-3 | 0-5 | 10-25 | NIL | 1-6 | 1-5 |
| 4,8-dimethyl-1-(methylethyl)-7-oxybiciclo [4.3.0]nonane | N/A | 0-5 | NIL | NIL | NIL | 1-5 |
| (3Z)-3,7-dimethylocta-1,3,6-triene | 3338-55-4 | NIL | NIL | 10-20 | 2-5 | NIL |
| 1H-Indene-5-propanal, 2,3-dihydro-3,3-dimethyl- | 173445-65-3 | NIL | NIL | NIL | 7.5-16 | 1-15 |
| 3,4,4a,5,6,7,8,8a-octahydrochromen-2-one | 4430-31-3 | NIL | NIL | NIL | 3-7 | 1-15 |
| 1-(2-tert-butylcyclohexyl)oxybutan-2-ol | 139504-68-0 | NIL | NIL | NIL | 0.25-1.5 | NIL |

-continued

| Component | CAS# | % wt. Active | | | | |
|---|---|---|---|---|---|---|
| | | A | B | C | D | E |
| ethyl (2,3,6-trimethylcyclohexyl) carbonate | 93981-50-1 | NIL | NIL | 15-30 | NIL | 2 |
| benzyl 2-hydroxypropanoate | 2051-96-9 | NIL | NIL | 2-5 | NIL | NIL |
| (3,5-dimethylcyclohex-3-en-1-yl)methanol | 67634-16-6 | NIL | NIL | 5-30 | NIL | NIL |
| 2-Dodecanol | 10203-28-8 | NIL | 0.25-1 | NIL | 0.5-3 | NIL |

Example 2 Compositions Comprising Malodor Reduction Compounds

| Ingredient | CAS # | % wt. Active | | | | | |
|---|---|---|---|---|---|---|---|
| | | A | B | C | B | D | E |
| (E)-1-(2,6,6-trimethyl-1-cyclohex-2-enyl)pent-1-en-3-one | 127-42-4 | 4 | 8 | 2 | 8 | 3 | 2 |
| ethyl dodecanoate | 106-33-2 | NIL | 1 | NIL | 3 | NIL | NIL |
| 3a,4,5,6,7,7a-hexahydro-1H-4,7-methanoinden-1-yl propanoate | 68912-13-0 | 8 | 30 | 1 | 4 | 1 | 3.5 |
| [1R-(1R*,4R*,6R*,10S*)]-4,12,12-trimethyl-9-methylene-5-oxatricyclo[8.2.0.04,6]dodecane | 1139-30-6 | NIL | 0.3 | 2 | 0.5 | NIL | 0.5 |
| (8E)-cyclohexadec-8-en-1-one | 3100-36-5 | NIL | 5 | NIL | 7 | NIL | NIL |
| 3,5,5-trimethylhexyl acetate | 58430-94-7 | 25 | 15 | 50 | 35 | 60 | 56 |
| ethyl (2,3,6-trimethylcyclohexyl) carbonate | 93981-50-1 | NIL | 1 | NIL | 5 | NIL | NIL |
| 2,4-dimethyl-4,4a,5,9b-tetrahydroindeno[1,2-d][1,3]dioxine | 27606-09-3 | 25 | 10 | 15 | 15 | 16 | 15 |
| 2,2,7,7-tetramethyltricyclo[6.2.01,6]undecan-5-one | 23787-90-8 | 8 | 9 | 5 | 7 | 5 | 5 |
| (3,5-dimethylcyclohex-3-en-1-yl)methanol | 67634-16-6 | NIL | 0.7 | NIL | 0.5 | NIL | NIL |
| 3-(7,7-dimethyl-4-bicyclo[3.1.1]hept-3-enyl)-2,2-dimethylpropanal | 33885-52-8 | 30 | 20 | 25 | 15 | 15 | 18 |
| Total | | 100 | 100 | 100 | 100 | 100 | 100 |

Example 3 Malodor Reduction Composition

| Ingredient | CAS # | % wt. Active | | |
|---|---|---|---|---|
| | | A | B | C |
| 5-Cyclohexadecen-1-One | 37609-25-9 | 15.0 | 2.00 | 2.00 |
| decahydro-2,2,7,7,8,9,9-heptamethylindeno(4,3a-b)furan | 476332-65-7 | 0.005 | 0.01 | 0.01 |
| 2,3-Dihydro-5,6-dimethoxy-2-(4-piperidinylmethylene)-1H-inden-1-one | 33704-61-9 | 0.3 | 0.5 | 0.5 |
| Cedryl Methyl Ether | 19870-74-7 | 6.0 | 10.0 | 4.0 |
| Trans-4-Decenal | 65405-70-1 | 0.005 | 0.002 | 0.002 |
| Decyl Aldehyde | 112-31-2 | 3.74 | 2.0 | 2.0 |
| 3-methyl cyclopentadecenone | 63314-79-4 | 0.4 | 1.0 | 1.0 |
| Diphenyl Oxide | 101-84-8 | 0.5 | 1.0 | 1.0 |
| 3a,4,5,6,7,7a-hexahydro-4,7-methano-1H-indenyl acetate | 54830-99-8 | 5.0 | 8.0 | 8.0 |
| 3a,4,5,6,7,7a-hexahydro-1H-4,7-methanoinden-1-yl propanoate | 68912-13-0 | 6.0 | 8.0 | 8.0 |

-continued

| Ingredient | CAS # | % wt. Active | | |
|---|---|---|---|---|
| | | A | B | C |
| 2-(5-methyl-2-propan-2-yl-8-bicyclo[2.2.2]oct-5-enyl)-1,3-dioxolane | 68901-32-6 | 10.0 | 15.0 | 15.0 |
| (E)-3,7-dimethyl-2,6-octadienylhexadecanoate | 3681-73-0 | 10.0 | 10.0 | 16.0 |
| Iso Nonyl Acetate | 58430-94-7 | 6.65 | 8.0 | 3.0 |
| 2,2,7,7-tetramethyltricyclo[6.2.1.01,6]undecan-5-one | 23787-90-8 | 10.0 | 8.0 | 8.0 |
| (1-Methyl-2-(1,2,2-trimethylbicyclo[3.1.0]-hex-3-ylmethyl)cyclopropyl)methanol | 198404-98-7 | 0.1 | 0.3 | 0.3 |
| Lauric Aldehyde | 112-54-9 | 0.625 | 1.0 | 0.7 |
| Methyl Iso Eugenol | 93-16-3 | 18.000 | 10.0 | 13.0 |
| Methyl hexadecanoate | 112-39-0 | 3.000 | 10.0 | 12.0 |
| 2,3-dihydro-1,1--dimethyl-1H-indene-ar-propanal | 300371-33-9 | 0.400 | 0.0 | 0.3 |
| 4-tert-butylcyclohexanol | 98-52-2 | 0.400 | 0.1 | 0.1 |
| 2-isobutyl-4-hydroxy-4-methyltetrahydropyran | 63500-71-0 | 1.600 | 2.0 | 2.0 |
| Undecyl Aldehyde | 112-44-7 | 1.725 | 2.888 | 1.888 |
| Undecylenic Aldehyde | 112-45-8 | 0.550 | 0.2 | 1.2 |
| Total | | 100 | 100.0 | 100.0 |

Each of the malodor reduction compositions of Examples 1 through 3 are used as a perfume component in a fibrous structure at a level of form about 0.00001 mg to about 50 mg by combining the malodor reduction composition at a level of about 0.01% to about 30% based on total perfume composition weight. Addition Examples are as follows:

Non-Limiting Examples of Rolled Fibrous Structures

Example 4

A first stock chest of 100% *eucalyptus* fiber is prepared with a conventional pulper to have a consistency of about 3.0% by weight. The thick stock of the first hardwood chest is directed through a thick stock line where a wet-strength additive, HERCOBOND 1194 (commercially available from Ashland Inc.), a temporary wet strength agent, is added in-line to the thick stock at about 0.5 lbs. per ton of dry fiber as it moves to the first fan pump.

Additionally, a second stock chest of 100% *eucalyptus* fiber is prepared with a conventional pulper to have a consistency of about 3.0% by weight. The thick stock of the second hardwood chest is directed through a thick stock line where a wet-strength additive, HERCOBOND 1194, is added in-line to the thick stock at about 0.5 lbs. per ton of dry fiber as it moves to the second fan pump.

A third stock chest is prepared with 100% NSK fiber with a final consistency of about 3.0%. The blended thick stock is directed to a disk refiner where it is refined to a Canadian Standard Freeness of about 580 to 625. The NSK thick stock of the third stock chest is then directed through a thick stock line where a wet-strength additive, HERCOBOND 1194, is added to the thick stock at about 1.5 lbs. per ton of dry fiber. The refined, 100% NSK thick stock is then directed to a third fan pump.

The *eucalyptus* fiber slurry diluted by the first fan pump is directed through the bottom headbox chamber (Yankee-side layer). The NSK fiber slurry diluted by the third fan pump is directed through the center headbox chamber. The *eucalyptus* fiber slurry diluted by the second fan pump directed to the top headbox chamber (Fabric-side) and delivered in superposed relation to the fixed-roof former's forming wire to form thereon a three-layer embryonic web, of which about 34.5% of the top side is made up of pure *eucalyptus* fibers, center is made up of about 34.5% of a NSK fiber and the bottom side (Yankee-side) is made up of about 34.5% of pure *eucalyptus* fiber. Dewatering occurs through the outer wire and the inner wire and is assisted by wire vacuum boxes. Forming wire is an 84M design traveling at a speed of 800 fpm (feet per minute).

The embryonic wet web is transferred from the carrier (inner) wire, at a fiber consistency of about 24% at the point of transfer, to a patterned drying fabric. The speed of the patterned drying fabric is about 800 fpm (feet per minute). The drying fabric is designed to yield a pattern of substantially machine direction oriented linear channels having a continuous or semi-continuous network of high density (knuckle) areas. This drying fabric is formed by casting an impervious resin surface onto a fiber mesh supporting fabric. The supporting fabric is a 127×52 filament, dual layer mesh. The thickness of the resin cast is about 12 mils above the supporting fabric.

While remaining in contact with the patterned drying fabric, the web is pre-dried by air blow-through pre-dryers to a fiber consistency of about 60% by weight.

After the pre-dryers, the semi-dry web is transferred to the Yankee dryer through a nip formed by the pressure roll surface and the Yankee surface where the Yankee surface has been pre-treated with a sprayed a creping adhesive coating. The coating is a blend consisting of Georgia Pacific's UNICREPE 457T20 and Vinylon Works' VINYLON 8844 at a ratio of about 92 to 8, respectively. The fiber consistency is increased to about 97% before the web is dry creped from the Yankee with a doctor blade.

The web is removed from the Yankee surface by a creping blade having a bevel angle of about 25 degrees and is positioned with respect to the Yankee dryer to provide an impact angle of about 81 degrees. The Yankee dryer is operated at a temperature of about 350° F. (177° C.) and a speed of about 800 fpm. The fibrous structure is wound in a roll using a surface driven reel drum having a surface speed of about 700 fpm (feet per minute) to make a parent roll.

One or more encapsulated malodor reduction compositions, for example described herein, is applied, to a surface of a core opposite the surface of the core upon which the finished fibrous sturcture is wound.

Example 5

Individual fibrous structure plies are made according to the process detailed in Example 4 supra. Two plies are combined with the wire side facing out. During the converting process, a surface softening agent and a lotion are applied sequentially with slot extrusion dies to the outside surface of both plies. The surface softening agent is a formula comprising one or more polyhydroxy compounds (Polyethylene glycol, Polypropylene glycol, and/or copolymers thereof marketed by BASF Corporation of Florham Park, N.J.), glycerin (marketed by PG Chemical Company), and silicone (i.e. MR-1003, marketed by Wacker Chemical Corporation of Adrian, Mich.). The surface softening agent is applied to the web at a rate of 14.1% by weight and the lotion is applied to the web at a rate of 5.0% by weight. The plies are then bonded together with ply bond glue and optionally embossed, and then converted into a finished 2-ply sanitary tissue product, for example toilet tissue.

One or more encapsulated malodor reduction compositions, for example described herein, is applied, to a surface of a core opposite the surface of the core upon which the finished fibrous sturcture is wound.

Example 6

Individual fibrous structure plies are made according to the process detailed in Example 4 supra. Two plies are combined with the wire side facing out. During the converting process, a surface softening agent and a lotion are applied sequentially with slot extrusion dies to the outside surface of both plies. The surface softening agent is a formula comprising one or more polyhydroxy compounds (Polyethylene glycol, Polypropylene glycol, and/or copolymers thereof marketed by BASF Corporation of Florham Park, N.J.), glycerin (marketed by PG Chemical Company), and silicone (i.e. MR-1003, marketed by Wacker Chemical Corporation of Adrian, Mich.). The surface softening agent is applied to the web at a rate of 10.0% by weight and the lotion is applied to the web at a rate of 5.0% by weight. The plies are then bonded together with ply bond glue and optionally embossed, and then converted into a finished 2-ply sanitary tissue product, for example toilet tissue.

One or more encapsulated malodor reduction compositions, for example described herein, is applied, to a surface of a core opposite the surface of the core upon which the finished fibrous sturcture is wound.

Example 7

Individual fibrous structure plies are made according to the process detailed in Example 4 supra. Two plies are combined with the wire side facing out. During the converting process, a surface softening agent and a lotion are applied sequentially with slot extrusion dies to the outside surface of both plies. The surface softening agent is a formula comprising one or more polyhydroxy compounds (Polyethylene glycol, Polypropylene glycol, and/or copolymers thereof marketed by BASF Corporation of Florham Park, N.J.), glycerin (marketed by PG Chemical Company), and silicone (i.e. MR-1003, marketed by Wacker Chemical Corporation of Adrian, Mich.). The surface softening agent is applied to the web at a rate of 10.0% by weight and the lotion is applied to the web at a rate of 10.4% by weight. The plies are then bonded together with ply bond glue and optionally embossed, and then converted into a finished 2-ply sanitary tissue product, for example toilet tissue.

One or more encapsulated malodor reduction compositions, for example described herein, is applied, to a surface of a core opposite the surface of the core upon which the finished fibrous sturcture is wound.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is, therefore, intended to cover in the appended claims all such changes and modifications that are within the scope of this invention.

What is claimed:
1. A roll of fibrous structure comprising:
   a core upon which the fibrous structure is convolutely wound;
   wherein the core comprises one or more malodor reduction compositions encapsulated by a polymer shell and capable of being released upon rupture of the polymer shell;
   wherein the polymer shell comprises polyacrylate;
   wherein at least one of the malodor reduction compositions comprises one or more carrier materials.
2. The roll of fibrous structure according to claim 1 wherein at least one of the carrier materials is selected from the group consisting of: polyacrylate, melamine, wax, cyclodextrin, bulk starch, cyclic(cyclodextrin), helical starch, and mixtures thereof.
3. The roll of fibrous structure according to claim 1 wherein the fibrous structure comprises from about 0.0001 mg to about 50 mg of at least one of the malodor reduction materials.
4. The roll of fibrous structure according to claim 1 wherein the fibrous structure comprises from about 0.001 mg to about 7 mg of at least one of the malodor reduction materials.
5. The roll of fibrous structure according to claim 1 wherein at least one of the malodor reduction materials exhibits a Malodor Reduction Value (MORV) of at least 0.5.

6. The roll of fibrous structure according to claim 1 wherein all of the malodor reduction materials exhibit a Malodor Reduction Value of at least 0.5.

7. The roll of fibrous structure according to claim 1 wherein at least one of the malodor reduction materials exhibits a Universal Malodor Reduction Value (MORV) of at least 0.5.

8. The roll of fibrous structure according to claim 1 wherein at least one of the malodor reduction materials exhibits a Blocker Index of less than 3.

9. The roll of fibrous structure according to claim 1 wherein at least one of the malodor reduction materials exhibits a Blocker Index Average of from 3 to 0.001.

10. The roll of fibrous structure according to claim 1 wherein at least one of the malodor reduction materials exhibits a Fragrance Fidelity Index of less than 3.

11. The roll of fibrous structure according to claim 1 wherein at least one of the malodor reduction materials exhibit a Fragrance Fidelity Index Average of from 3 to 0.001.

12. The roll of fibrous structure according to claim 1 wherein at least one of the malodor reduction materials is selected from the group consisting of (E)-cyclohexadec-5-en-1-one; 2,2,7,7,8,9,9-heptamethyldecahydroindeno [4,3a-b] furan; 2,3-dihydro-3,3-dimethyl-1H-indene-5-propanal; 3-(3,3-dimethyl-2,3-dihydro-1H-inden-5-yl)propanal; 2,3-dihydro-1,1-dimethyl-1H-indene-ar-propanal; 4,8-Dimethyl-1-(methylethyl)-7-oxabicyclo[4.3.0] nonane; 4,5-epoxy-4,11,11-trimethyl-8-methylenebicyclo(7.2.0)undecane; 1,3,4,6,7,8alpha-hexahydro-1,1,5,5-tetramethyl-2H-2,4alpha-methanophtalen-8(5H)-one and mixtures thereof.

13. The roll of fibrous structure according to claim 1 wherein at least one of the malodor reduction materials exhibits a log P≥3.

14. The roll of fibrous structure according to claim 13 wherein at least one of the malodor reduction materials is selected from the group consisting of 3-(3,3-dimethyl-2,3-dihydro-1H-inden-5-yl)propanal; 8,8-dimethyl-3a,4,5,6,7,7a-hexahydro-1H-4,7-methanoinden-6-yl acetate; 2,2,7,7,8,9,9-heptamethyldecahydroindeno[4,3a-b]furan; (E)-cyclohexadec-5-en-1-one; 4,5-epoxy-4,11,11-trimethyl-8-methylenebicyclo(7.2.0)undecane; 1,3,4,6,7,8alpha-hexahydro-1,1,5,5-tetramethyl-2H-2,4alpha-methanophtalen-8(5H)-one; 2,3-dihydro-1,1-dimethyl-1H-indene-ar-propanal; 4,8-Dimethyl-1-(methylethyl)-7-oxabicyclo[4.3.0] nonane and mixtures thereof.

15. The roll of fibrous structure according to claim 1 wherein at least one of the malodor reduction materials is not a material selected from the group consisting of geranyl nitrile; helional; nonanal; linalool; (S)-(+)-linalool; (R)-(−)-linalool; nerol; tetrahydrolinalool; 2-phenylethyl acetate; eugenol; ethyl linalool; allyl heptoate; agrumen nitrile; citronitrile; 2,2-dimethyl-3-(m-tolyl)propan-1-ol; 2-methyl-5-phenylpentan-1-ol; dodecanenitrile; 2-heptylcyclopentan-1-one; methyl nonyl acetaldehyde; 3-(2-ethylphenyl)-2,2-dimethylpropanal; (Z)-1-(2,6,6-trimethylcyclohex-2-en-1-yl)but-2-en-1-one; (R,E)-2-methyl-4-(2,2,3-trimethylcyclopent-3-en-1-yl)but-2-en-1-ol; 4-(tert-butyl) cyclohexyl acetate; 1-cyclohexylethyl (E)-but-2-enoate; allyl 2-(cyclohexyloxy)acetate; alpha terpinyl acetate; beta terpinyl acetate; gamma terpinyl acetate; methyl dodecyl ether; 2,4-dimethyl-4,4a,5,9b-tetrahydroindeno[1,2-d][1,3] dioxine; cinnamyl isobutyrate; (E)-2-methyl-4-(2,6,6-trimethylcyclohex-1-en-1-yl)but-2-enal; gamma methyl ionone; ethyl 2,3,6-trimethyl cyclohexyl carbonate ethyl 2,3,6-trimethyl cyclohexyl carbonate; Citral diethyl acetal; Dimethoxycyclododecane; 1-((2S,3S)-2,3,8,8-tetramethyl-1,2,3,4,5,6,7,8-octahydronaphthalen-2-yl)ethan-1-one; oxacyclohexadecan-2-one; 4,6,6,7,8,8-hexamethyl-1,3,4,6,7,8-hexahydrocyclopenta[g]isochromene; Ethylene brassylate; Methyl (Z)-2-((3-(4-(tert-butyl)phenyl)-2-methylpropylidene)amino)benzoate; 4,7-Methano-1H-inden-5-ol, 3a,4,5,6,7,7a-hexahydro-, 5-acetate; cedryl methyl ether; vetivert acetate; 1-((3R,3aR,7R,8aS)-3,6,8,8-tetramethyl-2,3,4,7,8,8a-hexahydro-1H-3a,7-methanoazulen-5-yl)ethan-1-one; Benzophenone; Farnesol; trans,trans-farnesol; 3-(3-isopropylphenyl)butanal; 2,6,10-trimethylundec-9-enal; 3-(4-(tert-butyl)phenyl)propanal; 3-(4-isopropylphenyl)-2-methylpropanal; Citronellal (1); Citronellal (d); (E)-4,8-dimethyldeca-4,9-dienal; Pino Acetaldehyde; 3-(4-(tert-butyl)phenyl)-2-methylpropanal; Cinnamic aldehyde; Citral; Geranial; MethoxyMelonal; o-methoxycinnamaldehyde; (E)-4-((3aS,7aS)-octahydro-5H-4,7-methanoinden-5-ylidene)butanal; Methyl Octyl Acetaldehyde; 3-(4-methoxyphenyl)-2-methylpropanal; 5-methoxyoctahydro-1H-4,7-methanoindene-2-carbaldehyde; Iso Cyclocitral; Octanal; 2-Undecenal; 10-Undecenal; Trans-trans-2,6-Nonadienal; Trans-2,cis-6-nondienal; Heliotropin; Hexyl Cinnamic aldehyde; p-methyl-alpha-pentylcinnamaldehyde; Alpha-methyl cinnamaldehyde; 3,4-dimethoxybenzaldehyde; Myrtenal; Perillaldehyde; Maceal; Methyl palmitate; Methyl iso eugenol and mixtures thereof.

16. The roll of fibrous structure according to claim 1 wherein the fibrous structure further comprises a perfume.

17. The roll of fibrous structure according to claim 16 wherein the perfume and the one or more malodor reduction compositions are present at a ratio of perfume to the sum total of the malodor reductions materials of from about 300,000:1 to about 1:1.

18. The roll of fibrous structure according to claim 17 wherein the perfume and the one or more malodor reduction compositions are present at a ratio of perfume to the sum total of the malodor reductions materials of from about 100,000:1 to about 1:1.

19. The roll of fibrous structure according to claim 18 wherein the perfume and the one or more malodor reduction compositions are present at a ratio of perfume to the sum total of the malodor reductions materials of from about 50,000:1 to about 1:1.

20. The roll of fibrous structure according to claim 19 wherein the perfume and the one or more malodor reduction compositions are present at a ratio of perfume to the sum total of the malodor reductions materials of from about 20:1 to about 1:1.

* * * * *